United States Patent
Fan et al.

(10) Patent No.: US 11,535,606 B2
(45) Date of Patent: Dec. 27, 2022

(54) SUBSTITUTED QUINOLINE-8-CARBONITRILE DERIVATIVES WITH ANDROGEN RECEPTOR DEGRADATION ACTIVITY AND USES THEREOF

(71) Applicant: ACCUTAR BIOTECHNOLOGY INC., Brooklyn, NY (US)

(72) Inventors: Jie Fan, New York, NY (US); Yimin Qian, Plainsboro, NJ (US); Wei He, Zionsville, IN (US); Ke Liu, Shanghai (CN)

(73) Assignee: Accutar Biotechnology Inc., Brooklyn, NY (US)

( * ) Notice: Subject to any disclaimer, the term of this patent is extended or adjusted under 35 U.S.C. 154(b) by 122 days.

(21) Appl. No.: 17/028,689

(22) Filed: Sep. 22, 2020

(65) Prior Publication Data

US 2021/0087171 A1 Mar. 25, 2021

Related U.S. Application Data

(60) Provisional application No. 62/904,017, filed on Sep. 23, 2019.

(51) Int. Cl.
 *C07D 401/14* (2006.01)
(52) U.S. Cl.
 CPC ............... *C07D 401/14* (2013.01)

(58) Field of Classification Search
 CPC .................................................. C07D 401/14
 USPC .................................................... 514/253.06
 See application file for complete search history.

(56) References Cited

U.S. PATENT DOCUMENTS

| | | | |
|---|---|---|---|
| 8,158,653 | B2 | 4/2012 | Muller et al. |
| 2009/0148853 | A1 | 6/2009 | Schafer et al. |
| 2018/0179183 | A1 | 6/2018 | Crew et al. |

FOREIGN PATENT DOCUMENTS

WO  WO 1998/003502 A1  1/1998

OTHER PUBLICATIONS

International Search Report for International Application No. PCT/US2020/051999, dated Dec. 3, 2020.
Written Opinion of the International Search Authority for International Application No. PCT/US2020/051999, dated Dec. 3, 2020.

*Primary Examiner* — Ana Z Muresan
(74) *Attorney, Agent, or Firm* — Finnegan, Henderson, Farabow, Garrett & Dunner, LLP

(57) ABSTRACT

The present disclosure relates to novel compounds, pharmaceutical compositions containing such compounds, and their use in prevention and treatment of cancer and related diseases and conditions. In some embodiments, the compounds disclosed herein exhibit androgen receptor degradation activity.

34 Claims, 1 Drawing Sheet

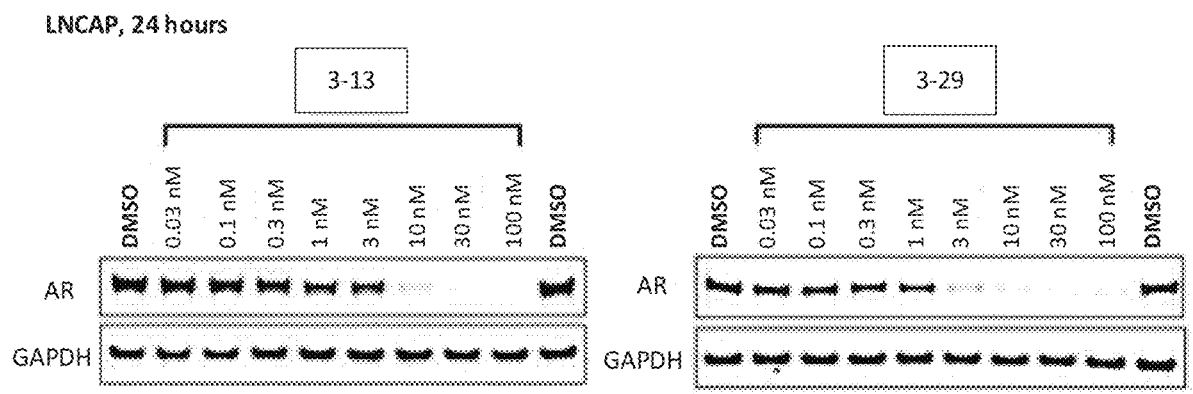

SUBSTITUTED QUINOLINE-8-CARBONITRILE DERIVATIVES WITH ANDROGEN RECEPTOR DEGRADATION ACTIVITY AND USES THEREOF

This application claims priority from U.S. Provisional Patent Application No. 62/904,017, filed Sep. 23, 2019, which is hereby incorporated by reference in its entirety.

FIELD OF THE DISCLOSURE

The present disclosure relates to novel compounds, pharmaceutical compositions containing such compounds, and their use in prevention and treatment of diseases and conditions, e.g., cancer. The compounds disclosed herein exhibit androgen receptor degradation activity.

BACKGROUND OF THE DISCLOSURE

Androgens, through binding to the Androgen Receptor (AR), govern a wide range of physiological processes. For example, androgens are required for normal prostate development and function as they are key in the AR signaling pathway. Unfortunately, the AR signaling pathway is also implicated in the development and survival of cancers, such as prostate, breast, and other cancers (see, e.g., "Androgen Receptor in Prostate Cancer", Endocrine Reviews, 2004, 25(2), 276-308; and "Androgen receptors beyond prostate cancer: ann old marker as a new target", Oncotarget, 2014, 6(2), 592-603).

Traditional methods to treat cancers where AR is implicated, such as prostate cancer, involves AR signaling suppression through, for example, androgen deprivation therapy. Such therapy includes chemical and/or surgical castration. Alternatively, anti-androgen therapy may be pursued, whereby a patient is treated with an AR inhibitor, such as enzalutamide (XTANDI®). Although these treatment methods have resulted in improved prognoses for individuals with androgen receptor positive cancer, cancer progression is eventually observed and occurs through, for example, AR gene amplification and/or development of AR mutations.

Accordingly, there exists a need to treat AR positive cancer that halts progression of the cancer, even if the individual has experienced one or more prior therapies. One approach to achieve this goal would be to utilize the naturally occurring cellular ubiquitin-mediated degradation. Without being bound to any theory, it is believed that AR degradation may occur when both AR and a ubiquitin ligase are bound and brought into close proximity.

Cereblon ("CRBN") E3 ubiquitin ligase is a ubiquitin ligase that forms an E3 ubiquitin ligase complex with damaged DNA binding protein 1 and Cullin 4. It functions as a substrate receptor by bringing the substrates to close proximity for ubiquitination and subsequent degradation by proteasomes. Recently, it has been discovered that small molecules drugs, e.g., thalidomide and its close analogs, lenalidomide and pomalidomide, can simultaneously interact with CRBN and some other proteins. In doing so, CRBN may be exploited for target protein degradation, such as IKZF1 and IKZF3. This is thought to account for the anti-myeloma effects of thalidomide and related compounds.

Thus, disclosed herein are compounds useful for the treatment of cancers, such as prostate cancer. In some instances, the cancer is AR positive. The compounds disclosed herein are bifunctional molecules, where one portion of the molecule is capable of interacting with CRBN and the other portion, which is linked to the CRBN-interacting portion of the molecule via a linking moiety, is capable of interacting with AR.

SUMMARY OF THE DISCLOSURE

In some embodiments, the present disclosure is directed to a compound of Formula (1), or a pharmaceutically acceptable salt thereof:

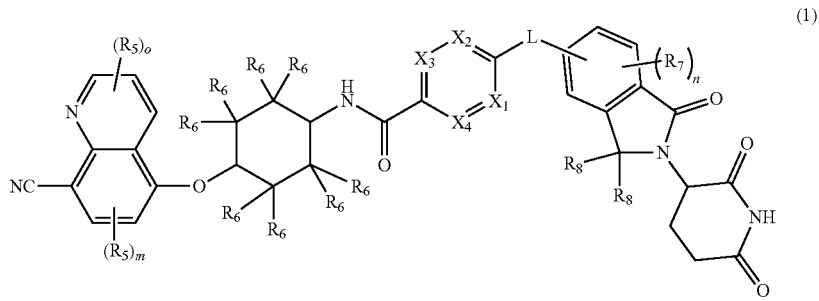

(1)

wherein:
$X_1$ is $CR_1$ or N;
$X_2$ is $CR_2$ or N;
$X_3$ is $CR_3$ or N;
$X_4$ is $CR_4$ or N;
each of $R_1$, $R_2$, $R_3$, and $R_4$ is independently selected from hydrogen, halogen, $C_1$-$C_3$alkoxy, and $C_1$-$C_3$haloalkyl, each of which is substituted with 0, 1, 2, or 3 $R_S$;
each $R_5$ is independently selected from halogen, hydroxyl, $C_1$-$C_3$alkyl, $C_1$-$C_3$alkoxy, $C_1$-$C_3$haloalkyl, —N($R_9$)$_2$, and —CN, each of which is substituted with 0, 1, 2, or 3 $R_S$;
each $R_6$ is independently selected from hydrogen, halogen, $C_1$-$C_3$alkyl, and $C_1$-$C_3$haloalkyl, each of which is substituted with 0, 1, 2, or 3 $R_S$, or two $R_6$ groups are taken together to form an oxo;
each $R_7$ is independently selected from halogen, hydroxyl, $C_1$-$C_3$alkyl, $C_1$-$C_3$alkoxy, $C_1$-$C_3$haloalkyl, —N($R_9$)$_2$, and —CN, each of which is substituted with 0, 1, 2, or 3 $R_S$;
each $R_8$ is independently selected from hydrogen, hydroxyl, $C_1$-$C_3$alkyl, and $C_1$-$C_3$haloalkyl, each of which is substituted with 0, 1, 2, or 3 $R_S$, or two $R_8$ groups are taken together to form an oxo;
each $R_9$ is independently selected from hydrogen, $C_1$-$C_3$alkyl, —C(═O)—($C_1$-$C_3$alkyl), —C(═O)—O—

($C_1$-$C_3$alkyl), and —C(=O)—NH—($C_1$-$C_3$alkyl), each of which is substituted with 0, 1, 2, or 3 $R_S$, or two $R_9$ groups are taken together to form a 3- to 6-membered heterocycle or heteroaryl;

each $R_S$ is independently selected from halogen, hydroxyl, $C_1$-$C_3$alkyl, $C_1$-$C_3$alkoxy, $C_1$-$C_3$haloalkyl, —N($R_9$)$_2$, and —CN;

L is a linker of 1 to 16 carbon atoms in length, wherein one or more carbon atoms are optionally replaced by C(O), O, N($R_9$), S, $C_2$-alkenyl, $C_2$-alkynyl, cycloalkyl, aryl, heterocycle, or heteroaryl, wherein the $R_9$, $C_2$-alkenyl, cycloalkyl, aryl, heterocycle, and heteroaryl are each independently substituted with 0, 1, 2, or 3 $R_S$;

m is 0, 1, or 2;
n is 0, 1, 2, or 3; and
o is 0, 1, 2, or 3, wherein each hydrogen atom is independently and optionally replaced by a deuterium atom.

In some embodiments, the compound of Formula (1) may be a compound of Formula (1A)

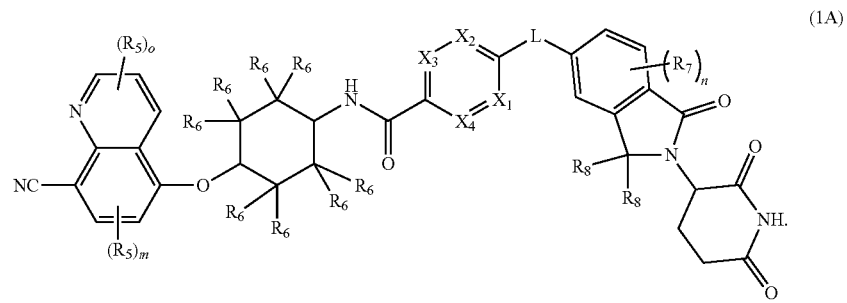

(1A)

In some embodiments, the

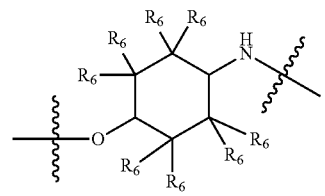

group is selected from

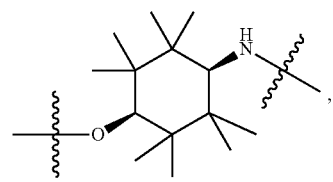

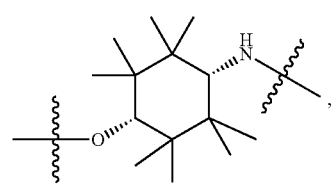

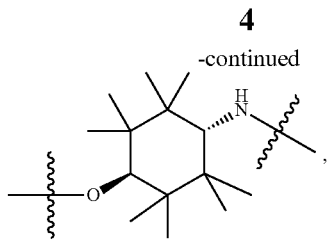

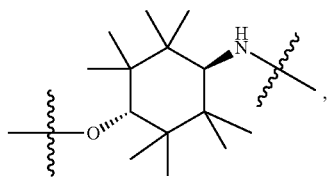

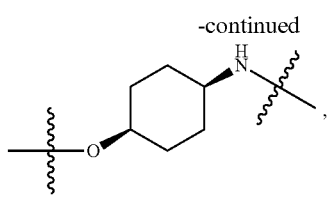

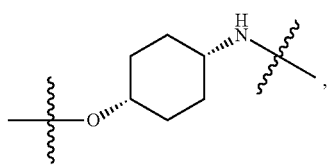

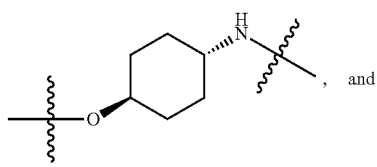, and

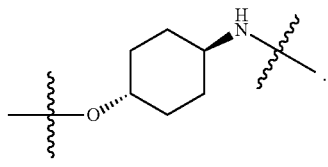.

In some embodiments, the
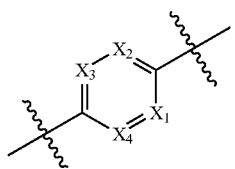
group may be selected from
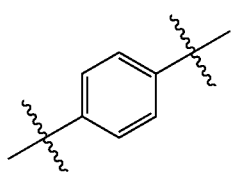, 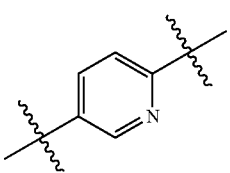,
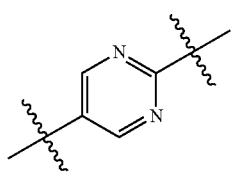, 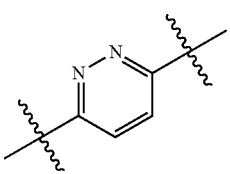,
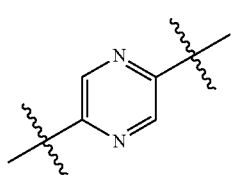, 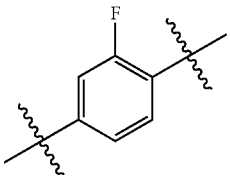,
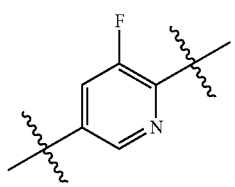,
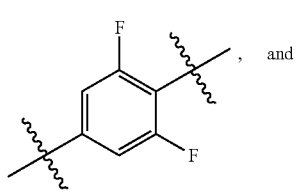, and
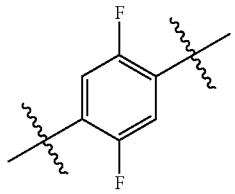.
In some embodiments,
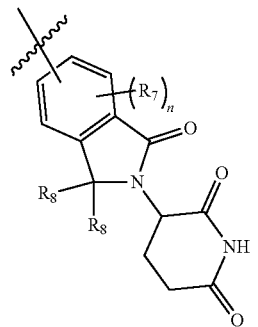
the group may be selected from
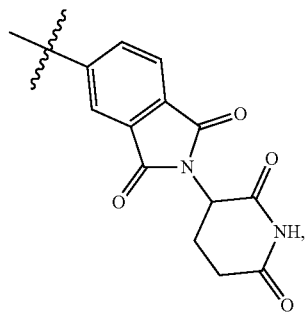
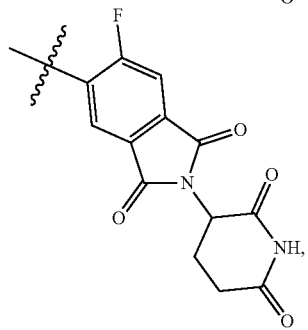
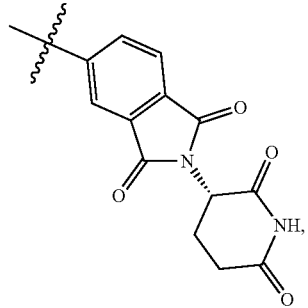
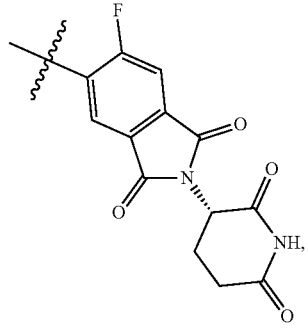

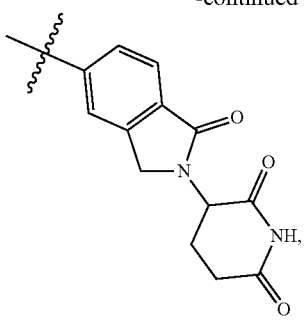
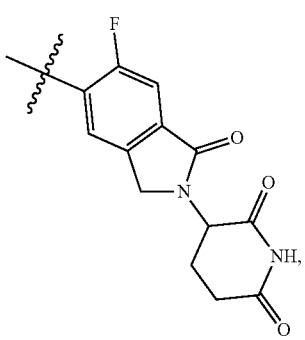
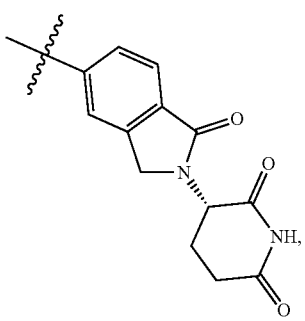
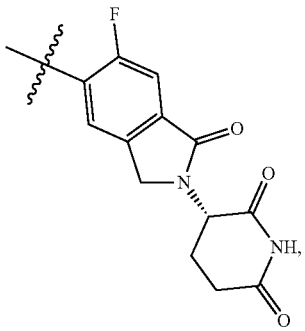
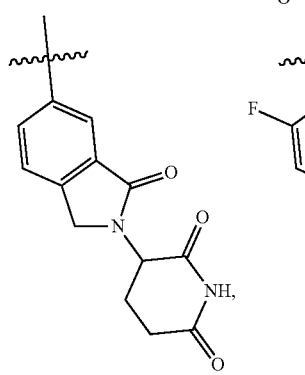
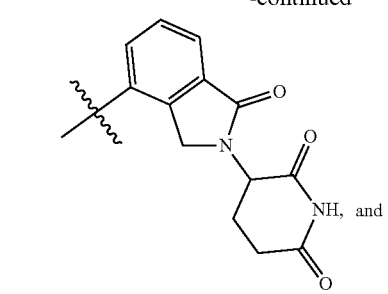
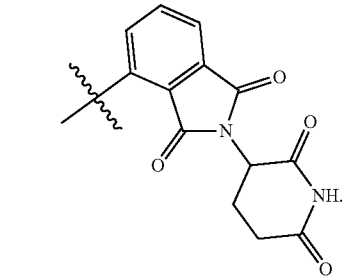 [SMILES: *c1cccc2c1C(=O)N(C1CCC(=O)NC1=O)C2=O]
In some embodiments, L may be selected from:
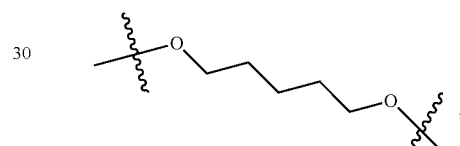
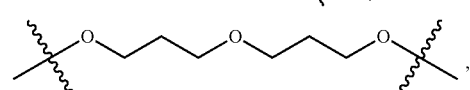
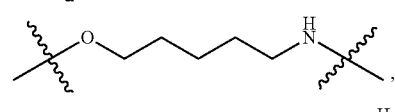
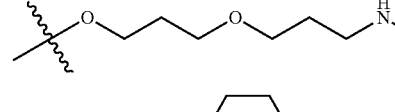
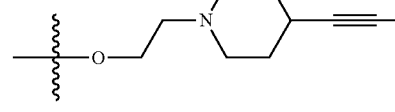
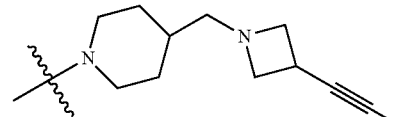
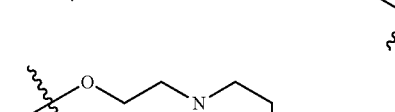
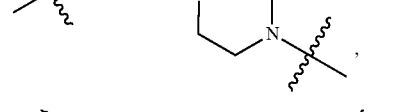

-continued

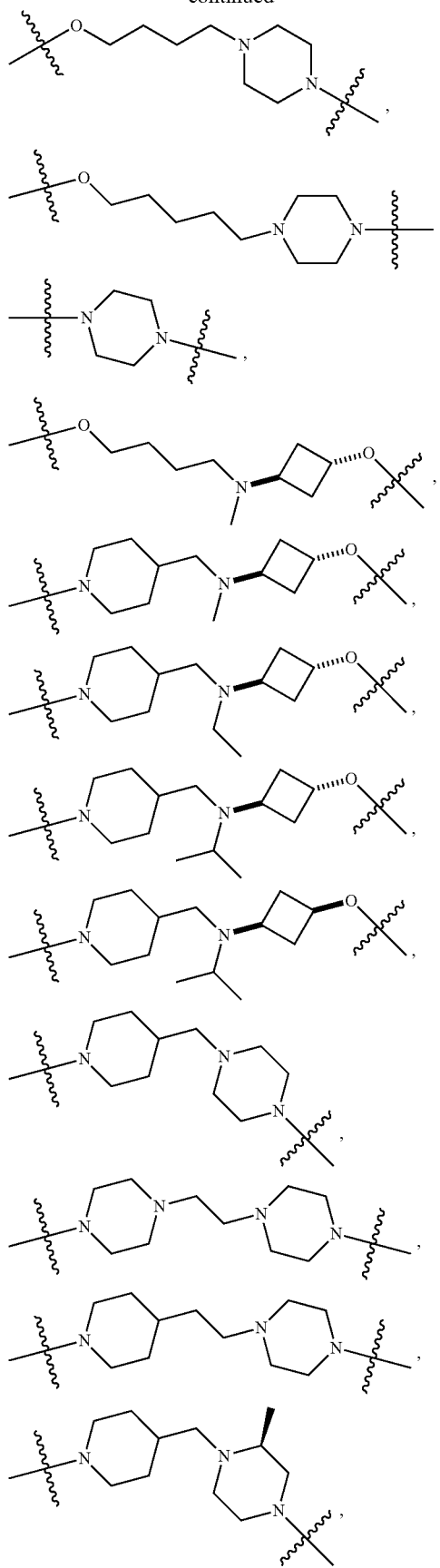

-continued

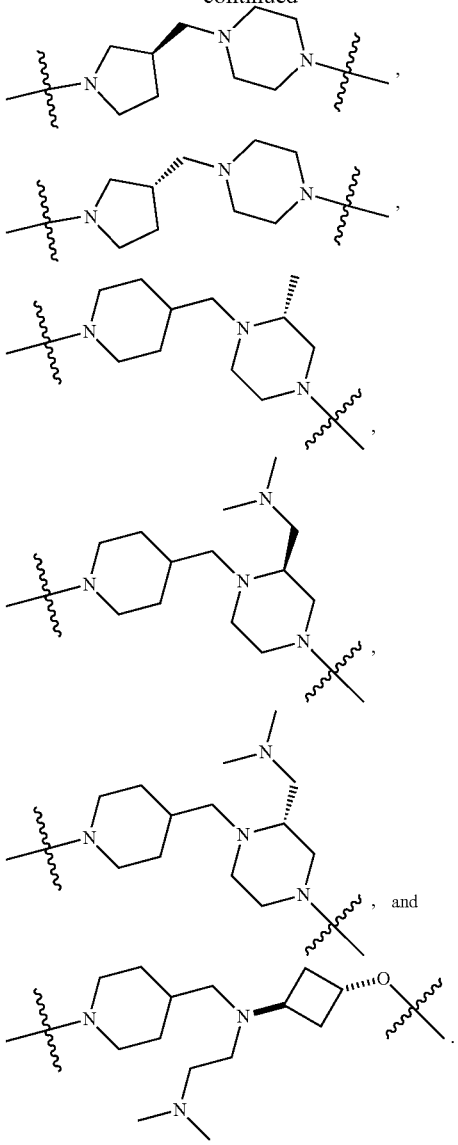

Also disclosed herein is a method of treating cancer, in a subject in need thereof, comprising administering to said subject a compound of Formula (1) (e.g. Formula (1A)) or pharmaceutically acceptable salt thereof, or a pharmaceutical composition comprising a compound of Formula (1) or a pharmaceutically acceptable salt thereof. In at least one embodiment, the pharmaceutical composition of the present disclosure may be for use in (or in the manufacture of medicaments for) the treatment of cancer in the subject in need thereof.

In at least one embodiment, a therapeutically-effective amount of a pharmaceutical composition of the present disclosure may be administered to a subject diagnosed with cancer. In some embodiments, the cancer is selected from prostate cancer, head and neck cancer, skin cancer, sarcoma, renal cell carcinoma, adrenocortical carcinoma, bladder cancer, lung cancer, gastric carcinoma, esophageal carcinoma, pancreatic adenocarcinoma, colorectal cancer, connective tissue cancer, glioblastoma multiforme, cervical cancer, uterine cancer, ovarian cancer, and breast cancer.

BRIEF DESCRIPTION OF THE FIGURES

The accompanying drawings, which are incorporated in and constitute a part of this specification, illustrate the disclosed embodiments and, together with the description, explain the principles of the disclosed embodiments. In the drawings:

FIG. 1 illustrates the androgen receptor (AR) degradative activity of compounds 3-13 and 3-29 in LNCAP cell lines 24 hours after administration using Western blot analysis.

DETAILED DESCRIPTION OF THE DISCLOSURE

Definitions

As used herein, "cancer" refers to diseases, disorders, and conditions that involve abnormal cell growth with the potential to invade or spread to other parts of the body. Exemplary cancers include, but are not limited to, prostate cancer, head and neck cancer, skin cancer, sarcoma, renal cell carcinoma, adrenocortical carcinoma, bladder cancer, lung cancer, gastric carcinoma, esophageal carcinoma, pancreatic adenocarcinoma, colorectal cancer, connective tissue cancer, glioblastoma multiforme, cervical cancer, uterine cancer, ovarian cancer, and breast cancer.

As used herein, the term "androgen receptor positive" means that androgen receptor is detected by one or more analytical methods, e.g., immunohistochemistry. For example, analysis of a biopsy of a subject's tumor may indicate the presence of androgen receptor. AR status may be tested by circulating cancer cells or circulating tumor DNA in a blood test. In some circumstances an AR test may not be performed.

"Subject" refers to an animal, such as a mammal, that has been or will be the object of treatment, observation, or experiment. The methods described herein may be useful for both human therapy and veterinary applications. In one embodiment, the subject is a human.

As used herein, "treatment" or "treating" refers to an amelioration of a disease or disorder, or at least one discernible symptom thereof. In another embodiment, "treatment" or "treating" refers to an amelioration of at least one measurable physical parameter, not necessarily discernible by the patient. In yet another embodiment, "treatment" or "treating" refers to inhibiting the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder.

A dash ("—") that is not between two letters or symbols is used to indicate a point of attachment for a substituent. For example, —CN is attached through the carbon atom.

By "optional" or "optionally" it is meant that the subsequently described event or circumstance may or may not occur, and that the description includes instances where the event or circumstance occurs and instances in which is does not. It will be understood by those skilled in the art, with respect to any group containing one or more substituents, that such groups are not intended to introduce any substitution or substitution patterns that are sterically impractical, synthetically non-feasible and/or inherently unstable.

When a range of values is listed, it is intended to encompass each value and sub-range within the range. For example, "$C_1$-$C_6$ alkyl" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "alkenyl" as used herein refers to an unsaturated, two-carbon group having a carbon-carbon double bond, referred to herein as $C_2$-alkenyl.

The term "alkoxy" as used herein refers to an alkyl or cycloalkyl covalently bonded to an oxygen atom.

The term "alkyl" as used herein refers to a saturated straight or branched hydrocarbon, such as a straight or branched group of 1-8 carbon atoms, referred to herein as ($C_1$-$C_8$)alkyl. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, and octyl. In some embodiments, "alkyl" is a straight-chain hydrocarbon. In some embodiments, "alkyl" is a branched hydrocarbon.

The term "alkynyl" as used herein refers to an unsaturated, two-carbon group having a carbon-carbon triple bond, referred to herein as $C_2$-alkynyl.

The term "aryl" as used herein refers to a mono-, bi-, or other multi-carbocyclic, aromatic ring system with 5 to 14 ring atoms. The aryl group can optionally be fused to one or more rings selected from aryls, cycloalkyls, heteroaryls, and heterocyclyls. The aryl groups of this present disclosure can be substituted with groups selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Exemplary aryl groups also include but are not limited to a monocyclic aromatic ring system, wherein the ring comprises 6 carbon atoms, referred to herein as "$C_6$-aryl."

The term "cycloalkyl" as used herein refers to a saturated or unsaturated cyclic, bicyclic, or bridged bicyclic hydrocarbon group of 3-16 carbons, or 3-8 carbons, referred to herein as "($C_3$-$C_8$)cycloalkyl," derived from a cycloalkane. Exemplary cycloalkyl groups include, but are not limited to, cyclohexanes, cyclohexenes, cyclopentanes, and cyclopentenes. Cycloalkyl groups may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Cycloalkyl groups can be fused to other cycloalkyl (saturated or partially unsaturated), aryl, or heterocyclyl groups, to form a bicycle, tetracycle, etc. The term "cycloalkyl" also includes bridged and spiro-fused cyclic structures which may or may not contain heteroatoms.

The terms "halo" or "halogen" as used herein refer to —F, —Cl, —Br, and/or —I.

The term "haloalkyl group" as used herein refers to an alkyl group substituted with one or more halogen atoms.

The term "heteroaryl" as used herein refers to a mono-, bi-, or multi-cyclic, aromatic ring system containing one or more heteroatoms, for example 1-4 heteroatoms, such as nitrogen, oxygen, and sulfur. Heteroaryls can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heteroaryls can also be fused to non-aromatic rings. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3)- and (1,2,4)-triazolyl, pyrazinyl, pyrimidilyl, tetrazolyl, furyl, thienyl, isoxazolyl, thiazolyl, furyl, phenyl, isoxazolyl, and oxazolyl. Exemplary heteroaryl groups include, but are not limited to, a monocyclic aromatic ring, wherein the ring comprises 2-5 carbon atoms and 1-3 heteroatoms, referred to herein as "($C_2$-$C_5$)heteroaryl." In some embodiments, a hetaryl contains 5 to 10 ring atoms, 1 to 4 of which are heteroatoms selected from N, O, and S. In some embodiments, a heteroaryl contains 5 to 8 ring atoms, 1 to 4 of which are heteroatoms selected from N, O, and S.

The terms "heterocycle," "heterocyclyl," or "heterocyclic" as used herein each refer to a saturated or unsaturated 3- to 18-membered ring containing one, two, three, or four heteroatoms independently selected from nitrogen, oxygen, phosphorus, and sulfur. Heterocycles can be aromatic (heteroaryls) or non-aromatic. Heterocycles can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heterocycles also include bicyclic, tricyclic, and tetracyclic groups in which any of the above heterocyclic rings is fused to one or two rings independently selected from aryls, cycloalkyls, and heterocycles. Exemplary heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolidinyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolidin-2-onyl, pyrrolinyl, pyrrolyl, quinolinyl, quinoxaloyl, tetrahydrofuryl, tetrahydroisoquinolyl, tetrahydropyranyl, tetrahydroquinolyl, tetrazolyl, thiadiazolyl, thiazolidinyl, thiazolyl, thienyl, thiomorpholinyl, thiopyranyl, and triazolyl. In some embodiments, a heterocycle contains 5 to 10 ring atoms, 1 to 4 of which are heteroatoms selected from N, O, and S. In some embodiments, a heterocycle contains 5 to 8 ring atoms, 1 to 4 of which are heteroatoms selected from N, O, and S.

The terms "hydroxy" and "hydroxyl" as used herein refer to —OH.

The term "oxo" as used herein refers to a double bond to an oxygen atom (i.e., =O). For example, when two geminal groups on a carbon atom are "taken together to form an oxo", then a carbonyl (i.e., C=O) is formed.

The term "pharmaceutically acceptable carrier" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

As used herein, the term "pharmaceutically acceptable salt" refers to a salt form of a compound of this disclosure wherein the salt is nontoxic. Pharmaceutically acceptable salts of the compounds of this disclosure include those derived from suitable inorganic and organic acids and bases. A "free base" form of a compound, for example, does not contain an ionically bonded salt.

The phrase "and pharmaceutically acceptable salts and deuterated derivatives thereof" is used interchangeably with "and pharmaceutically acceptable salts thereof and deuterated derivatives of any of the forgoing" in reference to one or more compounds or formulae of the disclosure. These phrases are intended to encompass pharmaceutically acceptable salts of any one of the referenced compounds, deuterated derivatives of any one of the referenced compounds, and pharmaceutically acceptable salts of those deuterated derivatives.

One of ordinary skill in the art would recognize that, when an amount of "a compound or a pharmaceutically acceptable salt thereof" is disclosed, the amount of the pharmaceutically acceptable salt form of the compound is the amount equivalent to the concentration of the free base of the compound. It is noted that the disclosed amounts of the compounds or their pharmaceutically acceptable salts thereof herein are based upon their free base form.

Suitable pharmaceutically acceptable salts are, for example, those disclosed in S. M. Berge, et al. *J. Pharmaceutical Sciences*, 1977, 66, 1-19. For example, Table 1 of that article provides the following pharmaceutically acceptable salts:

TABLE 1

| | | |
|---|---|---|
| Acetate | Iodide | Benzathine |
| Benzenesulfonate | Isethionate | Chloroprocaine |
| Benzoate | Lactate | Choline |
| Bicarbonate | Lactobionate | Diethanolamine |
| Bitartrate | Malate | Ethylenediamine |
| Bromide | Maleate | Meglumine |
| Calcium edetate | Mandelate | Procaine |
| Camsylate | Mesylate | Aluminum |
| Carbonate | Methylbromide | Calcium |
| Chloride | Methylnitrate | Lithium |
| Citrate | Methylsulfate | Magnesium |
| Dihydrochloride | Mucate | Potassium |
| Edetate | Napsylate | Sodium |
| Edisylate | Nitrate | Zinc |
| Estolate | Pamoate (Embonate) | |
| Esylate | Pantothenate | |
| Fumarate | Phosphate/diphosphate | |
| Gluceptate | Polygalacturonate | |
| Gluconate | Salicylate | |
| Glutamate | Stearate | |
| Glycollylarsanilate | Subacetate | |
| Hexylresorcinate | Succinate | |
| Hydrabamine | Sulfate | |
| Hydrobromide | Tannate | |
| Hydrochloride | Tartrate | |
| Hydroxynaphthoate | Teociate | |
| | Triethiodide | |

Non-limiting examples of pharmaceutically acceptable acid addition salts include: salts formed with inorganic acids, such as hydrochloric acid, hydrobromic acid, phosphoric acid, sulfuric acid, or perchloric acid; salts formed with organic acids, such as acetic acid, oxalic acid, maleic acid, tartaric acid, citric acid, succinic acid or malonic acid; and salts formed by using other methods used in the art, such as ion exchange. Non-limiting examples of pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate salts. Pharmaceutically acceptable salts derived from appropriate bases include alkali metal, alkaline earth metal, ammonium, and $N^+(C_{1-4}alkyl)_4$ salts. This disclosure also envisions the quaternization of any basic nitrogen-containing groups of the compounds disclosed herein. Suitable non-limiting examples of alkali and alkaline earth metal salts include sodium, lithium, potassium, calcium, and magnesium. Further non-limiting examples of pharmaceutically acceptable salts include ammonium, quaternary ammonium, and amine cations formed using counterions such as halide, hydroxide, carboxylate, sulfate, phosphate, nitrate, lower alkyl sulfonate and aryl sulfonate. Other suitable, non-limiting examples of pharmaceutically acceptable salts include besylate and glucosamine salts.

As used herein, nomenclature for compounds including organic compounds, can be given using common names, IUPAC, IUBMB, or CAS recommendations for nomenclature. One of skill in the art can readily ascertain the structure of a compound if given a name, either by systemic reduction of compound structure using naming conventions, or by commercially available software, such as CHEMDRAW™ (Cambridgesoft Corporation, U.S.A.).

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present disclosure encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly. In some embodiments, an enantiomer or stereoisomer may be provided substantially free of the corresponding enantiomer.

In some embodiments, the compound is a racemic mixture of (S)- and (R)-isomers. In other embodiments, provided herein is a mixture of compounds wherein individual compounds of the mixture exist predominately in an (S)- or (R)-isomeric configuration. For example, the compound mixture has an (S)-enantiomeric excess of greater than about 55%, about 60%, about 65%, about 70%, about 75%, about 80%, about 85%, about 90%, about 95%, about 96%, about 97%, about 98%, about 99%, about 99.5%, or more. In other embodiments, the compound mixture has an (S)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more. In other embodiments, the compound mixture has an (R)-enantiomeric purity of greater than about 55%, about 60%, about 65%, about 70%, about 75%, about 80%, about 85%, about 90%, about 95%, about 96%, about 97%, about 98%, about 99%, about 99.5% or more. In some other embodiments, the compound mixture has an (R)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5% or more.

Individual stereoisomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by: (1) attachment of a mixture of enantiomers to a chiral auxiliary, separation of the resulting mixture of diastereomers by recrystallization or chromatography and liberation of the optically pure product from the auxiliary; (2) salt formation employing an optically active resolving agent; or (3) direct separation of the mixture of optical enantiomers on chiral chromatographic columns. Stereoisomeric mixtures can also be resolved into their component stereoisomers by well-known methods, such as chiral-phase gas chromatography, chiral-phase high performance liquid chromatography, crystallizing the compound as a chiral salt complex, or crystallizing the compound in a chiral solvent. Stereoisomers can also be obtained from stereomerically-pure intermediates, reagents, and catalysts by well-known asymmetric synthetic methods.

Geometric isomers can also exist in the compounds of the present disclosure. The present disclosure encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the E and Z isomers.

Substituents around a carbon-carbon double bond alternatively can be referred to as "cis" or "trans," where "cis" represents substituents on the same side of the double bond and "trans" represents substituents on opposite sides of the double bond. The arrangements of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The compounds disclosed herein may exist as tautomers and both tautomeric forms are intended to be encompassed by the scope of the present disclosure, even if only one tautomeric structure is depicted.

Additionally, unless otherwise stated, structures described herein are also meant to include compounds that differ only in the presence of one or more isotopically enriched atoms.

For example, compounds having the present structures except for the replacement of hydrogen by deuterium ($^2$H) or tritium ($^3$H), or the replacement of a carbon by a $^{13}$C- or $^{14}$C-carbon atom are within the scope of this disclosure. Such compounds may be useful as, for example, analytical tools, probes in biological assays, or therapeutic agents.

Compounds

In some embodiments, provided herein are compounds of Formula (1), or a tautomer, stereoisomer, or pharmaceutically acceptable salt thereof, and deuterated derivatives of any of the foregoing:

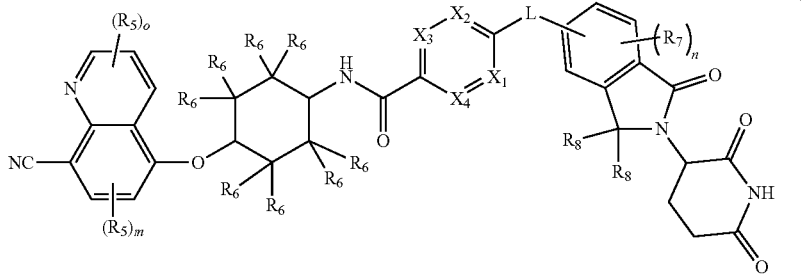

(1)

wherein:

$X_1$ is $CR_1$ or N;

$X_2$ is $CR_2$ or N;

$X_3$ is $CR_3$ or N;

$X_4$ is $CR_4$ or N;

each of $R_1$, $R_2$, $R_3$, and $R_4$ is independently selected from hydrogen, halogen, $C_1$-$C_3$alkoxy, and $C_1$-$C_3$haloalkyl, each of which is substituted with 0, 1, 2, or 3 $R_S$;

each $R_5$ is independently selected from halogen, hydroxyl, $C_1$-$C_3$alkyl, $C_1$-$C_3$alkoxy, $C_1$-$C_3$haloalkyl, —N($R_9$)$_2$, and —CN, each of which is substituted with 0, 1, 2, or 3 $R_S$;

each $R_6$ is independently selected from hydrogen, halogen, $C_1$-$C_3$alkyl, and $C_1$-$C_3$haloalkyl, each of which is substituted with 0, 1, 2, or 3 $R_S$, or two $R_6$ groups are taken together to form an oxo;

each $R_7$ is independently selected from halogen, hydroxyl, $C_1$-$C_3$alkyl, $C_1$-$C_3$alkoxy, $C_1$-$C_3$haloalkyl, —N($R_9$)$_2$, and —CN, each of which is substituted with 0, 1, 2, or 3 $R_S$;

each $R_8$ is independently selected from hydrogen, hydroxyl, $C_1$-$C_3$alkyl, and $C_1$-$C_3$haloalkyl, each of which is substituted with 0, 1, 2, or 3 $R_S$, or two $R_8$ groups are taken together to form an oxo;

each $R_9$ is independently selected from hydrogen, $C_1$-$C_3$alkyl, —C(=O)—($C_1$-$C_3$alkyl), —C(=O)—O—($C_1$-$C_3$alkyl), and —C(=O)—NH—($C_1$-$C_3$alkyl), each of which is substituted with 0, 1, 2, or 3 $R_S$, or two $R_9$ groups are taken together to form a 3- to 6-membered heterocycle or heteroaryl;

each $R_S$ is independently selected from halogen, hydroxyl, $C_1$-$C_3$alkyl, $C_1$-$C_3$alkoxy, $C_1$-$C_3$haloalkyl, —N($R_9$)$_2$, and —CN;

L is a linker of 1 to 16 carbon atoms in length, wherein one or more carbon atoms are optionally replaced by C(O), O, N($R_9$), S, $C_2$-alkenyl, $C_2$-alkynyl, cycloalkyl, aryl, heterocycle, or heteroaryl, wherein the $R_9$, $C_2$-alkenyl, cycloalkyl, aryl, heterocycle, and heteroaryl are each independently substituted with 0, 1, 2, or 3 $R_S$;

m is 0, 1, or 2;

n is 0, 1, 2, or 3; and o is 0, 1, 2, or 3, wherein each hydrogen atom is independently and optionally replaced by a deuterium atom.

In some embodiments, the compound of Formula (1) may be a compound of Formula (1A)

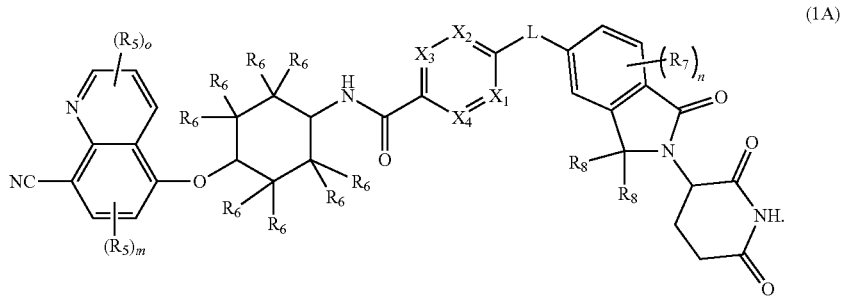

(1A)

In some embodiments, $X_1$ is N. In some embodiments, $X_2$ is N. In some embodiments, $X_1$ and $X_2$ are each N. In some embodiments, $X_2$ is $CR_2$, $X_3$ is $CR_3$, and $X_4$ is $CR_4$. In some embodiments, $R_2$, $R_3$, and $R_4$ are each independently selected from H and F. In some embodiments, $X_2$ is $CR_2$, $X_3$ is $CR_3$, $X_4$ is $CR_4$, and $R_2$, $R_3$, and $R_4$ are each independently selected from H and F. In some embodiments, $X_1$ is $CR_1$, $X_2$ is $CR_2$, $X_3$ is $CR_3$, and $X_4$ is $CR_4$. In some embodiments, $R_1$, $R_2$, $R_3$, and $R_4$ are each independently selected from H and F. In some embodiments, $X_1$ is $CR_1$, $X_2$ is $CR_2$, $X_3$ is $CR_3$, and $X_4$ is $CR_4$, and $R_1$, $R_2$, $R_3$, and $R_4$ are each independently selected from H and F.

In some embodiments, R$_1$ is F. In some embodiments, R$_2$ is F. In some embodiments, R$_3$ is F. In some embodiments, R$_4$ is F. In some embodiments, R$_1$ and R$_3$ are each F. In some embodiments, R$_3$ and R$_4$ are each F. In some embodiments, R$_2$, R$_3$, and R$_4$ are each H. In some embodiments, R$_1$, R$_3$, and R$_4$ are each H. In some embodiments, R$_1$, R$_2$, and R$_4$ are each H. In some embodiments, R$_1$, R$_2$, and R$_3$ are each H. In some embodiments, R$_2$ and R$_4$ are each H. In some embodiments, R$_1$ and R$_2$ are each H.

In some embodiments, the

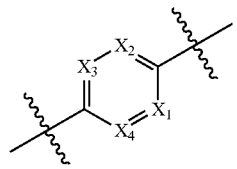

group is selected from

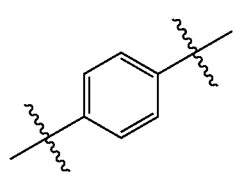 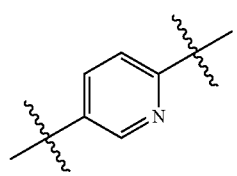

, and

In some embodiments, the

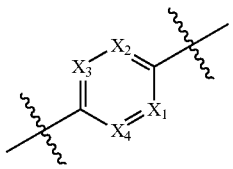

group is

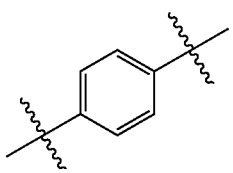

In some embodiments, the

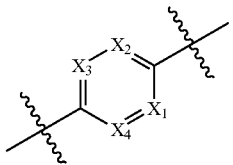

group is

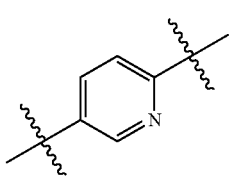

In some embodiments, the

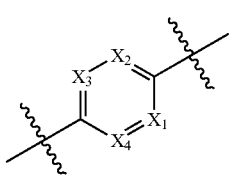

group is

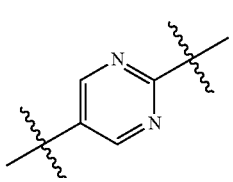

In some embodiments, the

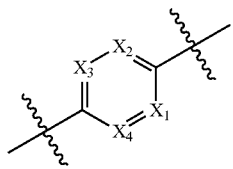

group is

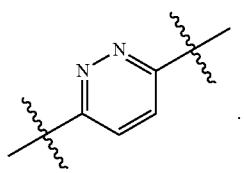

In some embodiments, the

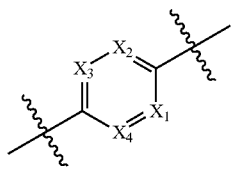

group is

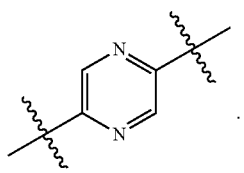

In some embodiments, the

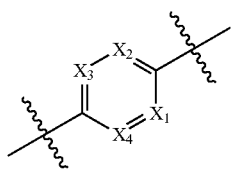

group is

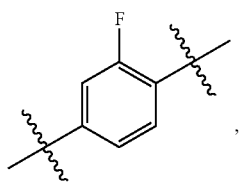 [SMILES: *c1cnc(*)c(F)c1]

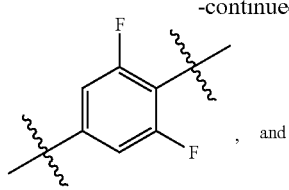

, and

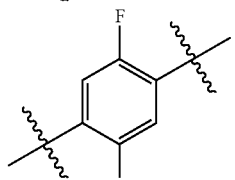

In some embodiments, the

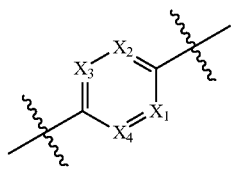

group is

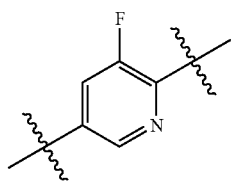

In some embodiments, each $R_5$ is independently selected from halogen, $C_1$-$C_3$alkoxy, and $C_1$-$C_3$haloalkyl. In some embodiments, each $R_5$ is independently selected from —Cl, —OCH$_3$, and —CF$_3$.

In some embodiments, m is 0 or 1. In some embodiments, m is 0. In some embodiments, m is 1.

In some embodiments, o is 0 or 1. In some embodiments, o is 0. In some embodiments, o is 1.

In some embodiments, m and o are each 0.

In some embodiments, each $R_6$ is independently selected from H and $C_1$-$C_3$alkyl. In some embodiments, each $R_6$ is independently selected from H and —CH$_3$. In some embodiments, one $R_6$ is H and the other $R_6$ is —CH$_3$. In some embodiments, each $R_6$ is identical. In some embodiments, each $R_6$ is different.

In some embodiments, each

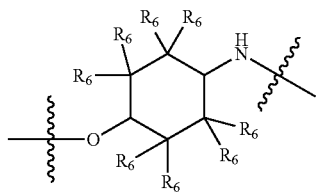

group is selected from
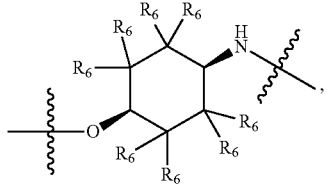,
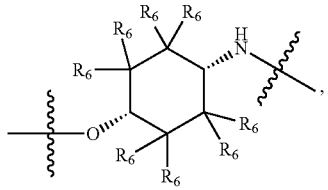,
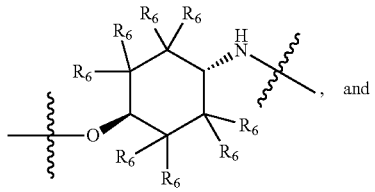, and
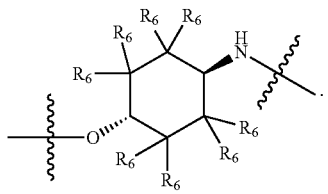.
In some embodiments, the group
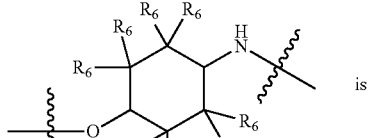 is
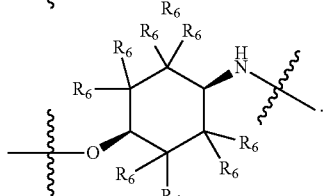.
In some embodiments, the group
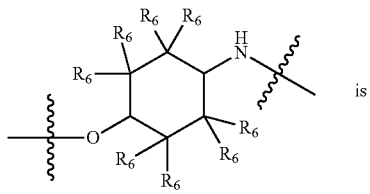 is
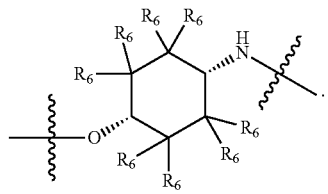.
In some embodiments, the group
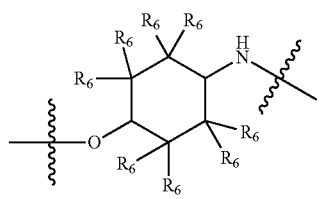 is
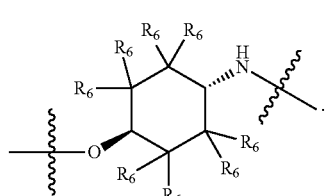.
In some embodiments, the group
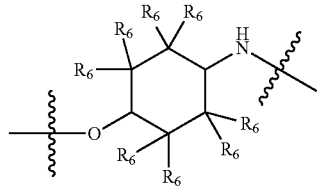 is
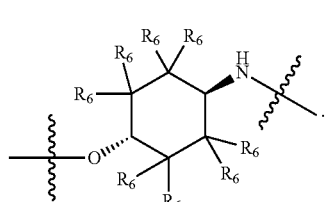.
In some embodiments, the group
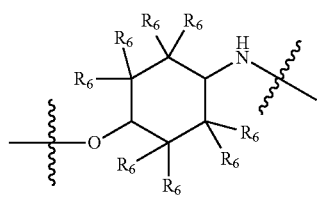

is selected from
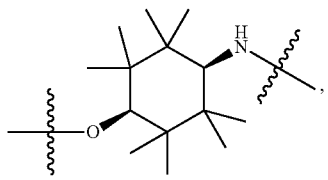,
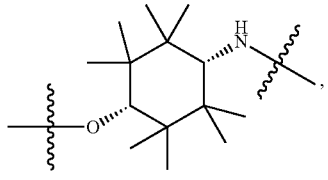,
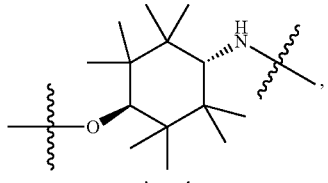,
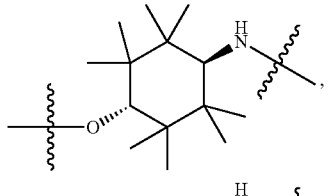,
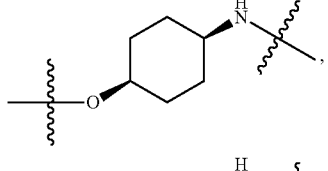,
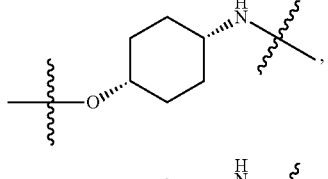,
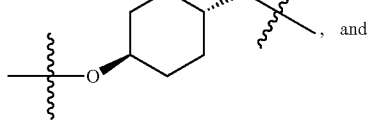, and
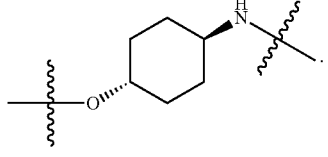.
In some embodiments, the group
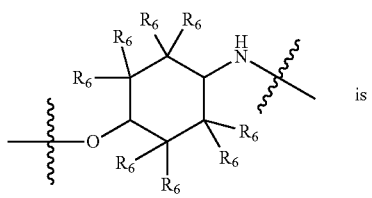 is
-continued
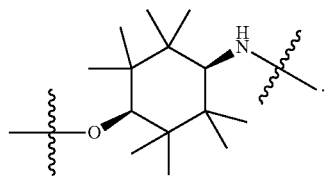.
In some embodiments, the group
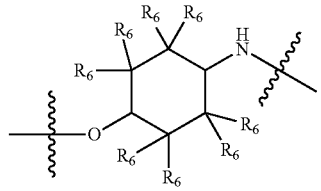 is
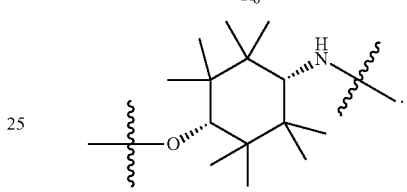.
In some embodiments, the group
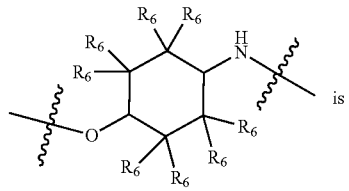 is
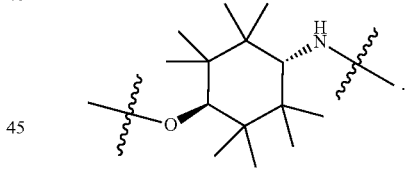.
In some embodiments, the group
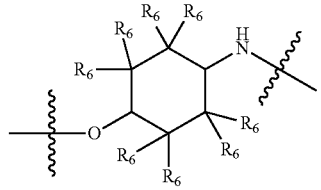 is
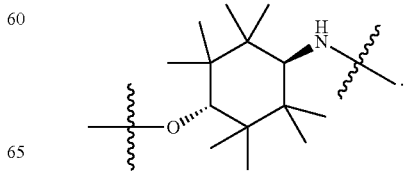.

In some embodiments, the group

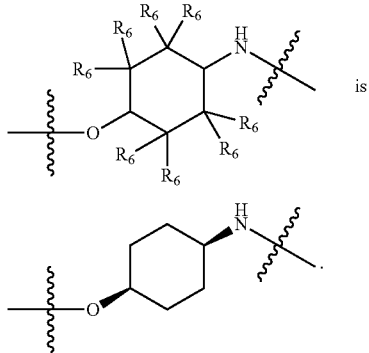 is

In some embodiments, the group

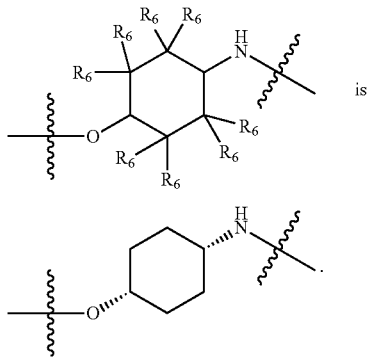 is

In some embodiments, the group

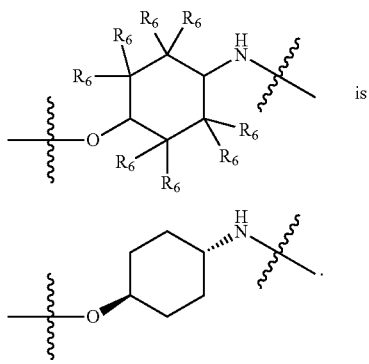 is

In some embodiments, the group

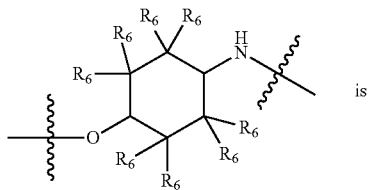 is

-continued

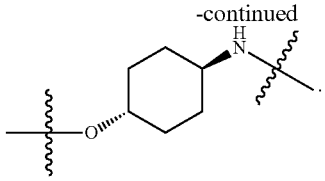

In some embodiments, each $R_7$ is independently selected from halogen, hydroxyl, $C_1$-$C_3$alkyl, and $C_1$-$C_3$haloalkyl. In some embodiments, each $R_7$ is independently selected from halogen, hydroxyl, —$CH_3$, and —$CF_3$. In some embodiments, each $R_7$ is independently selected from F, hydroxyl, —$CH_3$, and —$CF_3$. In some embodiments, each $R_7$ is independently F.

In some embodiments, n is 0. In some embodiments, n is 1.

In some embodiments, each $R_8$ is hydrogen or two $R_8$ groups are taken together to form an oxo. In some embodiments, each $R_8$ is hydrogen. In some embodiments, two $R_8$ groups are taken together to form an oxo.

In some embodiments, the

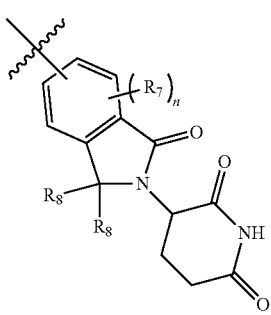

group is

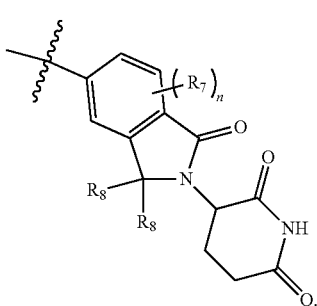

In some embodiments, the

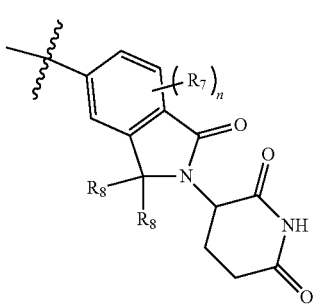

group is selected from
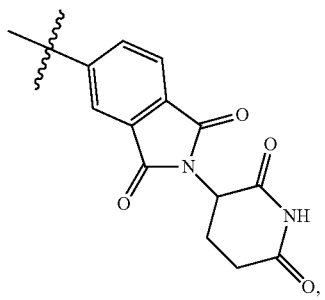
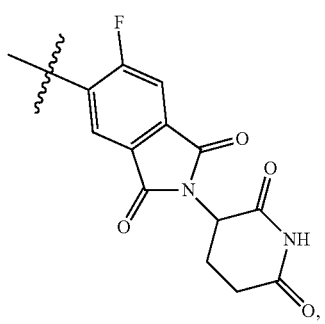
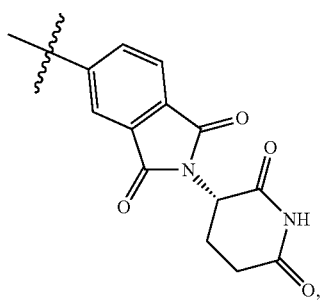
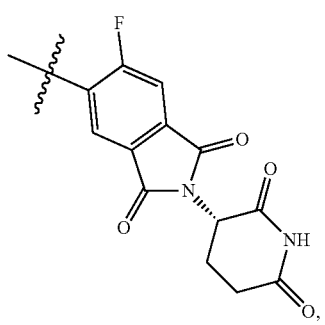
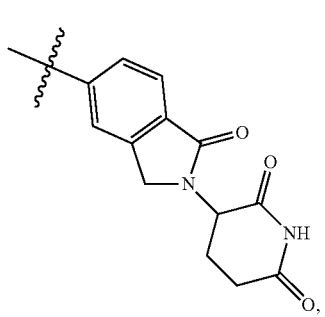
-continued
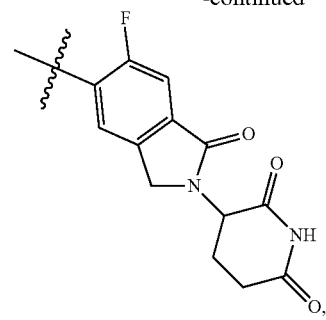
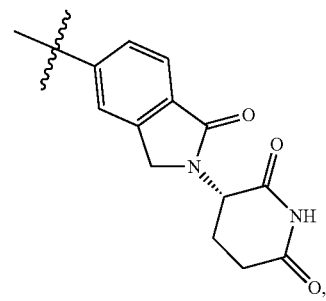
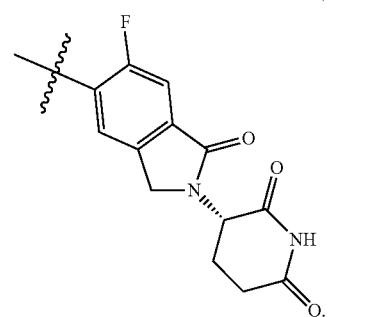, and
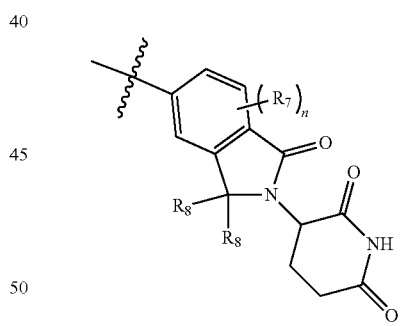.
In some embodiments, the
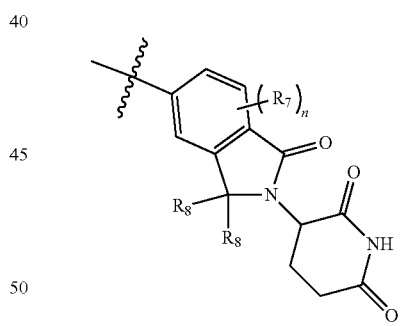
group is
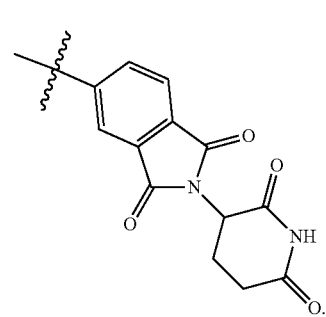 [SMILES: *c1ccc2c(c1)C(=O)N(C1CCC(=O)NC1=O)C2=O].

In some embodiments, the
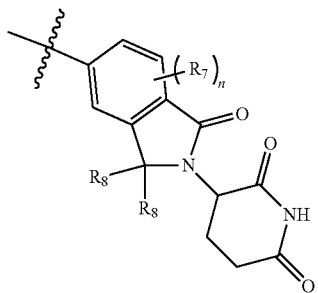
group is
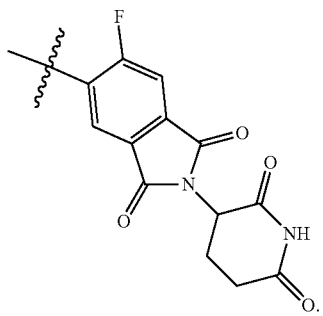 [SMILES: *c1cc2c(cc1F)C(=O)N(C1CCC(=O)NC1=O)C2=O]
In some embodiments,
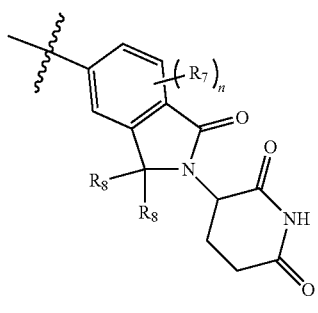
the group is
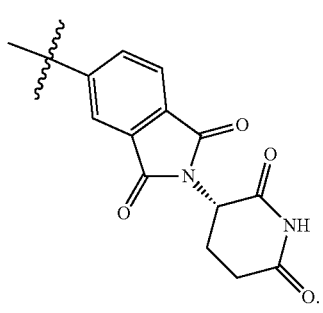 [SMILES: *c1ccc2c(c1)C(=O)N([C@H]1CCC(=O)NC1=O)C2=O]
In some embodiments, the
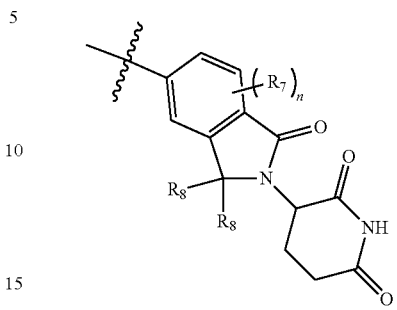
group is
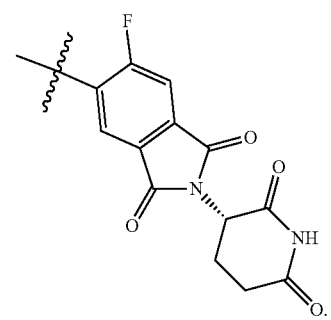 [SMILES: *c1cc2c(cc1F)C(=O)N([C@H]1CCC(=O)NC1=O)C2=O]
In some embodiments, the
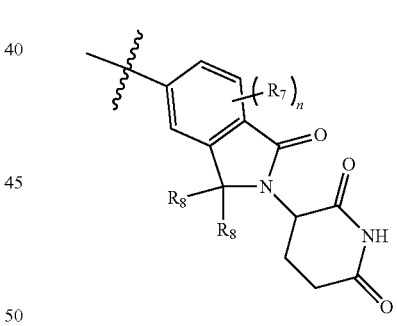
group is
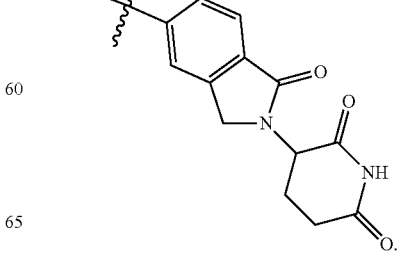

In some embodiments, the
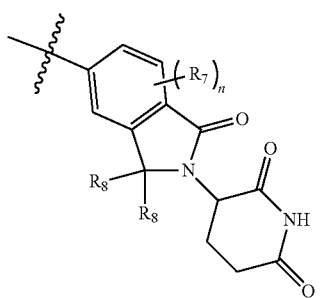
group is
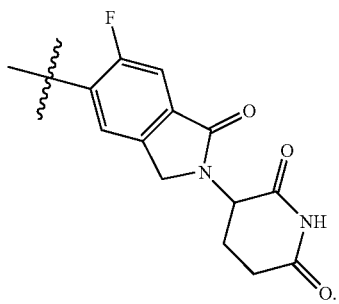 [SMILES: *c1cc2c(cc1F)C(=O)N(C1CCC(=O)NC1=O)C2]
In some embodiments, the
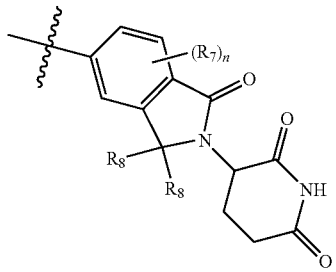
group is
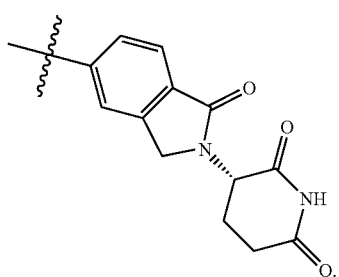 [SMILES: *c1ccc2c(c1)CN([C@H]1CCC(=O)NC1=O)C2=O]
In some embodiments, the
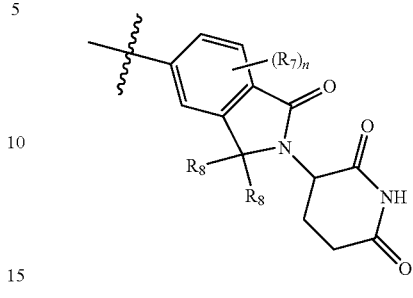
group is
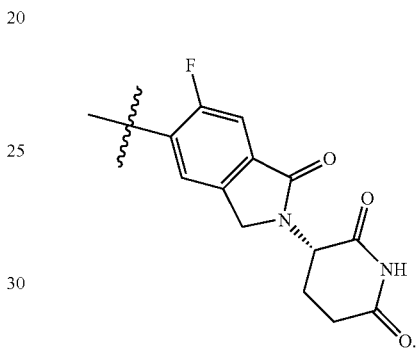
In some embodiments, In some embodiments, the
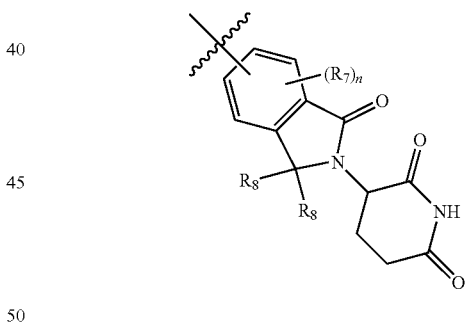
group is
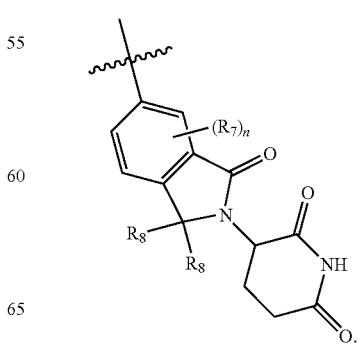

In some embodiments, the
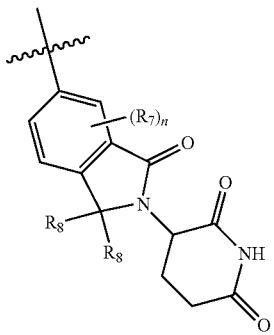
group is
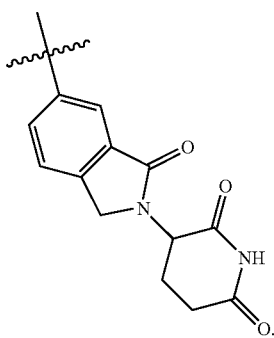 [SMILES: *c1ccc2c(c1)C(=O)N(C1CCC(=O)NC1=O)C2]
In some embodiments, the
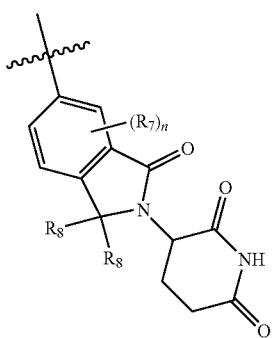
group is
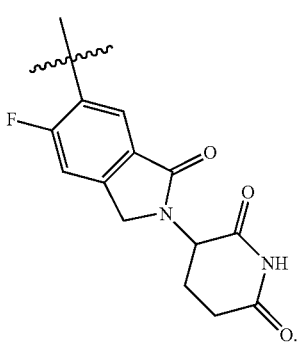 [SMILES: *c1cc2c(cc1F)CN(C1CCC(=O)NC1=O)C2=O]
In some embodiments, the
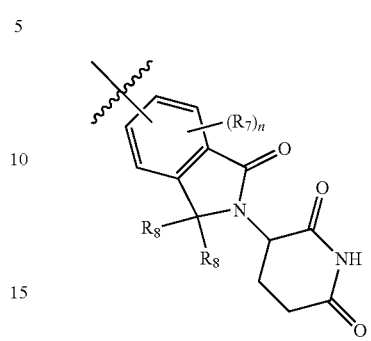
group is
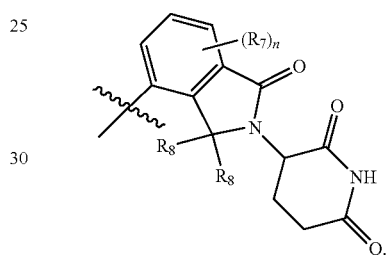
In some embodiments, the
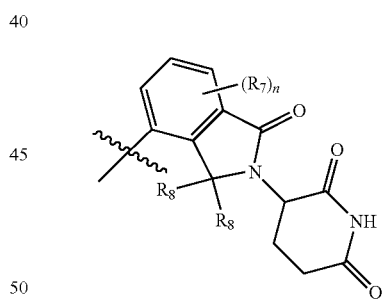
group is
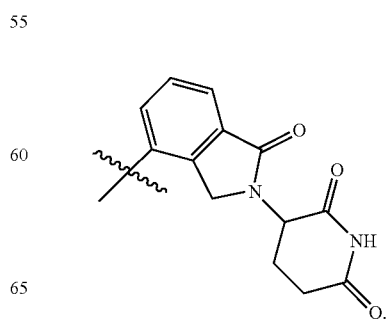

In some embodiments, the

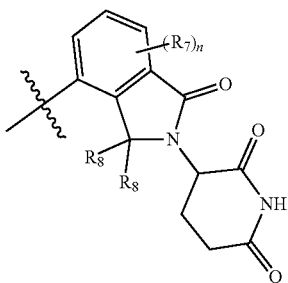

group is

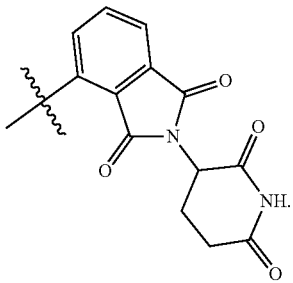 [SMILES: *c1cccc2c1C(=O)N(C1CCC(=O)NC1=O)C2=O]

In some embodiments, each $R_9$ is independently selected from hydrogen, $C_1$-$C_3$alkyl, and —C(=O)—$C_1$-$C_3$alkyl. In some embodiments, each $R_9$ is independently selected from hydrogen and $C_1$-$C_3$alkyl. In some embodiments, each $R_9$ is independently selected from hydrogen, —$CH_3$, —$CH_2CH_3$, and —$CH(CH_3)_2$.

In some embodiments, L is a linker of 1 to 12 carbon atoms in length, wherein one or more carbon atoms are optionally replaced by C(=O), O, N($R_9$), S, $C_2$-alkenyl, $C_2$-alkynyl, cycloalkyl, aryl, heterocycle, or heteroaryl, wherein the $R_9$, $C_2$-alkenyl, cycloalkyl, aryl, heterocycle, and heteroaryl are each independently substituted with 0, 1, 2, or 3 $R_S$. In some embodiments, L is a linker of 1 to 10 carbon atoms in length, wherein one or more carbon atoms are optionally replaced by C(=O), O, N($R_9$), S, $C_2$-alkenyl, $C_2$-alkynyl, cycloalkyl, aryl, heterocycle, or heteroaryl, wherein the $R_9$, $C_2$-alkenyl, cycloalkyl, aryl, heterocycle, and heteroaryl are each independently substituted with 0, 1, 2, or 3 $R_S$. In some embodiments, L is a linker of 1 to 8 carbon atoms in length, wherein one or more carbon atoms are optionally replaced by C(=O), O, N($R_9$), S, $C_2$-alkenyl, $C_2$-alkynyl, cycloalkyl, aryl, heterocycle, or heteroaryl, wherein the $R_9$, $C_2$-alkenyl, cycloalkyl, aryl, heterocycle, and heteroaryl are each independently substituted with 0, 1, 2, or 3 $R_S$. In some embodiments, L is a linker of 1 to 6 carbon atoms in length, wherein one or more carbon atoms are optionally replaced by C(=O), O, N($R_9$), S, $C_2$-alkenyl, $C_2$-alkynyl, cycloalkyl, aryl, heterocycle, or heteroaryl, wherein the $R_9$, $C_2$-alkenyl, cycloalkyl, aryl, heterocycle, and heteroaryl are each independently substituted with 0, 1, 2, or 3 $R_S$.

In some embodiments, one or more carbon atoms of linker L are optionally replaced by C(=O), O, N($R_9$), S, cycloalkyl, aryl, heterocycle, or heteroaryl. In some embodiments, one or more carbon atoms of linker L are optionally replaced by O, N($R_9$), cycloalkyl, or heterocycle, wherein the $R_9$, cycloalkyl, and heterocycle are each independently substituted with 0, 1, 2, or 3 $R_S$. In some embodiments, at least one carbon atom of linker L is replaced by a heterocycle, which is substituted with 0, 1, 2, or 3 $R_S$. In some embodiments, at least two carbon atoms of linker L are replaced by a heterocycle, each of which is substituted with 0, 1, 2, or 3 $R_S$.

In some embodiments, the heterocycle in L is selected from piperidine and piperazine, each of which is substituted with 0, 1, 2, or 3 $R_S$. In some embodiments, the heterocycle in L is selected from

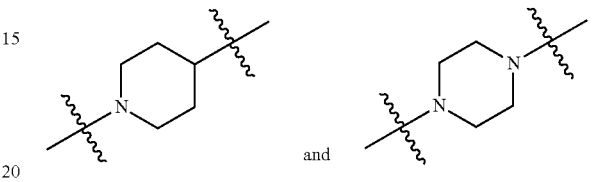

and

In some embodiments, L is selected from:

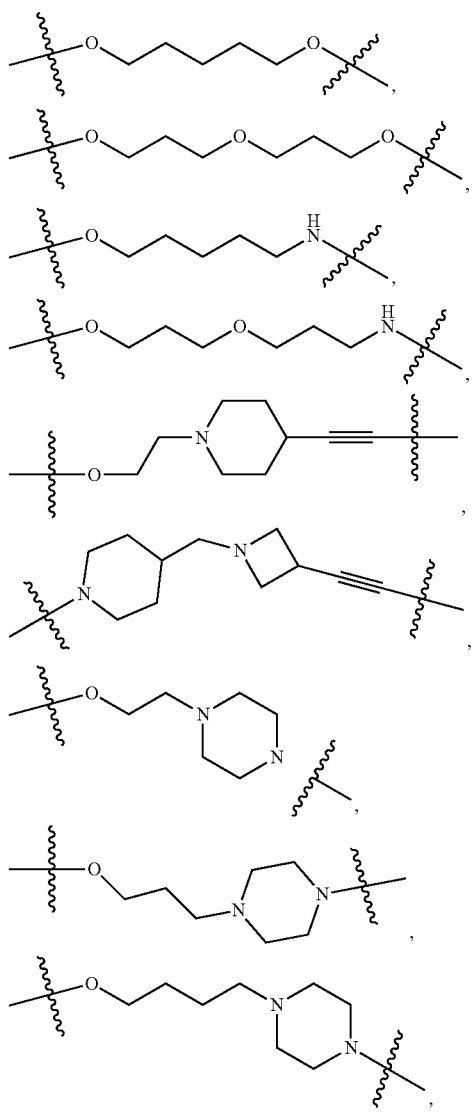

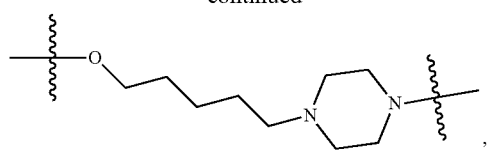

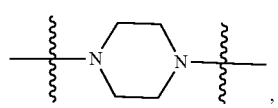

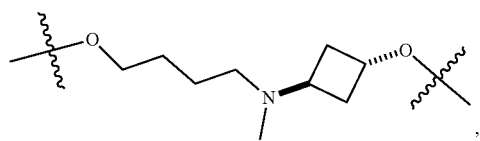

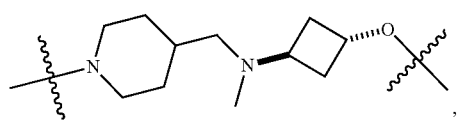

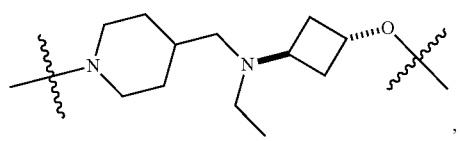

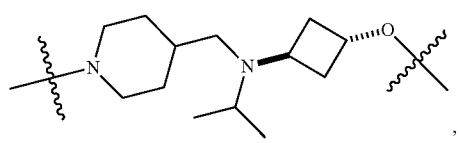

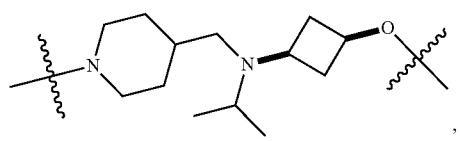

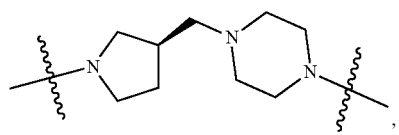

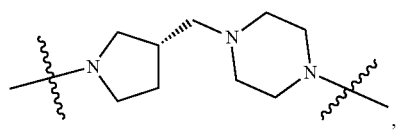

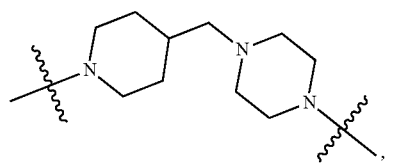

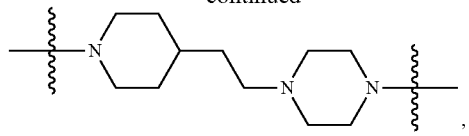

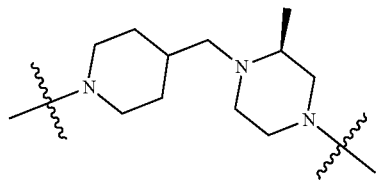

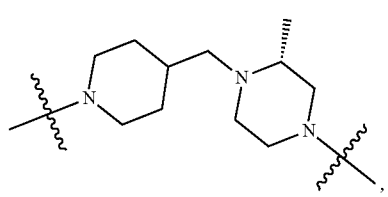

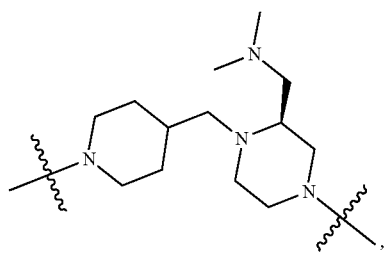

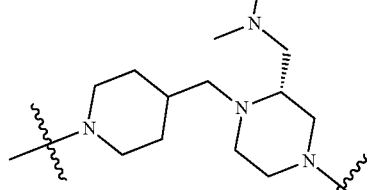

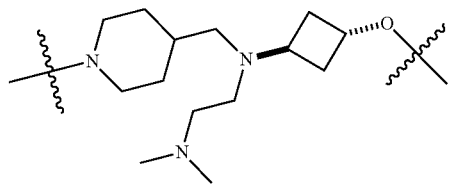

, and

In some embodiments, provided herein is a pharmaceutically acceptable salt of a compound of Formula (1). In some embodiments, provided herein is a deuterated derivative of a pharmaceutically acceptable salt of a compound of Formula (1). In some embodiments, provided herein is a compound of Formula (1). In some embodiments, provided herein is a compound of Formula (1A).

In some embodiments, provided herein is a compound chosen from the compounds listed in Table 2 or a tautomer, stereoisomer, or pharmaceutically acceptable salt thereof, or a deuterated derivative of any of the foregoing.

TABLE 2

Exemplary Compounds of the Present Disclosure

| # | Structure & Name | Reference Number |
|---|---|---|
| 1 | 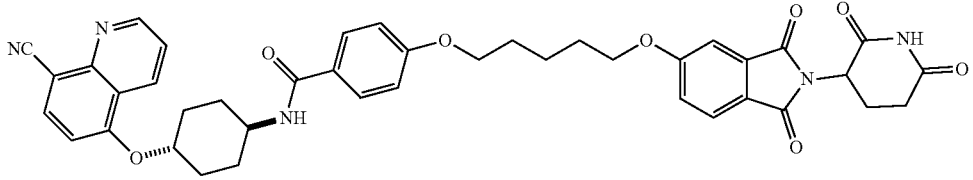<br>N-((1r,4r)-4-((8-cyanoquinolin-5-yl)oxy)cyclohexyl)-4-((5-((2-(2,6-dioxopiperidin-3-yl)-1,3-dioxoisoindolin-5-yl)oxy)pentyl)oxy)benzamide | 3-1 |
| 2 | 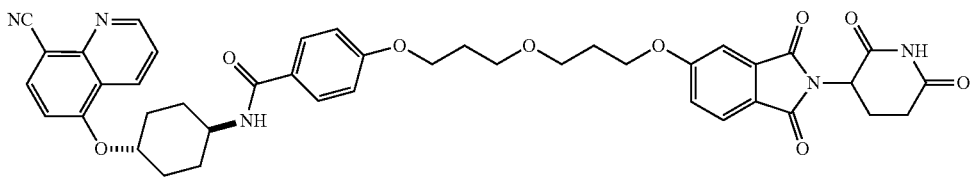<br>N-((1r,4r)-4-((8-cyanoquinolin-5-yl)oxy)cyclohexyl)-4-(3-(3-((2-(2,6-dioxopiperidin-3-yl)-1,3-dioxoisoindolin-5-yl)oxy)propoxy)propoxy)benzamide | 3-2 |
| 3 | 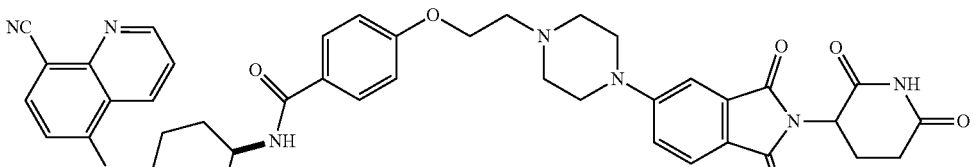<br>N-((1r,4r)-4-((8-cyanoquinolin-5-yl)oxy)cyclohexyl)-4-(2-(4-(2-(2,6-dioxopiperidin-3-yl)-1,3-dioxoisoindolin-5-yl)piperazin-1-yl)ethoxy)benzamide | 3-3 |
| 4 | <br>N-((1r,4r)-4-((8-cyanoquinolin-5-yl)oxy)cyclohexyl)-4-(3-(4-(2-(2,6-dioxopiperidin-3-yl)-1,3-dioxoisoindolin-5-yl)piperazin-1-yl)propoxy)benzamide | 3-4 |
| 5 | 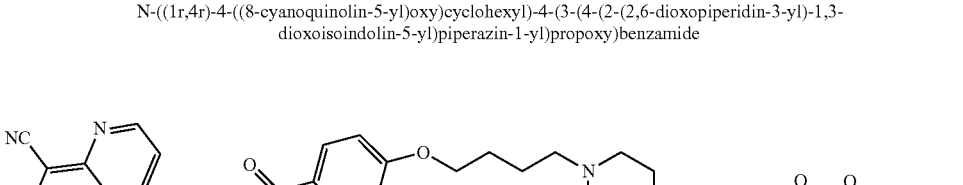<br>N-((1r,4r)-4-((8-cyanoquinolin-5-yl)oxy)cyclohexyl)-4-(4-(4-(2-(2,6-dioxopiperidin-3-yl)-1,3-dioxoisoindolin-5-yl)piperazin-1-yl)butoxy)benzamide | 3-5 |

TABLE 2-continued

Exemplary Compounds of the Present Disclosure

| # | Structure & Name | Reference Number |
|---|---|---|
| 6 | 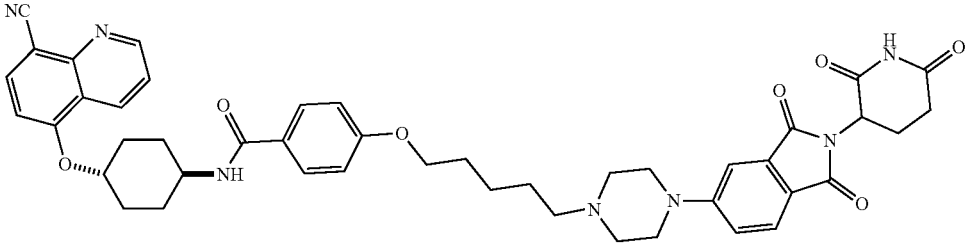<br>N-((1r,4r)-4-((8-cyanoquinolin-5-yl)oxy)cyclohexyl)-4-((5-(4-(2-(2,6-dioxopiperidin-3-yl)-1,3-dioxoisoindolin-5-yl)piperazin-1-yl)pentyl)oxy)benzamide | 3-6 |
| 7 | 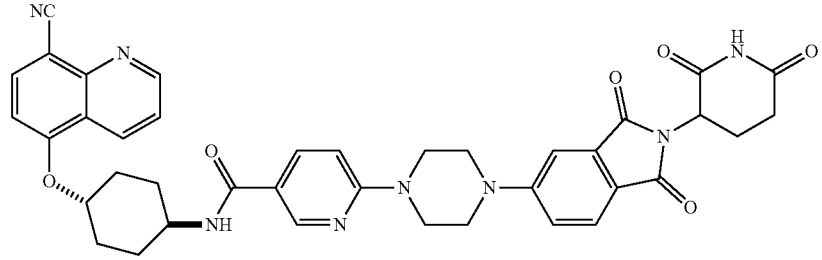<br>N-((1r,4r)-4-((8-cyanoquinolin-5-yl)oxy)cyclohexyl)-6-(4-(2-(2,6-dioxopiperidin-3-yl)-1,3-dioxoisoindolin-5-yl)piperazin-1-yl)nicotinamide | 3-7 |
| 8 | 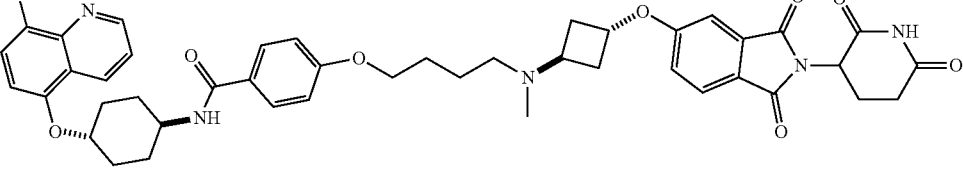<br>N-((1r,4r)-4-((8-cyanoquinolin-5-yl)oxy)cyclohexyl)-4-(4-(((1r,3r)-3-((2-(2,6-dioxopiperidin-3-yl)-1,3-dioxoisoindolin-5-yl)oxy)cyclobutyl)(methyl)amino)butoxy)benzamide | 3-8 |
| 9 | 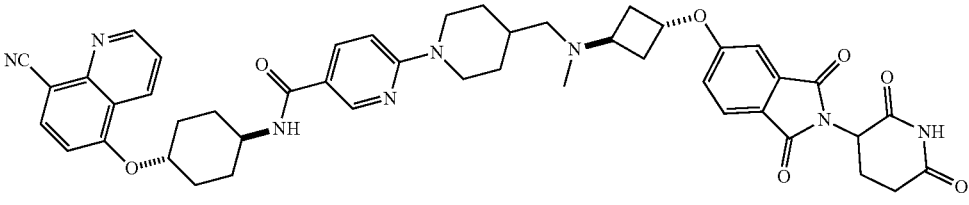<br>N-((1r,4r)-4-((8-cyanoquinolin-5-yl)oxy)cyclohexyl)-6-(4-((((1r,3r)-3-((2-(2,6-dioxopiperidin-3-yl)-1,3-dioxoisoindolin-5-yl)oxy)cyclobutyl)(methyl)amino)methyl)piperidin-1-yl)nicotinamide | 3-9 |
| 10 | 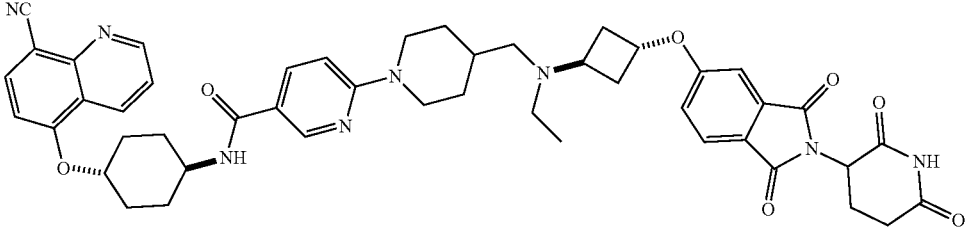<br>N-((1r,4r)-4-((8-cyanoquinolin-5-yl)oxy)cyclohexyl)-6-(4-((((1r,3r)-3-((2-(2,6-dioxopiperidin-3-yl)-1,3-dioxoisoindolin-5-yl)oxy)cyclobutyl)(ethyl)amino)methyl)piperidin-1-yl)nicotinamide | 3-10 |

TABLE 2-continued

Exemplary Compounds of the Present Disclosure

| # | Structure & Name | Reference Number |
|---|---|---|
| 11 | 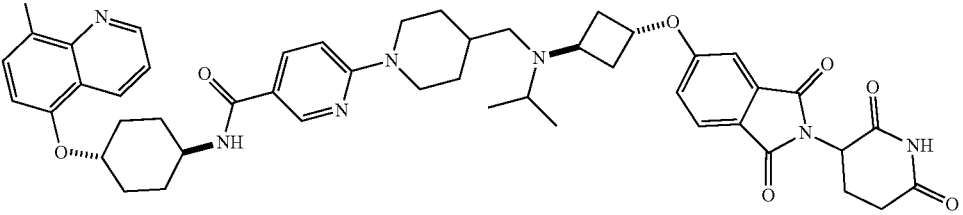<br>N-((1r,4r)-4-((8-cyanoquinolin-5-yl)oxy)cyclohexyl)-6-(4-(((((1r,3r)-3-((2-(2,6-dioxopiperidin-3-yl)-1,3-dioxoisoindolin-5-yl)oxy)cyclobutyl)(isopropyl)amino)methyl)piperidin-1-yl)nicotinamide | 3-11 |
| 12 | 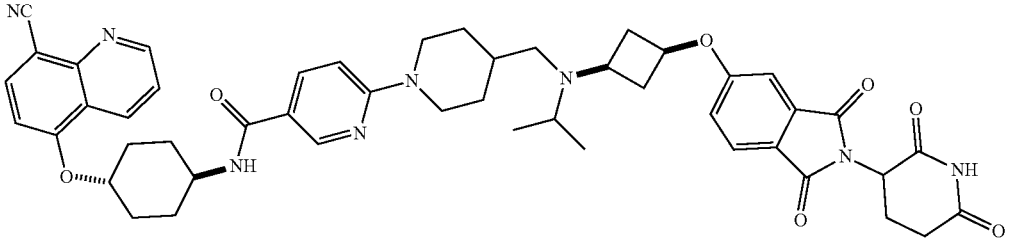<br>N-((1r,4r)-4-((8-cyanoquinolin-5-yl)oxy)cyclohexyl)-6-(4-(((((1s,3s)-3-((2-(2,6-dioxopiperidin-3-yl)-1,3-dioxoisoindolin-5-yl)oxy)cyclobutyl)(isopropyl)amino)methyl)piperidin-1-yl)nicotinamide | 3-12 |
| 13 | 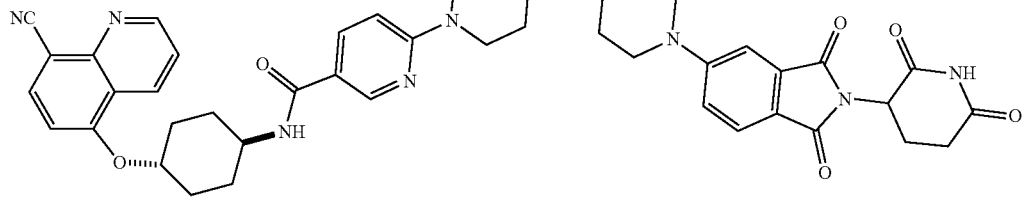<br>N-((1r,4r)-4-((8-cyanoquinolin-5-yl)oxy)cyclohexyl)-6-(4-((4-(2-(2,6-dioxopiperidin-3-yl)-1,3-dioxoisoindolin-5-yl)piperazin-1-yl)methyl)piperidin-1-yl)nicotinamide | 3-13 |
| 14 | 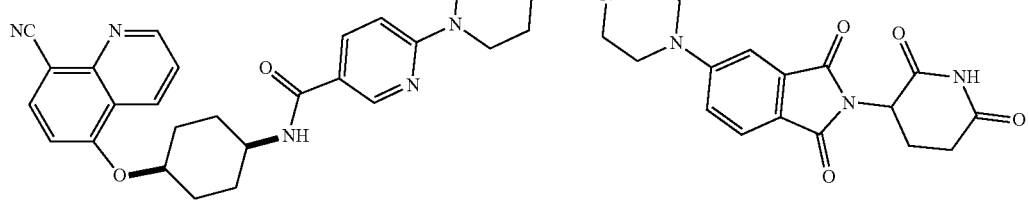<br>N-((1s,4s)-4-((8-cyanoquinolin-5-yl)oxy)cyclohexyl)-6-(4-((4-(2-(2,6-dioxopiperidin-3-yl)-1,3-dioxoisoindolin-5-yl)piperazin-1-yl)methyl)piperidin-1-yl)nicotinamide | 3-14 |

TABLE 2-continued

Exemplary Compounds of the Present Disclosure

| # | Structure & Name | Reference Number |
|---|---|---|
| 15 | N-((1r,4r)-4-((8-cyanoquinolin-5-yl)oxy)cyclohexyl)-2-(4-((4-(2-(2,6-dioxopiperidin-3-yl)-1,3-dioxoisoindolin-5-yl)piperazin-1-yl)methyl)piperidin-1-yl)pyrimidine-5-carboxamide | 3-15 |
| 16 | N-((1r,4r)-4-((8-cyanoquinolin-5-yl)oxy)cyclohexyl)-6-(4-((4-(2-(2,6-dioxopiperidin-3-yl)-1,3-dioxoisoindolin-5-yl)piperazin-1-yl)methyl)piperidin-1-yl)pyridazine-3-carboxamide | 3-16 |
| 17 | N-((1r,4r)-4-((8-cyanoquinolin-5-yl)oxy)cyclohexyl)-5-(4-((4-(2-(2,6-dioxopiperidin-3-yl)-1,3-dioxoisoindolin-5-yl)piperazin-1-yl)methyl)piperidin-1-yl)pyrazine-2-carboxamide | 3-17 |
| 18 | N-((1r,4r)-4-((8-cyanoquinolin-5-yl)oxy)cyclohexyl)-4-(4-((4-(2-(2,6-dioxopiperidin-3-yl)-1,3-dioxoisoindolin-5-yl)piperazin-1-yl)methyl)piperidin-1-yl)benzamide | 3-18 |

TABLE 2-continued

Exemplary Compounds of the Present Disclosure

| # | Structure & Name | Reference Number |
|---|---|---|
| 19 | 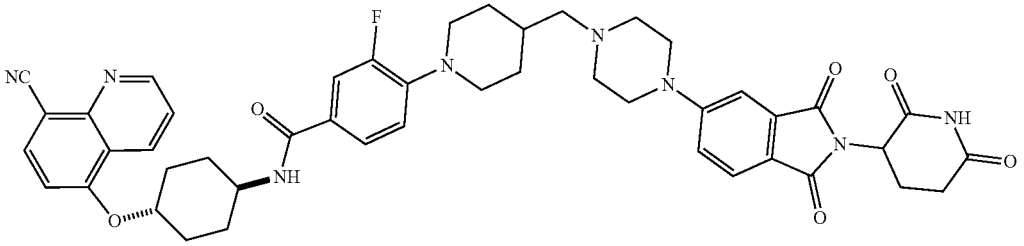<br>N-((1r,4r)-4-((8-cyanoquinolin-5-yl)oxy)cyclohexyl)-4-(4-((4-(2-(2,6-dioxopiperidin-3-yl)-1,3-dioxoisoindolin-5-yl)piperazin-1-yl)methyl)piperidin-1-yl)-3-fluorobenzamide | 3-19 |
| 20 | 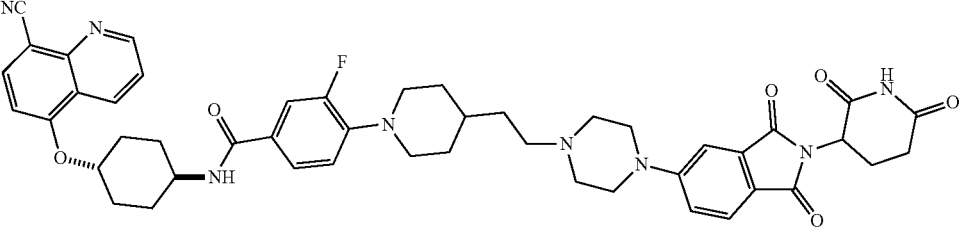<br>N-((1r,4r)-4-((8-cyanoquinolin-5-yl)oxy)cyclohexyl)-4-(4-(2-(4-(2-(2,6-dioxopiperidin-3-yl)-1,3-dioxoisoindolin-5-yl)piperazin-1-yl)ethyl)piperidin-1-yl)-3-fluorobenzamide | 3-20 |
| 21 | 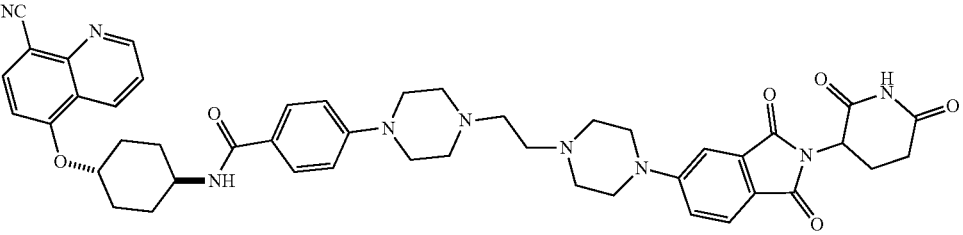<br>N-((1r,4r)-4-((8-cyanoquinolin-5-yl)oxy)cyclohexyl)-4-(4-(2-(4-(2-(2,6-dioxopiperidin-3-yl)-1,3-dioxoisoindolin-5-yl)piperazin-1-yl)ethyl)piperazin-1-yl)benzamide | 3-21 |
| 22 | 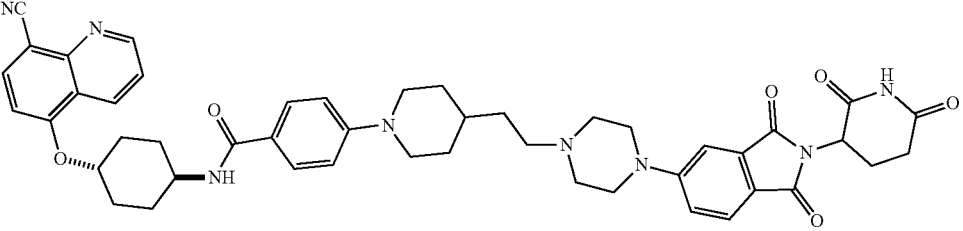<br>N-((1r,4r)-4-((8-cyanoquinolin-5-yl)oxy)cyclohexyl)-4-(4-(2-(4-(2-(2,6-dioxopiperidin-3-yl)-1,3-dioxoisoindolin-5-yl)piperazin-1-yl)ethyl)piperidin-1-yl)benzamide | 3-22 |
| 23 | 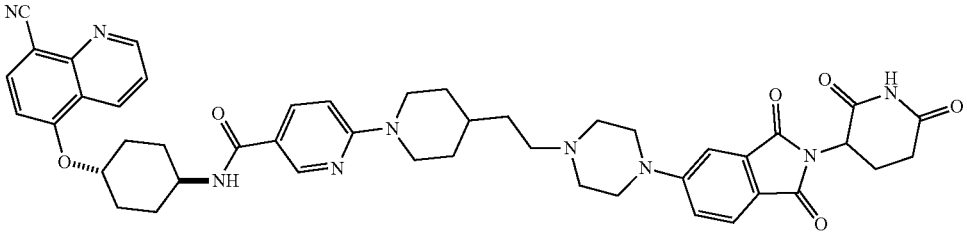<br>N-((1r,4r)-4-((8-cyanoquinolin-5-yl)oxy)cyclohexyl)-6-(4-(2-(4-(2-(2,6-dioxopiperidin-3-yl)-1,3-dioxoisoindolin-5-yl)piperazin-1-yl)ethyl)piperidin-1-yl)nicotinamide | 3-23 |

TABLE 2-continued

Exemplary Compounds of the Present Disclosure

| # | Structure & Name | Reference Number |
|---|---|---|
| 24 | N-((1r,4r)-4-((8-cyanoquinolin-5-yl)oxy)cyclohexyl)-2-(4-(2-(4-(2-(2,6-dioxopiperidin-3-yl)-1,3-dioxoisoindolin-5-yl)piperazin-1-yl)ethyl)piperidin-1-yl)pyrimidine-5-carboxamide | 3-24 |
| 25 | N-((1r,4r)-4-((8-cyanoquinolin-5-yl)oxy)cyclohexyl)-6-(4-(2-(4-(2-(2,6-dioxopiperidin-3-yl)-1,3-dioxoisoindolin-5-yl)piperazin-1-yl)ethyl)piperidin-1-yl)pyridazine-3-carboxamide | 3-25 |
| 26 | N-((1r,4r)-4-((8-cyanoquinolin-5-yl)oxy)cyclohexyl)-5-(4-(2-(4-(2-(2,6-dioxopiperidin-3-yl)-1,3-dioxoisoindolin-5-yl)piperazin-1-yl)ethyl)piperidin-1-yl)pyrazine-2-carboxamide | 3-26 |
| 27 | N-((1r,4r)-4-((8-cyanoquinolin-5-yl)oxy)cyclohexyl)-6-(4-((4-(2-(2,6-dioxopiperidin-3-yl)-1,3-dioxoisoindolin-5-yl)piperazin-1-yl)methyl)piperidin-1-yl)-5-fluoronicotinamide | 3-27 |
| 28 | N-((1r,4r)-4-((8-cyanoquinolin-5-yl)oxy)cyclohexyl)-6-(4-(2-(4-(2-(2,6-dioxopiperidin-3-yl)-1,3-dioxoisoindolin-5-yl)piperazin-1-yl)ethyl)piperidin-1-yl)-5-fluoronicotinamide | 3-28 |

TABLE 2-continued

Exemplary Compounds of the Present Disclosure

| # | Structure & Name | Reference Number |
|---|---|---|
| 29 | N-((1r,4r)-4-((8-cyanoquinolin-5-yl)oxy)cyclohexyl)-6-(4-((4-(2-((S)-2,6-dioxopiperidin-3-yl)-1-oxoisoindolin-5-yl)piperazin-1-yl)methyl)piperidin-1-yl)nicotinamide | 3-29 |
| 30 | N-((1r,4r)-4-((8-cyanoquinolin-5-yl)oxy)cyclohexyl)-2-(4-((4-(2-((S)-2,6-dioxopiperidin-3-yl)-1-oxoisoindolin-5-yl)piperazin-1-yl)methyl)piperidin-1-yl)pyrimidine-5-carboxamide | 3-30 |
| 31 | N-((1r,4r)-4-((8-cyanoquinolin-5-yl)oxy)cyclohexyl)-4-(4-((4-(2-((S)-2,6-dioxopiperidin-3-yl)-1-oxoisoindolin-5-yl)piperazin-1-yl)methyl)piperidin-1-yl)-3-fluorobenzamide | 3-31 |
| 32 | N-((1r,4r)-4-((8-cyanoquinolin-5-yl)oxy)cyclohexyl)-6-(4-((4-(2-((S)-2,6-dioxopiperidin-3-yl)-1-oxoisoindolin-5-yl)piperazin-1-yl)methyl)piperidin-1-yl)pyridazine-3-carboxamide | 3-32 |

TABLE 2-continued

Exemplary Compounds of the Present Disclosure

| # | Structure & Name | Reference Number |
|---|---|---|
| 33 | N-((1r,4r)-4-((8-cyanoquinolin-5-yl)oxy)cyclohexyl)-6-(4-(((4-(2-((S)-2,6-dioxopiperidin-3-yl)-6-fluoro-1-oxoisoindolin-5-yl)piperazin-1-yl)methyl)piperidin-1-yl)nicotinamide | 3-33 |
| 34 | N-((1r,4r)-4-((8-cyanoquinolin-5-yl)oxy)cyclohexyl)-6-(4-(((4-(2-((S)-2,6-dioxopiperidin-3-yl)-6-fluoro-1-oxoisoindolin-5-yl)piperazin-1-yl)methyl)piperidin-1-yl)pyridazine-3-carboxamide | 3-34 |
| 35 | N-((1r,4r)-4-((8-cyanoquinolin-5-yl)oxy)cyclohexyl)-6-(4-(((4-(2-(2,6-dioxopiperidin-3-yl)-6-fluoro-1,3-dioxoisoindolin-5-yl)piperazin-1-yl)methyl)piperidin-1-yl)nicotinamide | 3-35 |
| 36 | N-((1r,4r)-4-((8-cyanoquinolin-5-yl)oxy)cyclohexyl)-6-(4-(((4-(2-(2,6-dioxopiperidin-3-yl)-6-fluoro-1,3-dioxoisoindolin-5-yl)piperazin-1-yl)methyl)piperidin-1-yl)pyridazine-3-carboxamide | 3-36 |

TABLE 2-continued

Exemplary Compounds of the Present Disclosure

| # | Structure & Name | Reference Number |
|---|---|---|
| 37 | N-((1r,4r)-4-((8-cyanoquinolin-5-yl)oxy)cyclohexyl)-6-(4-(((2S)-4-(2-(2,6-dioxopiperidin-3-yl)-1,3-dioxoisoindolin-5-yl)-2-methylpiperazin-1-yl)methyl)piperidin-1-yl)nicotinamide | 3-37 |
| 38 | N-((1r,4r)-4-((8-cyanoquinolin-5-yl)oxy)cyclohexyl)-6-(4-(((2R)-4-(2-(2,6-dioxopiperidin-3-yl)-1,3-dioxoisoindolin-5-yl)-2-methylpiperazin-1-yl)methyl)piperidin-1-yl)nicotinamide | 3-38 |
| 39 | N-((1r,4r)-4-((8-cyanoquinolin-5-yl)oxy)cyclohexyl)-4-(4-(((2S)-4-(2-(2,6-dioxopiperidin-3-yl)-1,3-dioxoisoindolin-5-yl)-2-methylpiperazin-1-yl)methyl)piperidin-1-yl)-3-fluorobenzamide | 3-39 |
| 40 | N-((1r,4r)-4-((8-cyanoquinolin-5-yl)oxy)cyclohexyl)-4-(4-(((2R)-4-(2-(2,6-dioxopiperidin-3-yl)-1,3-dioxoisoindolin-5-yl)-2-methylpiperazin-1-yl)methyl)piperidin-1-yl)-3-fluorobenzamide | 3-40 |

TABLE 2-continued

Exemplary Compounds of the Present Disclosure

| # | Structure & Name | Reference Number |
|---|---|---|
| 41 | 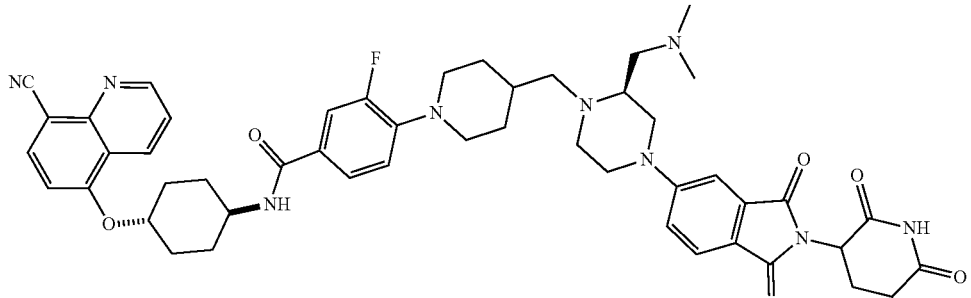<br>N-((1r,4r)-4-((8-cyanoquinolin-5-yl)oxy)cyclohexyl)-4-(4-(((2S)-2-((dimethylamino)methyl)-4-(2-(2,6-dioxopiperidin-3-yl)-1,3-dioxoisoindolin-5-yl)piperazin-1-yl)methyl)piperidin-1-yl)-3-fluorobenzamide | 3-41 |
| 42 | 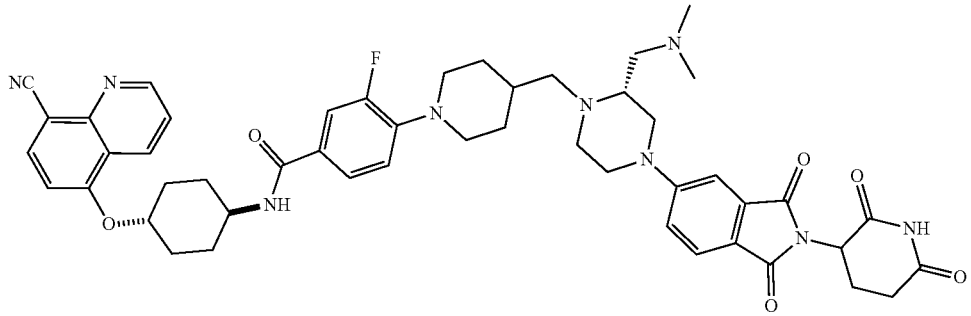<br>N-((1r,4r)-4-((8-cyanoquinolin-5-yl)oxy)cyclohexyl)-4-(4-(((2R)-2-((dimethylamino)methyl)-4-(2-(2,6-dioxopiperidin-3-yl)-1,3-dioxoisoindolin-5-yl)piperazin-1-yl)methyl)piperidin-1-yl)-3-fluorobenzamide | 3-42 |
| 43 | 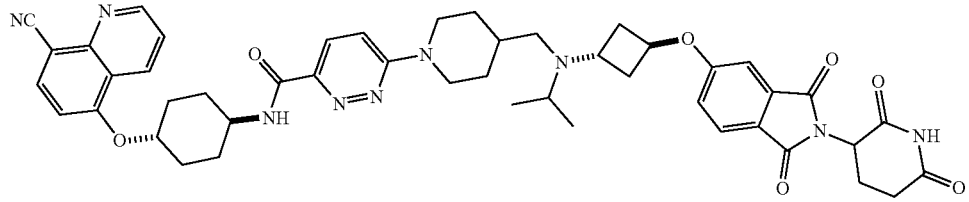<br>N-((1r,4r)-4-((8-cyanoquinolin-5-yl)oxy)cyclohexyl)-6-(4-(((((1r,3r)-3-((2-(2,6-dioxopiperidin-3-yl)-1,3-dioxoisoindolin-5-yl)oxy)cyclobutyl)(isopropyl)amino)methyl)piperidin-1-yl)pyridazine-3-carboxamide | 3-43 |
| 44 | 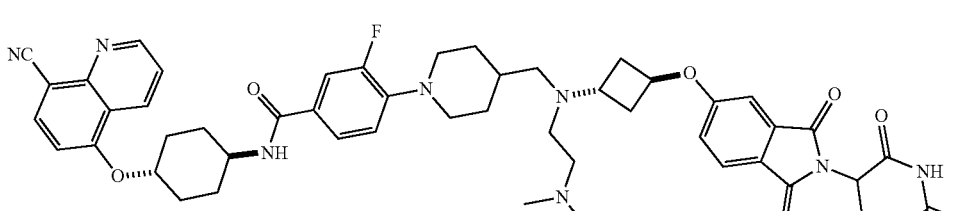<br>N-((1r,4r)-4-((8-cyanoquinolin-5-yl)oxy)cyclohexyl)-4-(4-(((2-(dimethylamino)ethyl)((1r,3r)-3-((2-(2,6-dioxopiperidin-3-yl)-1,3-dioxoisoindolin-5-yl)oxy)cyclobutyl)amino)methyl)piperidin-1-yl)-3-fluorobenzamide | 3-44 |

TABLE 2-continued

Exemplary Compounds of the Present Disclosure

| # | Structure & Name | Reference Number |
|---|---|---|
| 45 | N-((1r,4r)-4-((8-cyanoquinolin-5-yl)oxy)cyclohexyl)-6-(4-(((2S)-2-((dimethylamino)methyl)-4-(2-(2,6-dioxopiperidin-3-yl)-1,3-dioxoisoindolin-5-yl)piperazin-1-yl)methyl)piperidin-1-yl)nicotinamide | 3-45 |
| 46 | N-((1r,4r)-4-((8-cyanoquinolin-5-yl)oxy)cyclohexyl)-6-(4-(((2R)-2-((dimethylamino)methyl)-4-(2-(2,6-dioxopiperidin-3-yl)-1,3-dioxoisoindolin-5-yl)piperazin-1-yl)methyl)piperidin-1-yl)nicotinamide | 3-46 |
| 47 | N-((1r,4r)-4-((8-cyanoquinolin-5-yl)oxy)cyclohexyl)-6-(4-((4-(2-((S)-2,6-dioxopiperidin-3-yl)-6-fluoro-1-oxoisoindolin-5-yl)piperazin-1-yl)methyl)piperidin-1-yl)-5-fluoronicotinamide | 3-47 |
| 48 | N-((1r,4r)-4-((8-cyanoquinolin-5-yl)oxy)cyclohexyl)-2-(4-((4-(2-((S)-2,6-dioxopiperidin-3-yl)-6-fluoro-1-oxoisoindolin-5-yl)piperazin-1-yl)methyl)piperidin-1-yl)pyrimidine-5-carboxamide | 3-48 |

TABLE 2-continued

Exemplary Compounds of the Present Disclosure

| # | Structure & Name | Reference Number |
|---|---|---|
| 49 | N-((1r,4r)-4-((8-cyanoquinolin-5-yl)oxy)cyclohexyl)-4-(4-((4-(2-(2,6-dioxopiperidin-3-yl)-6-fluoro-1,3-dioxoisoindolin-5-yl)piperazin-1-yl)methyl)piperidin-1-yl)benzamide | 3-49 |
| 50 | N-((1r,4r)-4-((8-cyanoquinolin-5-yl)oxy)cyclohexyl)-4-(4-((4-(2-(2,6-dioxopiperidin-3-yl)-6-fluoro-1,3-dioxoisoindolin-5-yl)piperazin-1-yl)methyl)piperidin-1-yl)-3-fluorobenzamide | 3-50 |
| 51 | N-((1r,4r)-4-((8-cyanoquinolin-5-yl)oxy)cyclohexyl)-2-(4-((4-(2-(2,6-dioxopiperidin-3-yl)-6-fluoro-1,3-dioxoisoindolin-5-yl)piperazin-1-yl)methyl)piperidin-1-yl)pyrimidine-5-carboxamide | 3-51 |
| 52 | N-((1r,4r)-4-((8-cyanoquinolin-5-yl)oxy)cyclohexyl)-5-(4-((4-(2-(2,6-dioxopiperidin-3-yl)-6-fluoro-1,3-dioxoisoindolin-5-yl)piperazin-1-yl)methyl)piperidin-1-yl)pyrazine-2-carboxamide | 3-52 |

TABLE 2-continued

Exemplary Compounds of the Present Disclosure

| # | Structure & Name | Reference Number |
|---|---|---|
| 53 | N-((1r,4r)-4-((8-cyanoquinolin-5-yl)oxy)cyclohexyl)-6-(4-((4-(2,6-dioxopiperidin-3-yl)-6-fluoro-1,3-dioxoisoindolin-5-yl)piperazin-1-yl)methyl)piperidin-1-yl)-5-fluoronicotinamide | 3-53 |
| 54 | N-((1r,4S)-4-((8-cyanoquinolin-5-yl)oxy)cyclohexyl)-2-((3S)-3-((4-(2-(2,6-dioxopiperidin-3-yl)-1,3-dioxoisoindolin-5-yl)piperazin-1-yl)methyl)pyrrolidin-1-yl)pyrimidine-5-carboxamide | 3-54 |
| 55 | N-((1r,4R)-4-((8-cyanoquinolin-5-yl)oxy)cyclohexyl)-2-((3R)-3-((4-(2-(2,6-dioxopiperidin-3-yl)-1,3-dioxoisoindolin-5-yl)piperazin-1-yl)methyl)pyrrolidin-1-yl)pyrimidine-5-carboxamide | 3-55 |

Pharmaceutical Compositions

Pharmaceutical compositions of the present disclosure comprise at least one compound of Formula (1) (e.g. Formula (1A)), or a tautomer, stereoisomer, or pharmaceutically acceptable salt thereof, or a deuterated derivative of any of the foregoing formulated together with a pharmaceutically acceptable carrier. These formulations include those suitable for oral, rectal, topical, buccal and parenteral (e.g., subcutaneous, intramuscular, intradermal, or intravenous) administration. The most suitable form of administration in any given case will depend on the degree and severity of the condition being treated and on the nature of the particular compound being used.

Formulations suitable for oral administration may be presented in discrete units, such as capsules, cachets, lozenges, or tablets, each containing a predetermined amount of a compound of the present disclosure as powder or granules; as a solution or a suspension in an aqueous or non-aqueous liquid; or as an oil-in-water or water-in-oil emulsion. As indicated, such formulations may be prepared by any suitable method of pharmacy which includes the step of bringing into association at least one compound of the present disclosure as the active compound and a carrier or excipient (which may constitute one or more accessory ingredients). The carrier must be acceptable in the sense of being compatible with the other ingredients of the formulation and must not be deleterious to the recipient. The carrier may be a solid or a liquid, or both, and may be formulated with at least one compound described herein as the active compound in a unit-dose formulation, for example, a tablet, which may contain from about 0.05% to about 95% by weight of the at least one active compound. Other pharmacologically active substances may also be present including other compounds. The formulations of the present disclosure may be prepared by any of the well-known techniques of pharmacy consisting essentially of admixing the components.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by, for example, dissolving or dispersing, at least one active compound of the present disclosure as described herein and optional pharmaceutical adjuvants in an excipient, such as, for example, water, saline, aqueous dextrose, glycerol, ethanol, and the like, to thereby form a solution or suspension. In general, suitable formulations may be prepared by uniformly and intimately admixing the at least one active compound of the present disclosure with a liquid or finely divided solid carrier, or both, and then, if necessary, shaping the product. For example, a tablet may be prepared by compressing or molding a powder or granules of at least one compound of the present disclosure, which may be optionally combined with one or more accessory ingredients. Compressed tablets may be prepared by compressing, in a suitable machine, at least one compound of the present disclosure in a free-flowing form, such as a powder or granules, which may be optionally mixed with a binder, lubricant, inert diluent and/or surface active/dispersing agent(s). Molded tablets may be made by molding, in a suitable machine, where the powdered form of at least one compound of the present disclosure is moistened with an inert liquid diluent.

Formulations suitable for buccal (sub-lingual) administration include lozenges comprising at least one compound of the present disclosure in a flavored base, usually sucrose and acacia or tragacanth, and pastilles comprising the at least one compound in an inert base such as gelatin and glycerin or sucrose and acacia.

Formulations of the present disclosure suitable for parenteral administration comprise sterile aqueous preparations of at least one compound of Formula (1) (e.g. Formula (1A), or a tautomer, stereoisomer, or pharmaceutically acceptable salt thereof, or a deuterated derivative of any of the foregoing, which are approximately isotonic with the blood of the intended recipient. These preparations are administered intravenously, although administration may also be affected by means of subcutaneous, intramuscular, or intradermal injection. Such preparations may conveniently be prepared by admixing at least one compound described herein with water and rendering the resulting solution sterile and isotonic with the blood. Injectable compositions according to the present disclosure may contain from about 0.1 to about 5% w/w of the active compound.

Formulations suitable for rectal administration are presented as unit-dose suppositories. These may be prepared by admixing at least one compound as described herein with one or more conventional solid carriers, for example, cocoa butter, and then shaping the resulting mixture.

Formulations suitable for topical application to the skin may take the form of an ointment, cream, lotion, paste, gel, spray, aerosol, or oil. Carriers and excipients which may be used include Vaseline, lanoline, polyethylene glycols, alcohols, and combinations of two or more thereof. The active compound (i.e., at least one compound of Formula (1) (e.g. Formula (1A), or a tautomer, stereoisomer, or pharmaceutically acceptable salt thereof, or a deuterated derivative of any of the foregoing) is generally present at a concentration of from about 0.1% to about 15% w/w of the composition, for example, from about 0.5 to about 2%.

The amount of active compound administered may be dependent on the subject being treated, the subject's weight, the manner of administration and the judgment of the prescribing physician. For example, a dosing schedule may involve the daily or semi-daily administration of the encapsulated compound at a perceived dosage of about 1 µg to about 1000 mg. In another embodiment, intermittent administration, such as on a monthly or yearly basis, of a dose of the encapsulated compound may be employed. Encapsulation facilitates access to the site of action and allows the administration of the active ingredients simultaneously, in theory producing a synergistic effect. In accordance with standard dosing regimens, physicians will readily determine optimum dosages and will be able to readily modify administration to achieve such dosages.

A therapeutically effective amount of a compound or composition disclosed herein can be measured by the therapeutic effectiveness of the compound. The dosages, however, may be varied depending upon the requirements of the patient, the severity of the condition being treated, and the compound being used. In one embodiment, the therapeutically effective amount of a disclosed compound is sufficient to establish a maximal plasma concentration. Preliminary doses as, for example, determined according to animal tests, and the scaling of dosages for human administration is performed according to art-accepted practices.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferable.

Data obtained from the cell culture assays or animal studies can be used in formulating a range of dosage for use in humans. Therapeutically effective dosages achieved in one animal model may be converted for use in another animal, including humans, using conversion factors known in the art (see, e.g., Freireich et al., *Cancer Chemother. Reports* 50(4):219-244 (1966) and the following table (Table 3) for Equivalent Surface Area Dosage Factors).

TABLE 3

Equivalent Surface Area Dosage Factors.

| From: | Mouse (20 g) | Rat (150 g) | Monkey (3.5 kg) | Dog (8 kg) | Human (60 kg) |
|---|---|---|---|---|---|
| Mouse | 1 | 1/2 | 1/4 | 1/6 | 1/12 |
| Rat | 2 | 1 | 1/2 | 1/4 | 1/7 |
| Monkey | 4 | 2 | 1 | 3/5 | 1/3 |
| Dog | 6 | 4 | 3/5 | 1 | 1/2 |
| Human | 12 | 7 | 3 | 2 | 1 |

The dosage of such compounds lies preferably within a range of circulating concentrations that include the $ED_{50}$ with little or no toxicity. The dosage may vary within this range depending upon the dosage form employed and the route of administration utilized. Generally, a therapeutically effective amount may vary with the subject's age, condition, and gender, as well as the severity of the medical condition in the subject. The dosage may be determined by a physician and adjusted, as necessary, to suit observed effects of the treatment.

Methods of Treatment

In some embodiments, a compound of Formula (1) (e.g. Formula (1A)), or a tautomer, stereoisomer, or pharmaceutically acceptable salt thereof, or a deuterated derivative of any of the foregoing, is administered to treat cancer in a subject in need thereof. In some embodiments, the cancer is chosen from prostate cancer, head and neck cancer, skin cancer, sarcoma, renal cell carcinoma, adrenocortical carcinoma, bladder cancer, lung cancer, gastric carcinoma, esophageal carcinoma, pancreatic adenocarcinoma, colorectal cancer, connective tissue cancer, glioblastoma multiforme, cervical cancer, uterine cancer, ovarian cancer, and breast cancer. In some embodiments, the cancer is prostate cancer. In some embodiments, the cancer is head and neck cancer. In some embodiments, the cancer is skin cancer. In some embodiments, the cancer is sarcoma. In some embodiments, the cancer is renal cell carcinoma. In some embodiments, the cancer is adrenocortical carcinoma. In some embodiments, the cancer is bladder cancer. In some embodiments, the cancer is lung cancer. In some embodiments, the cancer is gastric carcinoma. In some embodiments, the cancer is esophageal carcinoma. In some embodiments, the cancer is pancreatic adenocarcinoma. In some embodiments, the cancer is colorectal cancer. In some embodiments, the cancer is connective tissue cancer. In some embodiments, the cancer is glioblastoma multiforme. In some embodiments, the cancer is cervical cancer. In some embodiments, the cancer is uterine cancer. In some embodiments, the cancer is ovarian cancer. In some embodiments, the cancer is breast cancer.

In some embodiments, the cancer is androgen receptor positive.

In some embodiments, a compound of Formula (1) (e.g. Formula (1A), or a tautomer, stereoisomer, or pharmaceutically acceptable salt thereof, or a deuterated derivative of any of the foregoing, is administered as a pharmaceutical composition.

In some embodiments, the subject has been previously treated with an anti-cancer agent. In some embodiments, the anti-cancer agent is enzalutamide, apalutamide, bicalutamide, darolutamide, flutamide, abirbtarone, or a combination of any of the foregoing. In some embodiments, the anti-cancer agent is enzalutamide.

In some embodiments, provided herein is a use of a compound of Formula (1), or a tautomer, stereoisomer, or pharmaceutically acceptable salt thereof, or a deuterated derivative of any of the foregoing, for treating cancer. In some embodiments, the cancer is selected from prostate cancer, head and neck cancer, skin cancer, sarcoma, renal cell carcinoma, adrenocortical carcinoma, bladder cancer, lung cancer, gastric carcinoma, esophageal carcinoma, pancreatic adenocarcinoma, colorectal cancer, connective tissue cancer, glioblastoma multiforme, cervical cancer, uterine cancer, ovarian cancer, and breast cancer. In some embodiments, the cancer is prostate cancer. In some embodiments, the cancer is head and neck cancer. In some embodiments, the cancer is skin cancer. In some embodiments, the cancer is sarcoma. In some embodiments, the cancer is renal cell carcinoma. In some embodiments, the cancer is adrenocortical carcinoma. In some embodiments, the cancer is bladder cancer. In some embodiments, the cancer is lung cancer. In some embodiments, the cancer is gastric carcinoma. In some embodiments, the cancer is esophageal carcinoma. In some embodiments, the cancer is pancreatic adenocarcinoma. In some embodiments, the cancer is colorectal cancer. In some embodiments, the cancer is connective tissue cancer. In some embodiments, the cancer is glioblastoma multiforme. In some embodiments, the cancer is cervical cancer. In some embodiments, the cancer is uterine cancer. In some embodiments, the cancer is ovarian cancer. In some embodiments, the cancer is breast cancer. In some embodiments, the cancer is androgen receptor positive.

In some embodiments, provided herein is a use of a compound of Formula (1), or a tautomer, stereoisomer, or pharmaceutically acceptable salt thereof, or a deuterated derivative of any of the foregoing, in the preparation of a medicament. In some embodiments, the medicament is for the treatment of cancer. In some embodiments, the cancer is selected from prostate cancer, head and neck cancer, skin cancer, sarcoma, renal cell carcinoma, adrenocortical carcinoma, bladder cancer, lung cancer, gastric carcinoma, esophageal carcinoma, pancreatic adenocarcinoma, colorectal cancer, connective tissue cancer, glioblastoma multiforme, cervical cancer, uterine cancer, ovarian cancer, and breast cancer. In some embodiments, the cancer is prostate cancer. In some embodiments, the cancer is head and neck cancer. In some embodiments, the cancer is skin cancer. In some embodiments, the cancer is sarcoma. In some embodiments, the cancer is renal cell carcinoma. In some embodiments, the cancer is adrenocortical carcinoma. In some embodiments, the cancer is bladder cancer. In some embodiments, the cancer is lung cancer. In some embodiments, the cancer is gastric carcinoma. In some embodiments, the cancer is esophageal carcinoma. In some embodiments, the cancer is pancreatic adenocarcinoma. In some embodiments, the cancer is colorectal cancer. In some embodiments, the cancer is connective tissue cancer. In some embodiments, the cancer is glioblastoma multiforme. In some embodiments, the cancer is cervical cancer. In some embodiments, the cancer is uterine cancer. In some embodiments, the cancer is ovarian cancer. In some embodiments, the cancer is breast cancer. In some embodiments, the cancer is androgen receptor positive.

In some embodiments, provided herein is a method of inhibiting cell growth comprising contacting a cell with a compound of Formula (1), or a tautomer, stereoisomer, or pharmaceutically acceptable salt thereof, or a deuterated derivative of any of the foregoing. In some embodiments, the cell is a cancer cell. In some embodiments, the cancer cell is a prostate cancer cell. In some embodiments, the cell is androgen receptor positive.

In one embodiment, a compound of Formula (1) (e.g. Formula (1A)), or a tautomer, stereoisomer, pharmaceutically acceptable salt or hydrate thereof, may be administered in combination with another therapeutic agent. The other therapeutic agent can provide additive or synergistic value relative to the administration of a compound of the present disclosure alone. The therapeutic agent can be selected from, for example, hormones and hormonal analogues; signal transduction pathway inhibitors; topoisomerase I inhibitors; topoisomerase II inhibitors; antimetabolite neoplastic agents; antibiotic neoplastic agents; alkylating agents; anti-microtubule agents; platinum coordination complexes; aromatase inhibitors; and anti-mitotic agents.

In some embodiments, the therapeutic agent may be a hormone or hormonal analogue. In some embodiments, the therapeutic agent may be a signal transduction pathway inhibitor. In some embodiments, the therapeutic agent may be a topoisomerase I inhibitor. In some embodiments, the therapeutic agent may be a topoisomerase II inhibitor. In some embodiments, the therapeutic agent may be an antimetabolite neoplastic agent. In some embodiments, the therapeutic agent may be an antibiotic neoplastic agent. In some embodiments, the therapeutic agent may be an alkylating agent. In some embodiments, the therapeutic agent may be an anti-microtubule agent. In some embodiments, the therapeutic agent may be a platinum coordination complex. In some embodiments, the therapeutic agent may be an aromatase inhibitor. In some embodiments, the therapeutic agent may be an anti-mitotic agent.

In some embodiments, the aromatase inhibitor may be selected from anastrazole, letrozole, vorozole, fadrozole, exemestane, and formestane. In some embodiments, the aromatase inhibitor is anastrazole. In some embodiments, the aromatase inhibitor may be letrozole. In some embodiments, the aromatase inhibitor may be vorozole. In some embodiments, the aromatase inhibitor may be fadrozole. In some embodiments, the aromatase inhibitor may be exemestane. In some embodiments, the aromatase inhibitor may be formestane.

In some embodiments, the anti-mitotic agent may be selected from paclitaxel, docetaxel, and Abraxane. In some embodiments, the anti-mitotic agent may be paclitaxel. In some embodiments, the anti-mitotic agent may be docetaxel. In some embodiments, the anti-mitotic agent may be Abraxane.

In some embodiments, a compound of Formula (1) (e.g. Formula (1A)), or a tautomer, stereoisomer, or pharmaceutically acceptable salt thereof, or a deuterated derivative of any of the foregoing, may be administered in combination with a hormone or hormonal analog. In some embodiments, a compound of Formula (1), or a tautomer, stereoisomer, or pharmaceutically acceptable salt thereof, or a deuterated derivative of any of the foregoing, may be administered in combination with a signal transduction pathway inhibitor. In some embodiments, a compound of Formula (1), or a tautomer, stereoisomer, or pharmaceutically acceptable salt thereof, or a deuterated derivative of any of the foregoing, may be administered in combination with an antimetabolite neoplastic agent. In some embodiments, a compound of Formula (1), or a tautomer, stereoisomer, or pharmaceutically acceptable salt thereof, or a deuterated derivative of any of the foregoing, may be administered in combination with a topoisomerase I inhibitor. In some embodiments, a compound of Formula (1), or a tautomer, stereoisomer, or pharmaceutically acceptable salt thereof, or a deuterated derivative of any of the foregoing, may be administered in combination with a topoisomerase II inhibitor. In some embodiments, a compound of Formula (1), or a tautomer, stereoisomer, or pharmaceutically acceptable salt thereof, or a deuterated derivative of any of the foregoing, may be administered in combination with an aromatase inhibitor.

EXAMPLES

The examples and preparations provided below further illustrate and exemplify the compounds as disclosed herein and methods of preparing such compounds. It is to be understood that the scope of the present disclosure is not limited in any way by the scope of the following examples and preparations.

The chemical entities described herein can be synthesized according to one or more illustrative schemes herein and/or techniques well known in the art. Unless specified to the contrary, the reactions described herein take place at atmospheric pressure, generally within a temperature range from about −10° C. to about 200° C. Further, except as otherwise specified, reaction times and conditions are intended to be approximate, e.g., taking place at about atmospheric pressure within a temperature range of about −10° C. to about 200° C. over a period that can be, for example, about 1 to about 24 hours; reactions left to run overnight in some embodiments can average a period of about 16 hours.

Isolation and purification of the chemical entities and intermediates described herein can be affected, if desired, by any suitable separation or purification procedure such as, for example, filtration, extraction, crystallization, column chromatography, thin-layer chromatography or thick-layer chromatography, or a combination of these procedures. See, e.g., Carey et al. Advanced Organic Chemistry, $3^{rd}$ Ed., 1990 New York: Plenum Press; Mundy et al., Name Reaction and Reagents in Organic Synthesis, $2^{nd}$ Ed., 2005 Hoboken, N.J.: J. Wiley & Sons. Specific illustrations of suitable separation and isolation procedures are given by reference to the examples hereinbelow. However, other equivalent separation or isolation procedures can also be used.

In all of the methods, it is well understood that protecting groups for sensitive or reactive groups may be employed where necessary, in accordance with general principles of chemistry. Protecting groups are manipulated according to standard methods of organic synthesis (T. W. Greene and P. G. M. Wuts (1999) Protective Groups in Organic Synthesis, $3^{rd}$ Ed., John Wiley & Sons). These groups may be removed at a convenient stage of the compound synthesis using methods that are readily apparent to those skilled in the art.

When desired, the (R)- and (S)-isomers of the nonlimiting exemplary compounds, if present, can be resolved by methods known to those skilled in the art, for example, by formation of diastereoisomeric salts or complexes which can be separated, e.g., by crystallization; via formation of diastereoisomeric derivatives which can be separated, e.g., by crystallization, gas-liquid or liquid chromatography; selective reaction of one enantiomer with an enantiomer-specific reagent, e.g., enzymatic oxidation or reduction, followed by separation of the modified and unmodified enantiomers; or gas-liquid or liquid chromatography in a chiral environment, e.g., on a chiral support, such as silica with a bound chiral ligand or in the presence of a chiral solvent. Alternatively, a specific enantiomer can be synthesized by asymmetric synthesis using optically active reagents, substrates, catalysts or solvents, or by converting one enantiomer to the other by asymmetric transformation.

The compounds described herein can be optionally contacted with a pharmaceutically acceptable acid to form the corresponding acid addition salts. Also, the compounds described herein can be optionally contacted with a pharmaceutically acceptable base to form the corresponding basic addition salts.

In some embodiments, disclosed compounds can generally be synthesized by an appropriate combination of generally well-known synthetic methods. Techniques useful in synthesizing these chemical entities are both readily apparent and accessible to those of skill in the relevant art, based on the instant disclosure. Many of the optionally substituted starting compounds and other reactants are commercially available, e.g., from Millipore Sigma or can be readily prepared by those skilled in the art using commonly employed synthetic methodology.

The discussion below is offered to illustrate certain of the diverse methods available for use in making the disclosed compounds and is not intended to limit the scope of reactions or reaction sequences that can be used in preparing the compounds provided herein. The skilled artisan will understand that standard atom valencies apply to all compounds disclosed herein in genus or named compound for unless otherwise specified.

All final compounds of the examples described herein were checked for purity by HPLC on a Shimadzu LC-2010A and compounds were detected at the wavelength of 214 nM and 254 nM. Purities for all final compounds were over 95% based on HPLC peaks (214 nM and 254 nM wavelength). Liquid chromatography condition: Column, XBRIDGE C18, 3.6 micron, 2.1×50 mm: Mobile phase, water (0.05% TFA) and acetonitrile (0.05% TFA), linear gradient from 10% acetonitrile to 100% acetonitrile over 7 min; Oven temperature 45° C.; Flow rate, 0.8 mL/mL. H-NMR was obtained on Bruker 400 MHz NMR spectrometer.

General Synthetic Schemes

Compounds of Formula (1) (e.g. Formula (1A); see compounds in Table 2) can be prepared according to the following schemes. The following schemes represent the general methods used in preparing these compounds. However, the synthesis of these compounds is not limited to these representative methods, as they can also be prepared by various other methods those skilled in the art of synthetic chemistry, for example, in a stepwise or modular fashion.

Scheme 1 Synthesis of 3-1.
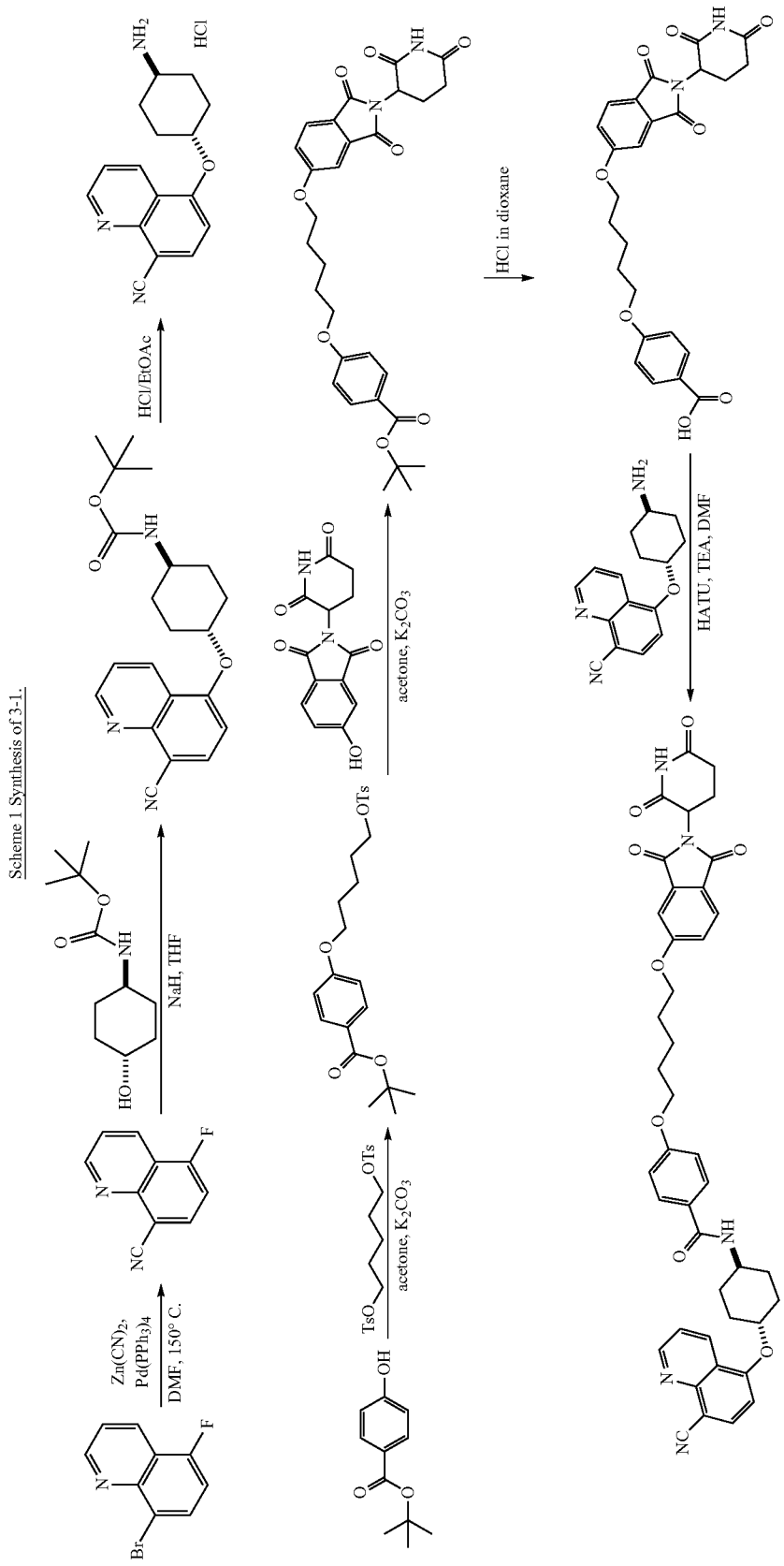

Compound 3-2 can be synthesized according to the similar method as described in Scheme 1.
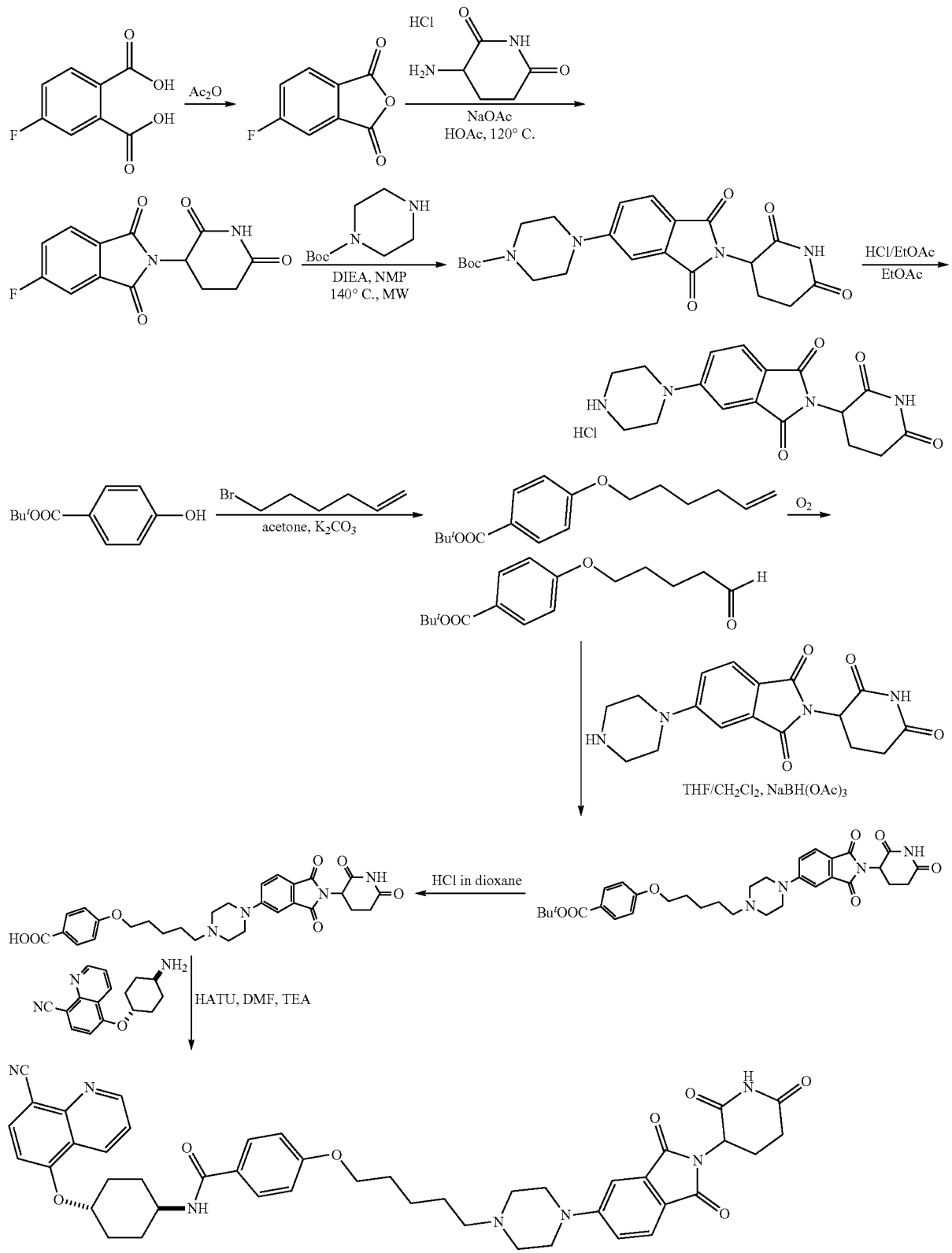
Scheme 2 Synthesis of 3-6.

Compounds 3-3, 3-4, and 3-5 can be prepared according to the similar method as described in Scheme 2.
Scheme 3 Synthesis of 3-7.
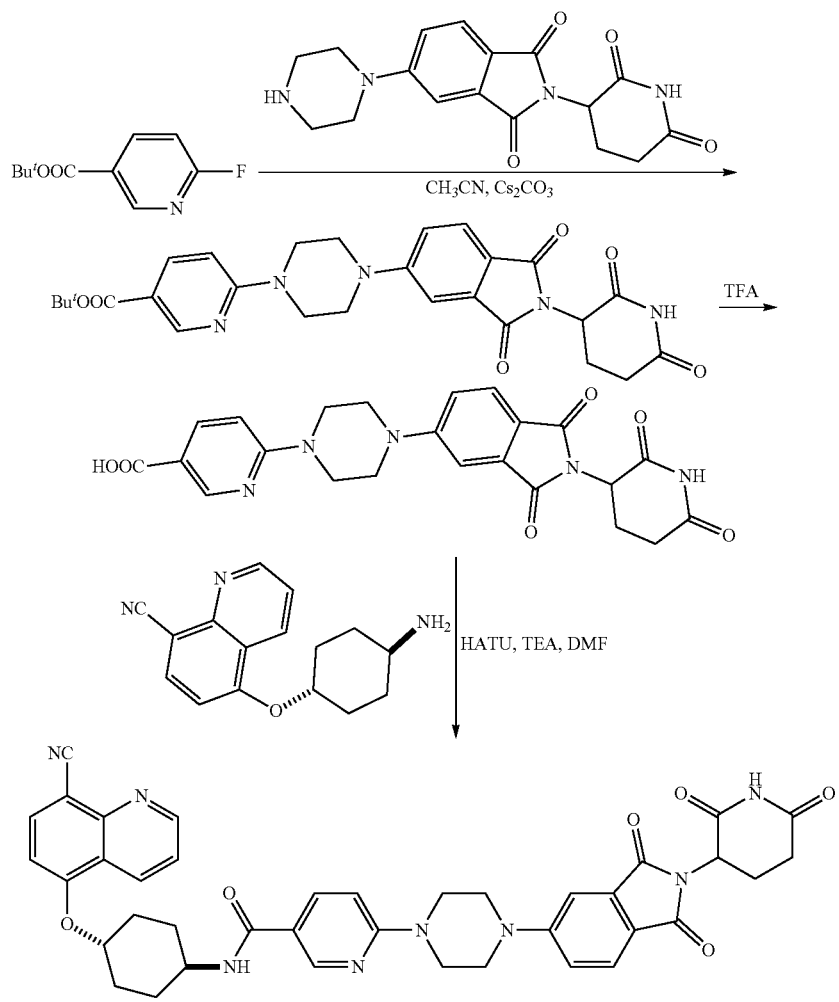
Scheme 4 Synthesis of 3-13.
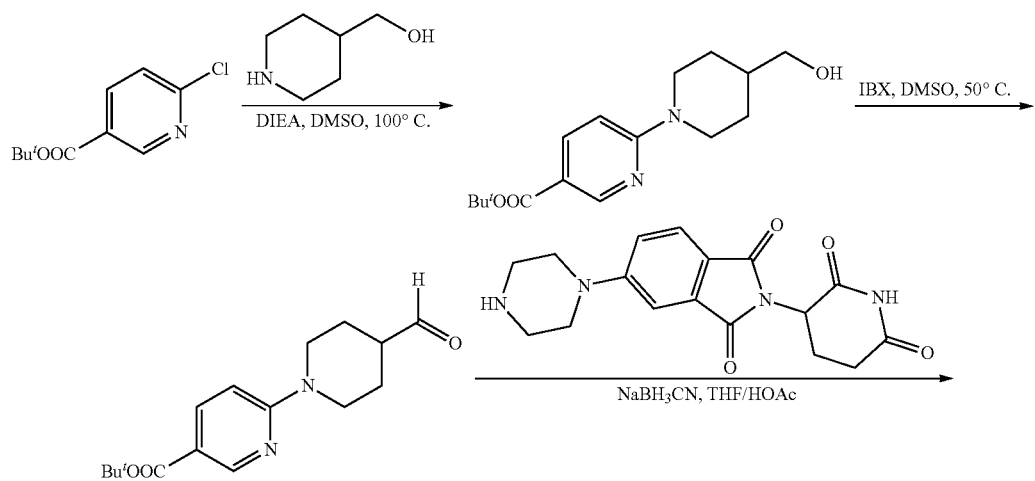

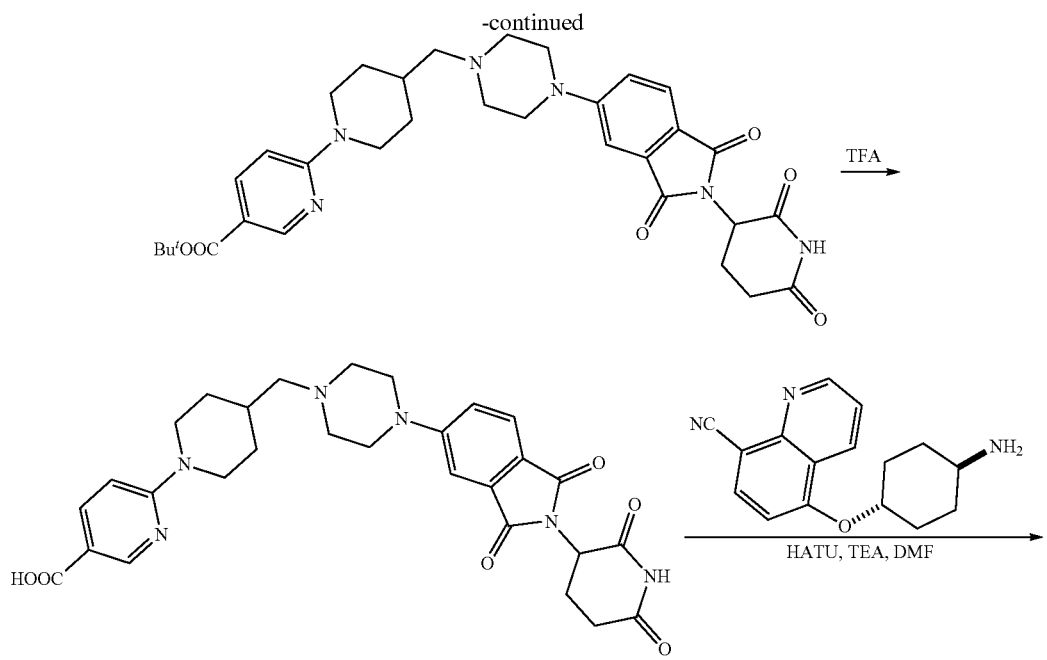
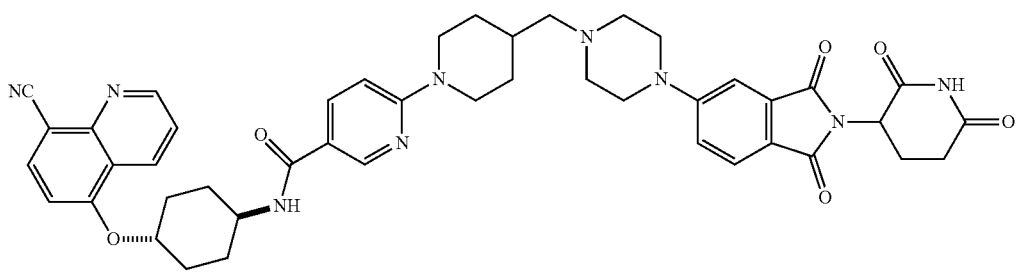
Compounds 3-14, 3-15, 3-16, 3-17, 3-18, 3-19, and 3-27 can be synthesized with similar method as described in Scheme 4.
Scheme 5 Synthesis of 3-22.
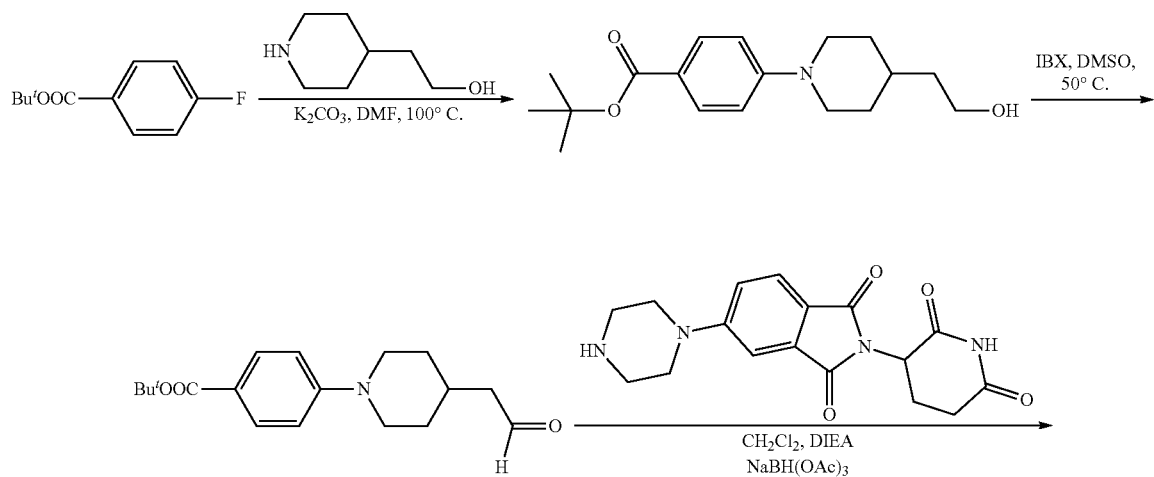

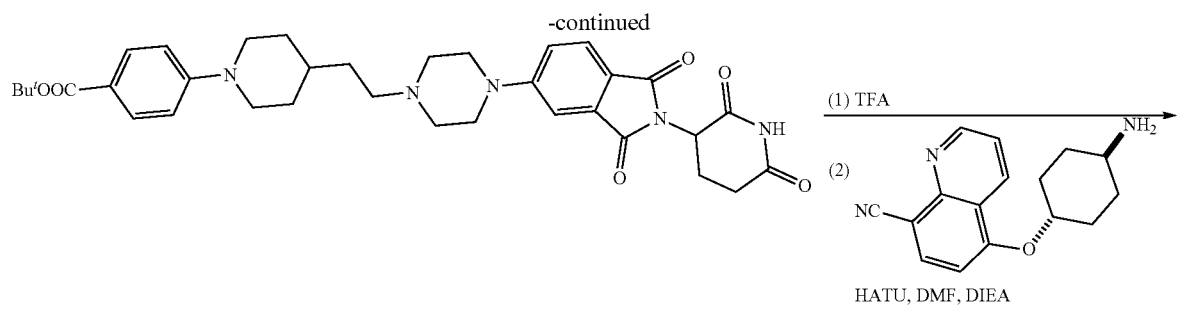
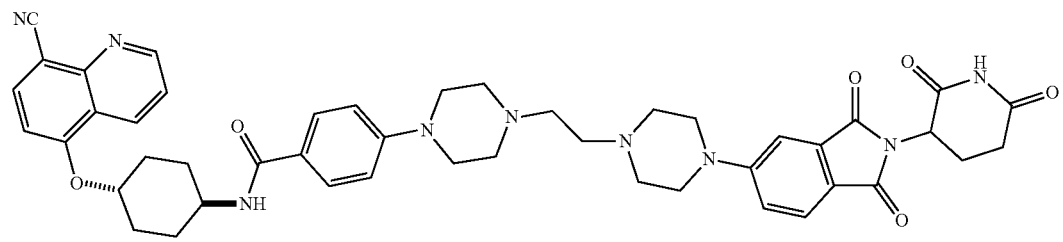
Compounds 3-20, 3-21, 3-23, 32-24, 3-25, 3-26 and 3-28 can be prepared using the similar synthetic route.
Scheme 6 Synthesis of 3-31.
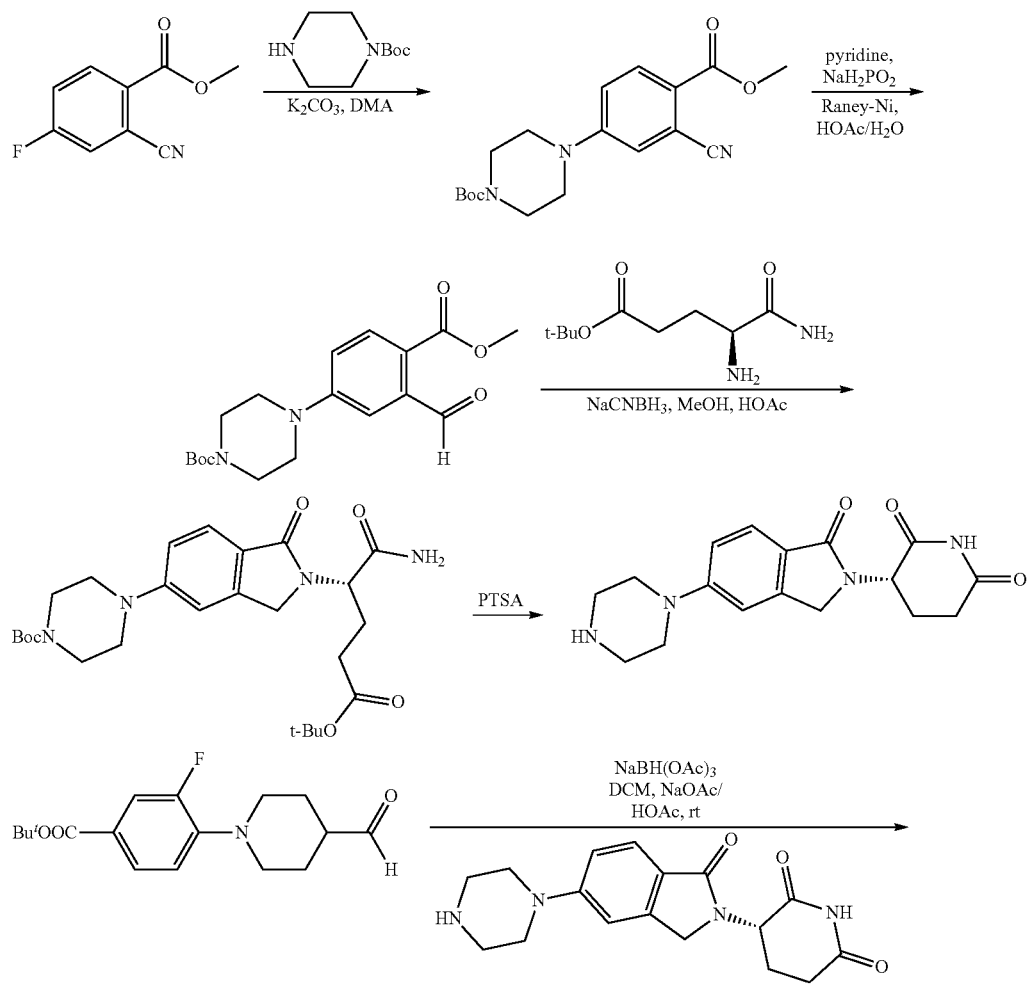

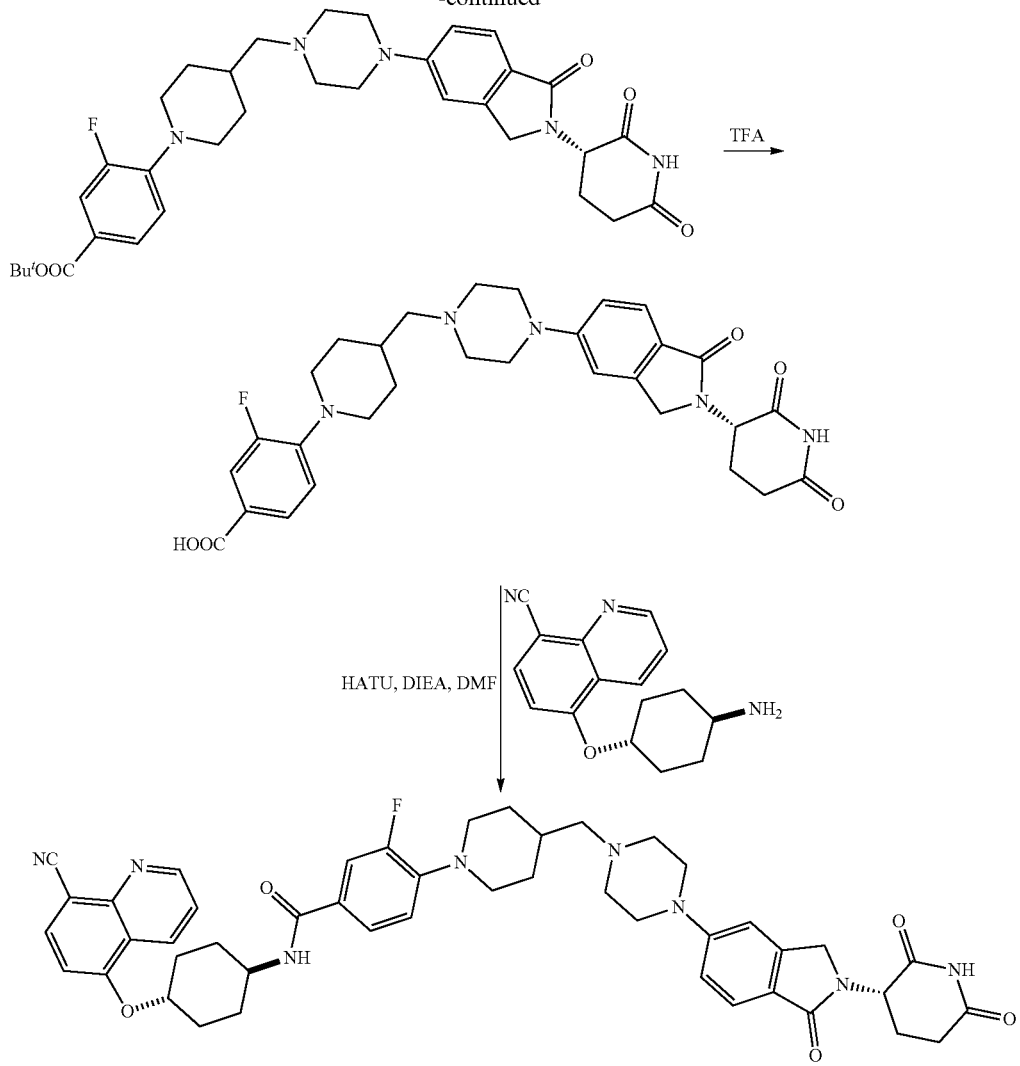
The following compounds can be synthesized according to similar synthetic method as described in Scheme 6: 3-29, 3-30, 3-32, 3-33, 3-34, 3-47 and 3-48.
Scheme 7 Synthesis of 3-11.
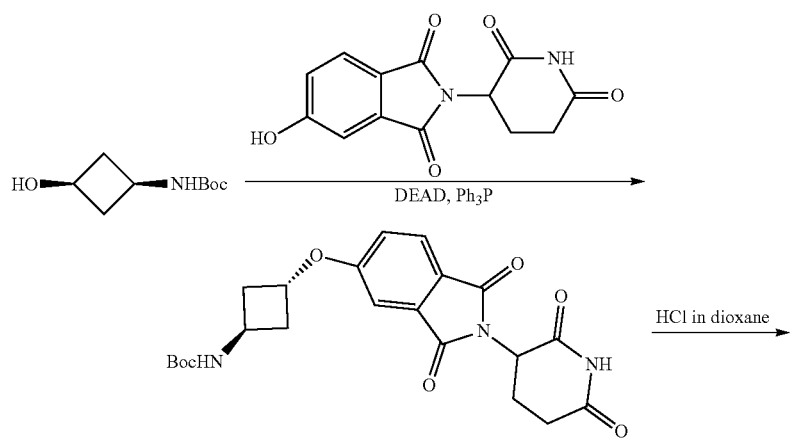

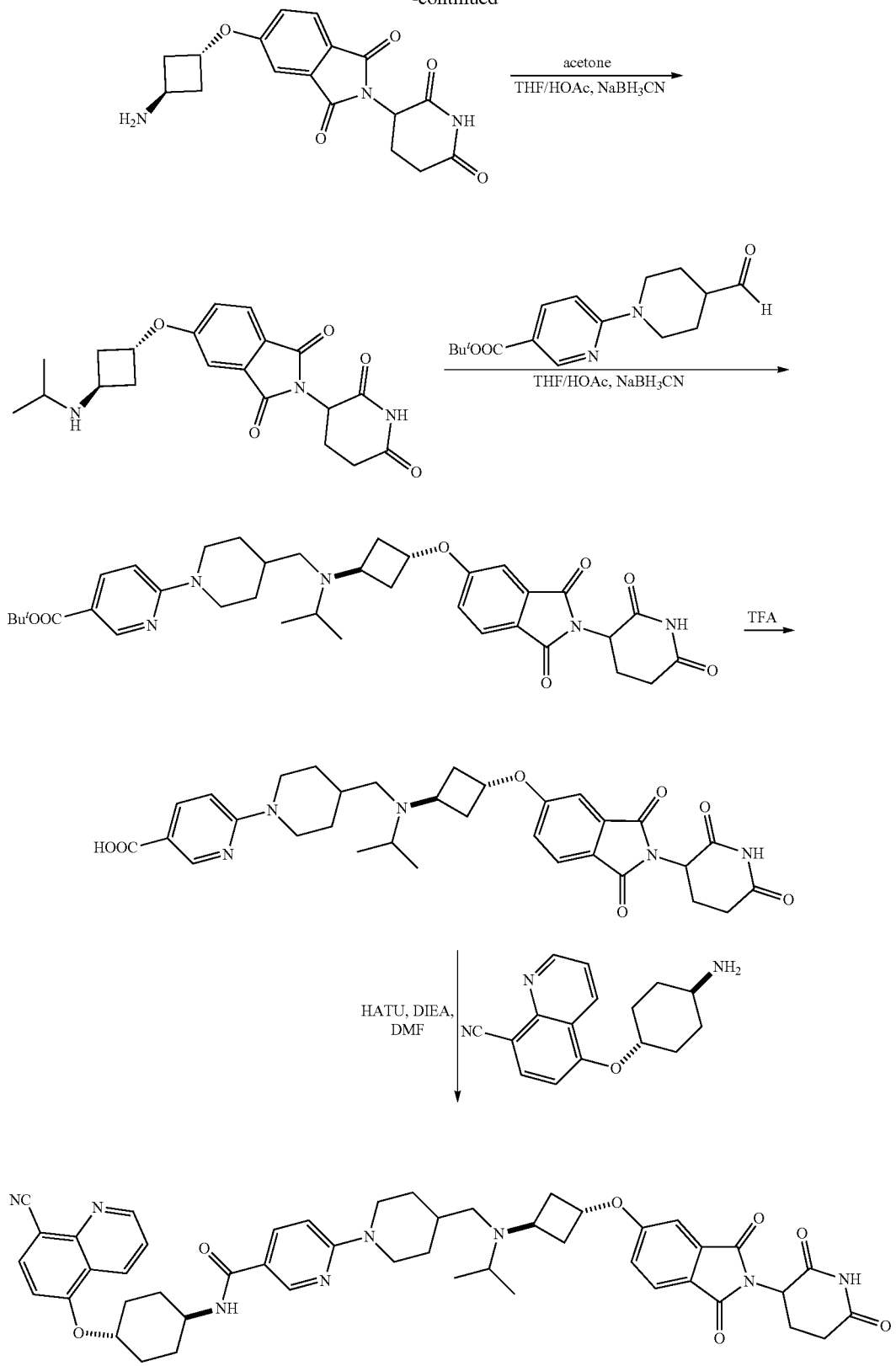
The following compounds can be synthesized according to similar synthetic method as described in Scheme 7: 3-8, 3-9, 3-10, 3-12 and 3-43.

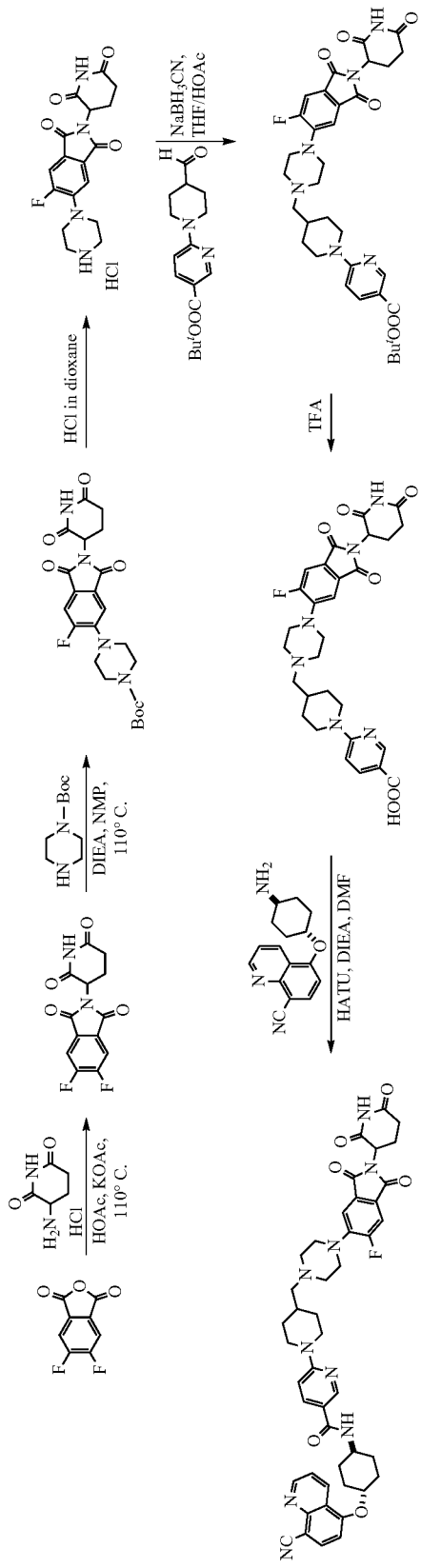
Scheme 8 Synthesis of 3-35.

Compounds 3-36, 3-49, 3-50, 3-51 and 3-52 can be synthesized using the same method.
Scheme 9 Synthesis of 3-37.
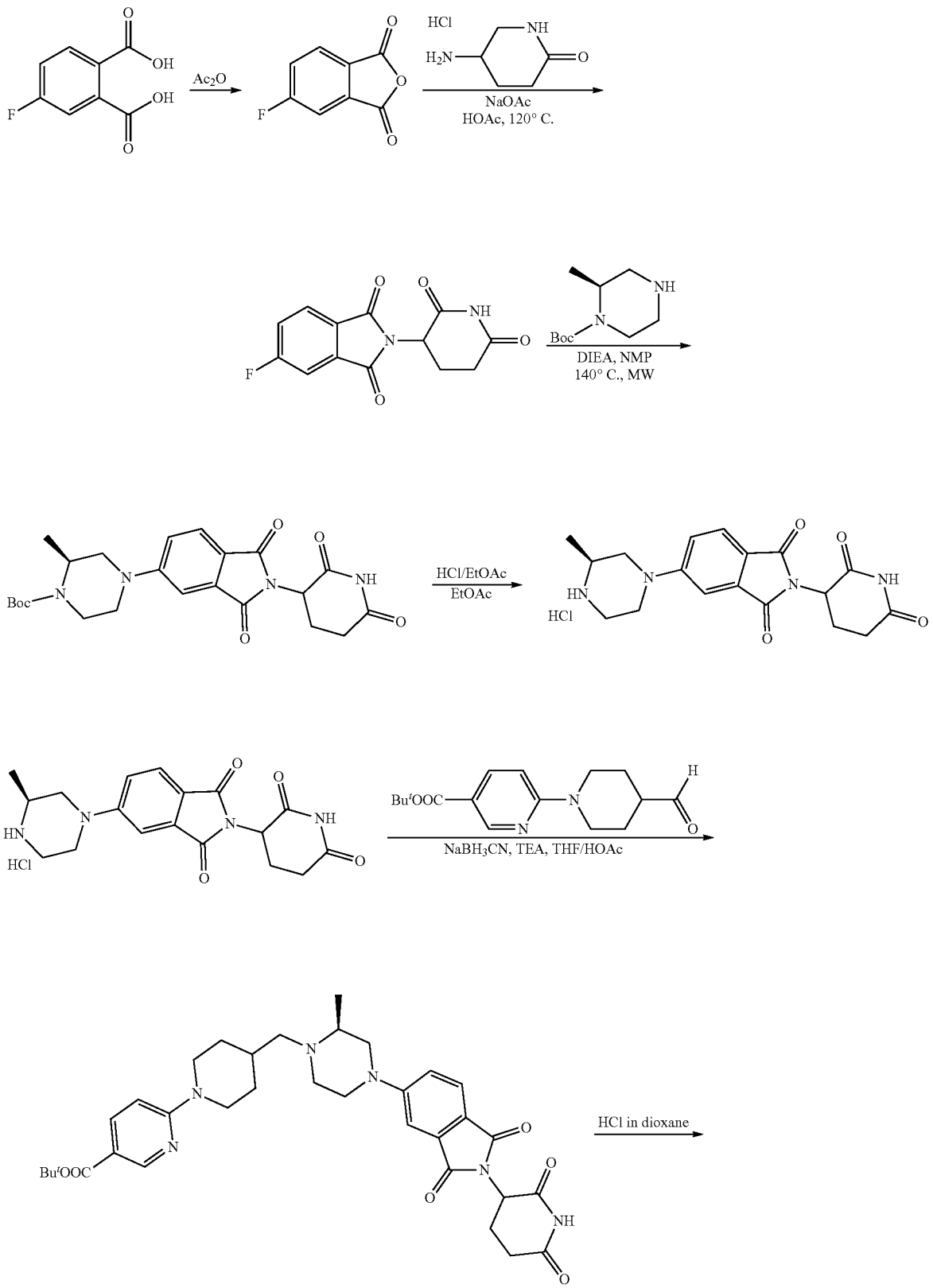

-continued
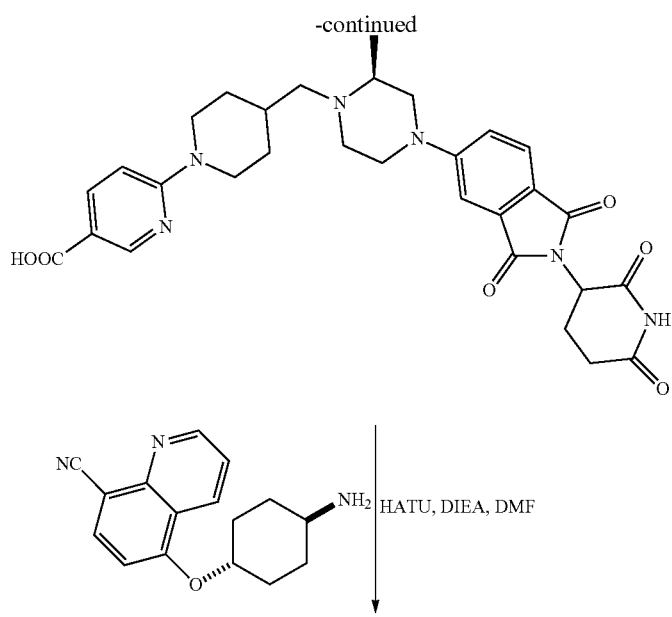
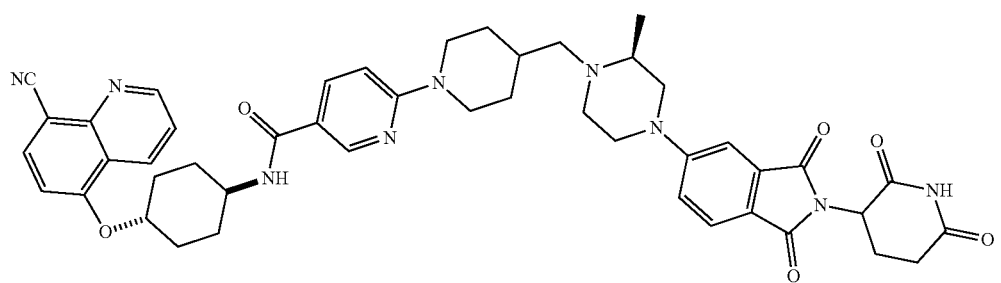
Compounds 3-38, 3-39 and 3-40 can be prepared using the same route described in Scheme 9.

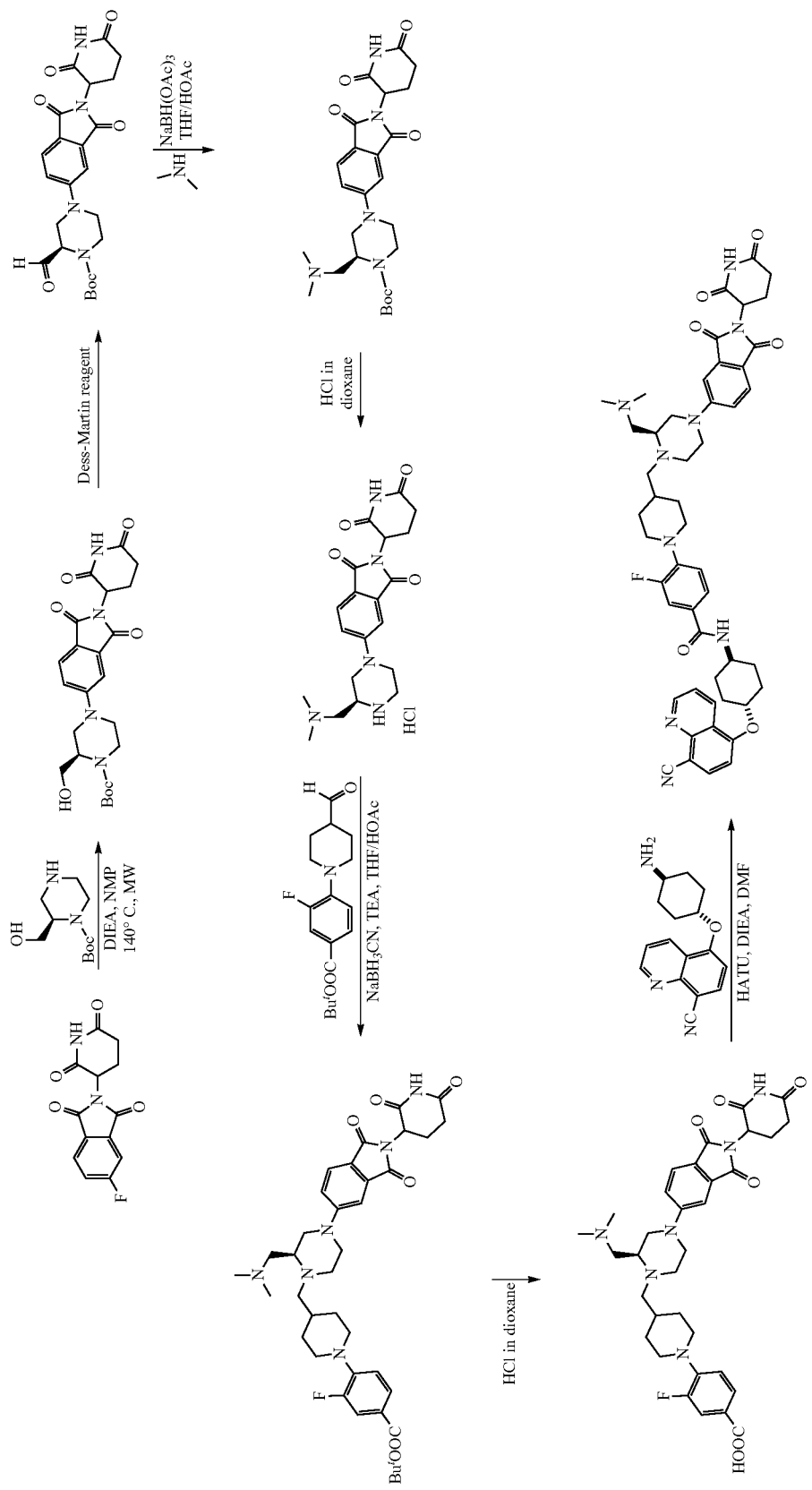

Compounds 3-42, 3-45 and 3-46 can be synthesized using the same method.
Scheme 11 Synthesis of 3-44.
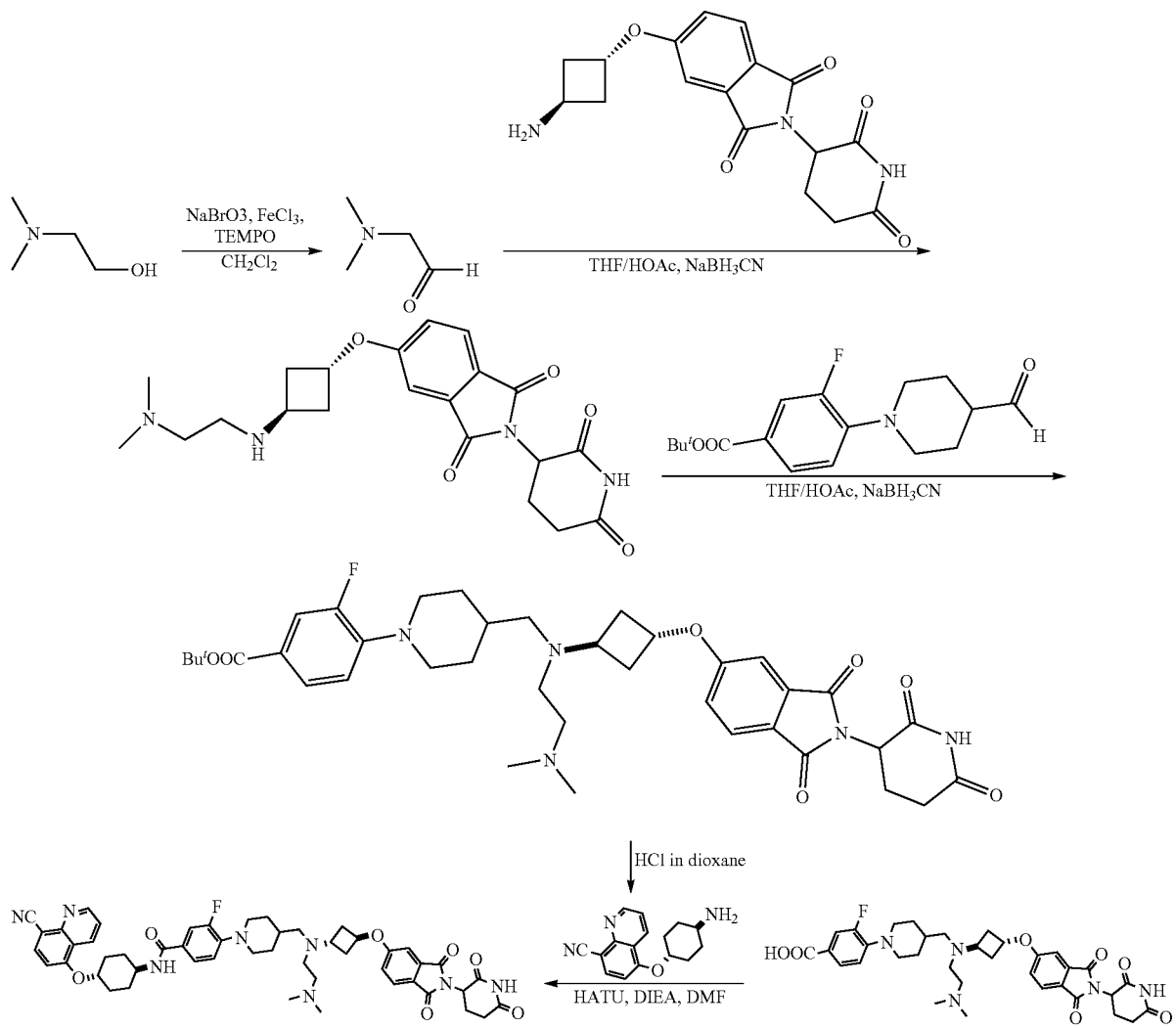
Preparation of Intermediates
Synthesis of trans-5-(4-aminocyclohexyl)oxyquinoline-8-carbonitrile Hydrochloride (Intermediate 1)
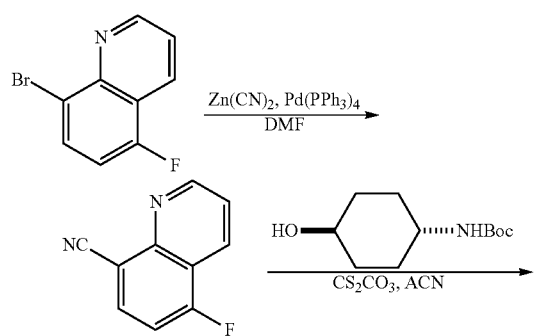
-continued
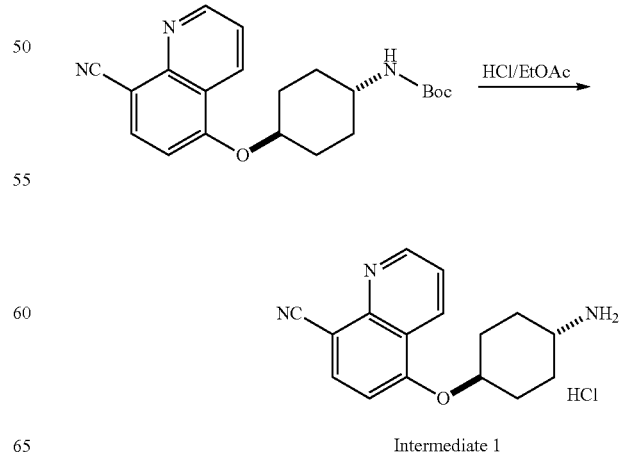
Intermediate 1

Step 1: Preparation of 5-fluoroquinoline-8-carbonitrile

A mixture containing 8-bromo-5-fluoroquinoline (2.00 g, 8.85 mmol, 1.00 eq), Pd(PPh₃)₄ (1.02 g, 884.7 umol, 0.10 eq) and Zn(CN)₂ (2.01 g, 17.1 mmol, 1.08 mL, 1.93 eq) was taken up into a microwave tube in DMF (20.0 mL). The sealed tube was heated at 150° C. for 0.5 h under microwave condition. TLC (petroleum ether/ethyl acetate=3/1, $R_f$ (starting material)=0.50, $R_f$ (product)=0.32) showed the starting material was consumed completely. Four reactions were repeated in parallel and the resulting reactions were combined for workup. The mixture was poured into water (300.0 mL), extracted with EtOAc (80.0 mL×2). The combined organic layers were washed with brine (150.0 mL), dried over Na₂SO₄, filtered and concentrated under reduce pressure to give a residue. The crude product was purified by column chromatography on silica gel eluted with petroleum ether/ethyl acetate (50/1 to 1/1) to provide the title compound (3.20 g, 52.1% yield) as a white solid. ¹H NMR (400 MHz, CDCl₃) δ 9.18 (dd, J=4.44, 1.65 Hz, 1H), 8.52 (dd, J=8.40, 1.65 Hz, 1H), 8.14 (dd, J=8.40, 5.51 Hz, 1H), 7.64 (dd, J=8.44, 4.30 Hz, 1H), 7.32 (t, J=8.40 Hz, 1H).

Step 2: Preparation of Tert-Butyl trans-4-((8-cyano-quinolin-5-yl)oxy)cyclohexylcarbamate To a mixture of 5-fluoroquinoline-8-carbonitrile (1.50 g, 8.71 mmol, 1.00 eq) and tert-butyl trans-4-hydroxycyclo-hexyl)carbamate (1.88 g, 8.71 mmol, 1.00 eq) in ACN (10.0 mL) was added Cs₂CO₃ (5.68 g, 17.4 mmol, 2.00 eq) in one portion at 15° C. under N₂. The mixture was stirred at 80° C. for 2 h. TLC (petroleum ether:ethyl acetate=1:1, $R_f$ (starting material)=0.65, $R_f$ (product)=0.47) showed the starting material was consumed completely. The mixture was filtered and the cake was washed with EtOAc (30.0 mL). The combined organic layers were concentrated in vacuum. The crude product was purified by column chromatography on silica gel eluted with petroleum ether/ethyl acetate (30:1 to 1:1) to provide the title compound (1.90 g, 59.4% yield) as a yellow solid.

Step 3: Preparation of trans-5-((4-aminocyclohexyl)oxy)quinoline-8-carbonitrile Hydrochloride (Intermediate 1)

To a solution of tert-butyl trans-4-((8-cyanoquinolin-5-yl)oxy)cyclohexylcarbamate (1.90 g, 5.17 mmol, 1.00 eq) in DCM (5.00 mL) was added HCl (g)/EtOAc (4.00 M, 20.0 mL, 15.4 eq) at 0° C. for 0.5 h. TLC (petroleum ethyl/ether acetate=1/1, $R_f$ (starting material)=0.54, $R_f$ (product)=0) showed the starting material was consumed completely. The mixture was filtered and the cake was washed with DCM (10.0 mL), dried in vacuum to provide the title compound (1.06 g, 3.40 mmol, 65.7% yield, 97.5% purity, HCl salt) as a yellow solid. LC/MS: 268.1 (M+H)+; ¹H NMR: ET26887-10-P1A (400 MHz, MeOD) δ 9.14-9.18 (m, 2H), 8.40 (d, J=8.48 Hz, 1H), 7.92-7.97 (m, 1H), 7.47 (d, J=8.44 Hz, 1H), 4.81-4.87 (m, 1H), 3.24-3.30 (m, 1H), 2.37-2.46 (m, 2H), 2.21 (br d, J=12.44 Hz, 2H), 1.67-1.87 (m, 4H).

Synthesis of 2-(2,6-dioxopiperidin-3-yl)-5-(piperazin-1-yl)isoindoline-1,3-dione (Intermediate 2-1)

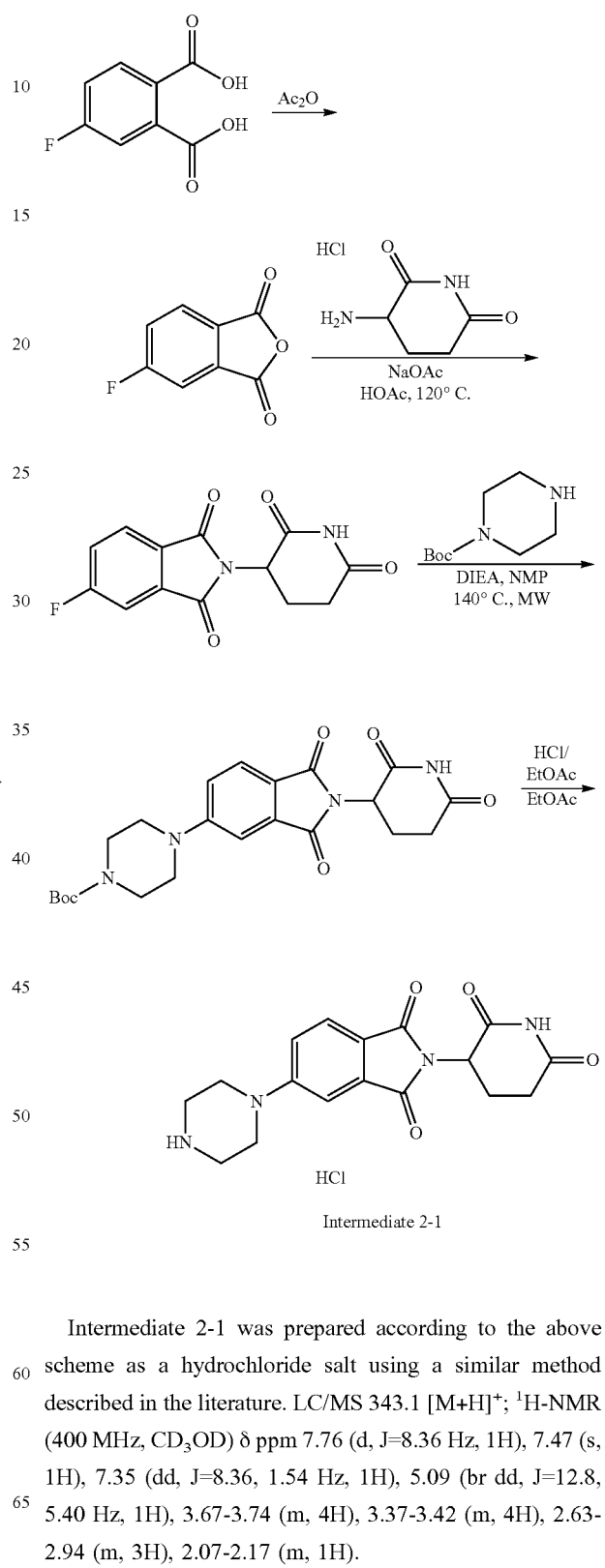

Intermediate 2-1

Intermediate 2-1 was prepared according to the above scheme as a hydrochloride salt using a similar method described in the literature. LC/MS 343.1 [M+H]⁺; ¹H-NMR (400 MHz, CD₃OD) δ ppm 7.76 (d, J=8.36 Hz, 1H), 7.47 (s, 1H), 7.35 (dd, J=8.36, 1.54 Hz, 1H), 5.09 (br dd, J=12.8, 5.40 Hz, 1H), 3.67-3.74 (m, 4H), 3.37-3.42 (m, 4H), 2.63-2.94 (m, 3H), 2.07-2.17 (m, 1H).

Synthesis of (S)-3-(1-oxo-5-(piperazin-1-yl)isoindo-lin-2-yl)piperidine-2,6-dione (Intermediate 2-2)

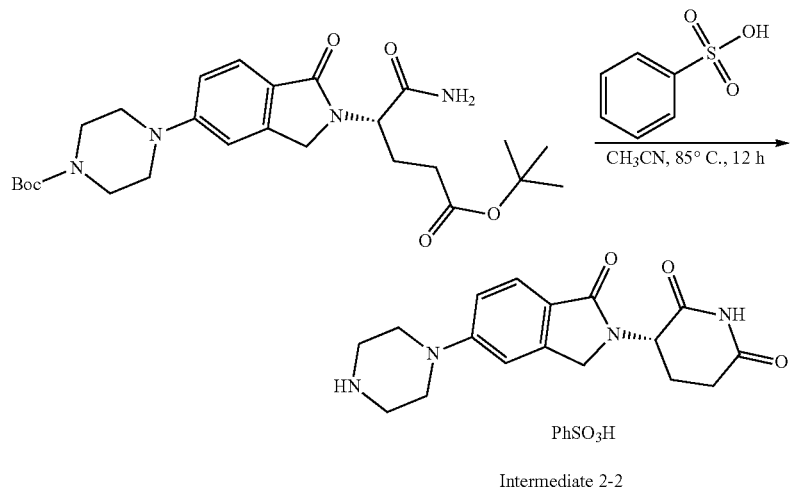

PhSO₃H

Intermediate 2-2

To a solution of (S)-tert-butyl 4-(2-(1-amino-5-tert-butoxy-1,5-dioxopentan-2-yl)-1-oxoisoindolin-5-yl)piperazine-1-carboxylate (5.8 g, 12 mol, prepared according to the same method as described in Intermediate 2-4 synthesis) in acetonitrile (90 mL) was added benzenesulfonic acid (3.64 g, 23 mol). The mixture was stirred at 85° C. for 12 h. LC/MS showed the reaction was complete. The mixture was concentrated in vacuum. The residue was triturated with ethyl acetate to afford (S)-3-(1-oxo-5-(piperazin-1-yl)isoindolin-2-yl)piperidine-2,6-dione benzenesulfonate (5.2 g, 93%) as off-white solid. LC/MS 329.1 [M+1]⁺; ¹H NMR (400 MHz, DMSO-d6) δ 1.95-1.99 (m, 1H), 2.36-2.41 (m, 1H), 2.58-2.62 (d, 1H), 2.88-2.91 (m, 1H), 3.26 (s, 4H), 3.49-3.52 (m, 4H), 4.21-4.38 (dd, 2H), 5.05-5.10 (dd, 1H), 7.12-7.16 (m, 2H), 7.30-7.358 (m, 3H), 7.58-7.62 (m, 3H), 8.72 (s, 2H).

Synthesis of 2-(2,6-dioxopiperidin-3-yl)-5-fluoro-6-(piperazin-1-yl)isoindoline-1,3-dione (Intermediate 2-3)

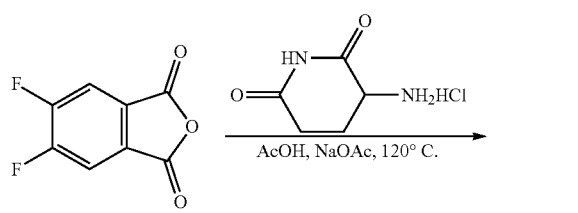

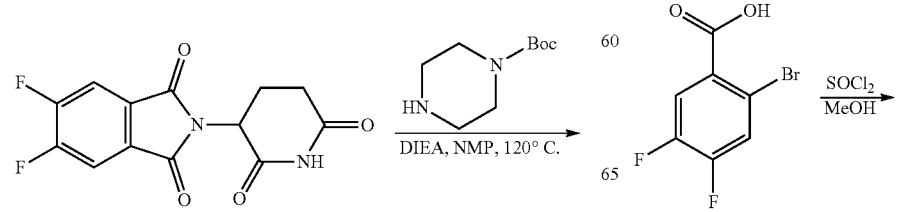

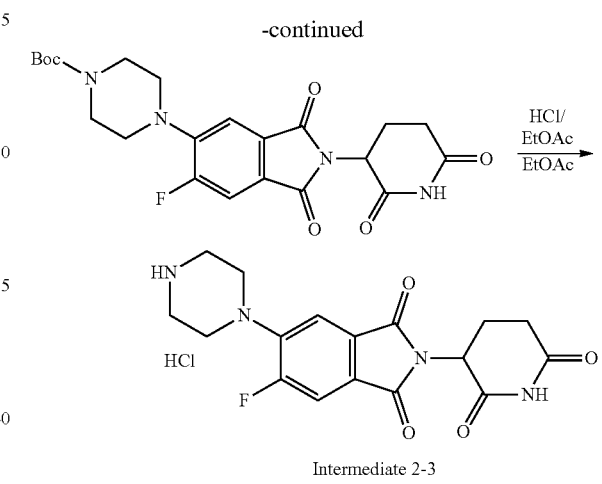

Intermediate 2-3

Intermediate 2-3 was prepared according to the above scheme as a hydrochloride salt. LC/MS 361.1 [M+1]±; ¹H NMR (400 MHz, DMSO-d6) δ 11.1 (s, 1H), 9.49 (br s, 2H), 7.79 (d, J=11.2 Hz, 1H), 7.57 (br d, J=7.32 Hz, 1H), 5.12 (br dd, J=12.4, 5.32 Hz, 1H), 3.50 (br s, 4H), 3.24 (br s, 4H), 2.80-2.95 (m, 1H), 2.52-2.69 (m, 2H), 1.97-2.10 (m, 1H).

Synthesis of (S)-3-(6-fluoro-1-oxo-5-(piperazin-1-yl)isoindolin-2-yl)piperidine-2,6-dione (Intermediate 2-4)

-continued

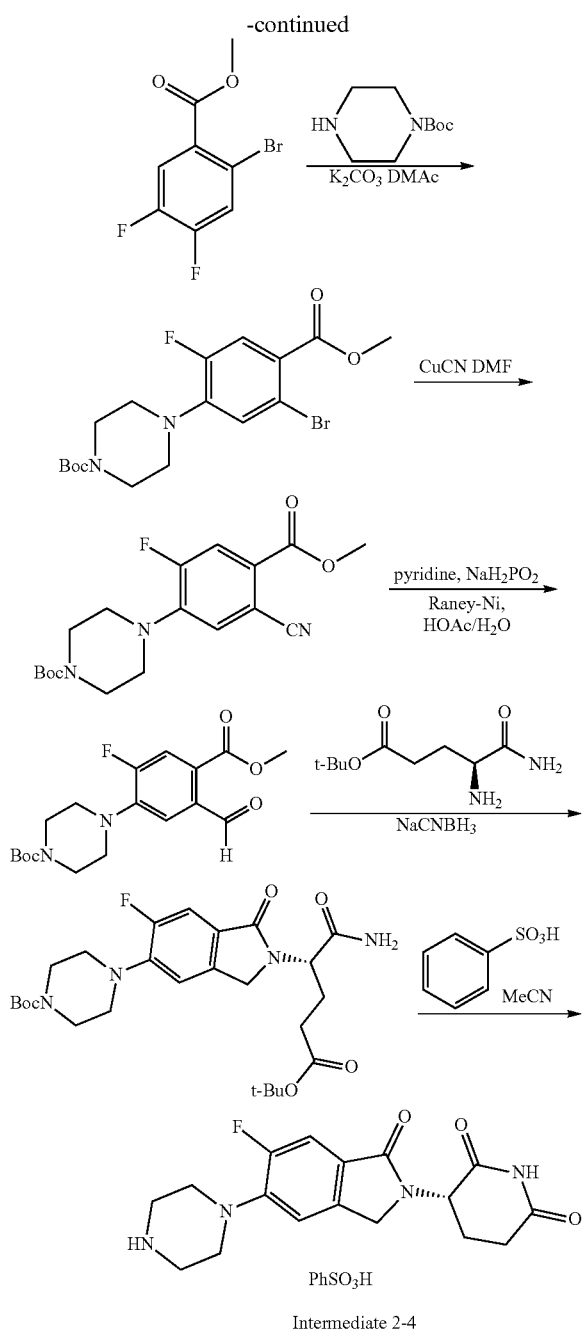

Intermediate 2-4

Step 1: Preparation of methyl 2-bromo-4,5-difluorobenzoate

Thionyl chloride (130 g, 1.09 mol) was added slowly to a mixture of 2-bromo-4,5-difluorobenzoic acid (200 g, 0.84 mol) in MeOH (600 mL) at 10° C., the mixture was stirred at 80° C. for 3 h. TLC showed the reaction was completed. The mixture was cooled to room temperature, concentrated, then partitioned between ethyl acetate and water. The organic layer was washed with saturated $Na_2CO_3$ and brine twice, dried over $Na_2SO_4$ and concentrated to afford a crude methyl 2-bromo-4,5-difluorobenzoate (210 g, yield: 100%) which was used for the next step without further purification.

Step 2: Preparation of tert-butyl 4-(5-bromo-2-fluoro-4-(methoxycarbonyl)phenyl) piperazine-1-carboxylate A mixture of methyl 2-bromo-4,5-difluorobenzoate (210 g, 0.84 mol), tert-butyl piperazine-1-carboxylate (234 g, 1.25 mol) and $K_2CO_3$ (173 g, 1.25 mol) in N,N-dimethylacetamide (600 mL) was stirred at 80° C. for 16 h. TLC showed the reaction was completed. The mixture was added to water (2 L) and stirred for 10 min followed by the addition of ethyl acetate. The mixture was partitioned between ethyl acetate and water. The organic layer was washed with water, brine, dried over $Na_2SO_4$ and concentrated to afford tert-butyl 4-(5-bromo-2-fluoro-4-(methoxycarbonyl)phenyl)piperazine-1-carboxylate (315.8 g, yield: 90%).

Step 3: Preparation of tert-butyl 4-(5-cyano-2-fluoro-4-(methoxycarbonyl)phenyl) piperazine-1-carboxylate A mixture of tert-butyl 4-(5-bromo-2-fluoro-4-(methoxycarbonyl)phenyl)piperazine-1-carboxylate (306 g, 0.73 mol) and CuCN (98 g, 1.09 mol) in DMF (1.2 L) was stirred at 100° C. for 16 h. TLC showed the reaction was completed. The mixture was cooled to room temperature. Ethyl acetate (2 L) and ammonium hydroxide (2 L) were added and the mixture was stirred for 30 min. The mixture was filtered. The organic layer was washed with water, dried over $Na_2SO_4$ and concentrated to afford a crude product (254 g). This crude product was taken into petroleum ether (1 L) at reflux. The mixture was filtered and dried in oven at 50° C. to afford tert-butyl 4-(5-cyano-2-fluoro-4-(methoxycarbonyl)phenyl)piperazine-1-carboxylate (215 g, yield: 81%).

Step 4: Preparation of tert-butyl 4-(2-fluoro-5-formyl-4-(methoxycarbonyl)phenyl) piperazine-1-carboxylate To a solution of pyridine (391 g, 4.95 mol), water (200 mL), acetic acid (264 g, 4.4 mol) was added tert-butyl 4-(5-cyano-2-fluoro-4-(methoxycarbonyl)phenyl)piperazine-1-carboxylate (200 g, 0.55 mol) and Raney-nickel (85% in water, 100 g) at room temperature. The resulting mixture was heated to 60° C. Sodium hypophosphite (292 g in 500 mL water) was added dropwise into the mixture. The mixture was stirred for 16 h at 60° C. TLC showed the reaction not completed. The mixture was further stirred for 10 h. The mixture was cooled to room temperature. Ethyl acetate and water were added. The mixture was filtered. The organic layer was washed with water, 1N HCl and brine, dried over $Na_2SO_4$ and concentrated under reduced pressure to afford a crude product (208 g, crude) which was further purified by silica-gel pad to provide 4-(2-fluoro-5-formyl-4-(methoxycarbonyl)phenyl)piperazine-1-carboxylate (86.5 g, yield: 43%).

Step 5: Preparation of tert-butyl (S)-4-(2-(1-amino-5-(tert-butoxy)-1,5-dioxopentan-2-yl)-6-fluoro-1-oxoisoindolin-5-yl)piperazine-1-carboxylate To a solution of tert-butyl 4-(2-fluoro-5-formyl-4-(methoxycarbonyl)phenyl)piperazine-1-carboxylate (81.5 g, 0.22 mol) in methanol (500 mL) was added tert-butyl (S)-4,5-diamino-5-oxopentanoate (54 g, 0.27 mol) at room temperature. Acetic acid (19.8 g, 0.33 mol) was added at 0° C. followed by the addition of sodium cyanoborohydride (27.6 g, 0.44 mol) slowly. The mixture was stirred at room temperature for 16 hours. TLC showed the reaction was completed. The mixture was concentrated and partitioned between ethyl acetate and water. The organic layer was washed with saturated citric acid, brine, dried over $Na_2SO_4$ and concentrated under reduced pressure to afford a crude product which was further purified by silica-gel pad to give tert-butyl (S)-4-(2-(1-amino-5-(tert-butoxy)-1,5-dioxopentan-2-yl)-6-fluoro-1-oxoisoindolin-5-yl)piperazine-1-carboxylate (80 g, yield: 69%).

Step 6: Preparation of (S)-3-(6-fluoro-1-oxo-5-(piperazin-1-yl)isoindolin-2-yl)piperidine-2,6-dione Benzenesulfonic Acid (Intermediate 2-4)

To a solution of (S)-4-(2-(1-amino-5-(tert-butoxy)-1,5-dioxopentan-2-yl)-6-fluoro-1-oxoisoindolin-5-yl)piperazine-1-carboxylate (67 g, 0.13 mol) in acetonitrile (670 mL) was added benzenesulfonic acid (43 g, 0.26 mol). The mixture was stirred at 80° C. for 16 h. LCMS showed the reaction was complete. The mixture was cooled to room temperature. The mixture was filtered and dried to afford (S)-3-(6-fluoro-1-oxo-5-(piperazin-1-yl)isoindolin-2-yl)piperidine-2,6-dione benzenesulfonic acid (56 g, 86%) as off-white solid. $^1$H NMR (400 MHz, DMSO-d6) δ 1.94-1.99 (m, 1H), 2.35-2.43 (m, 1H), 2.58-2.62 (m, 1H), 2.88-2.91 (m, 1H), 3.30 (br s, 8H), 4.38 (d, J=17.2 Hz, 1H), 4.26 (d, J=17.2 Hz, 1H), 5.08 (dd, J=13.2, 5.2 Hz, 1H), 7.29-7.35 (m, 4H), 7.49 (d, J=8.7 Hz, 1H), 7.60 (m, 2H), 8.72 (br s, 2H), 10.99 (s, 1H). LCMS m/z 347.3 [M+1]$^+$.

Preparation of Example Compounds

All final compounds of examples described in this section and in Table 2 were checked for purity by HPLC and compounds were detected at the wavelength of 214 nM and 254 nM. Purities for all final compounds were over 95% based on HPLC peak analysis (214 nM and 254 nM wavelength). H-NMR was obtained on Bruker NMR spectrometer (400 MHz). LC/MS was performed on Agilent 6125 under the following condition: column, Waters CORTECS C18, 27 um, 4.6×30 mm; mobile phase, ACN (0.05% TFA) and water (0.05 TFA); gradient: 5% ACN to 95% ACN in 1.0 min, hold 1.0 min, total 2.5 min; flow rate 1.8 mL/min; column temperature 45° C. Analytical HPLC was performed on SHIMADZU LC-2010A under the following conditions: column, XBRIDGE 3.5 um, 2.1×50 mm; mobile phase, water (0.05% TFA) and ACN (0.05% TFA); gradient, ACN from 10% to 100% over 7 minutes, hold 1 min; column oven temperature, 45° C.; flow rate, 0.8 ml/min.

Synthesis of trans-N-(4-((8-cyanoquinolin-5-yl)oxy) cyclohexyl)-6-(4-((4-(2-(2,6-dioxopiperidin-3-yl)-1, 3-dioxoisoindolin-5-yl)piperazin-1-yl)methyl)piperidin-1-yl)nicotinamide (3-13)

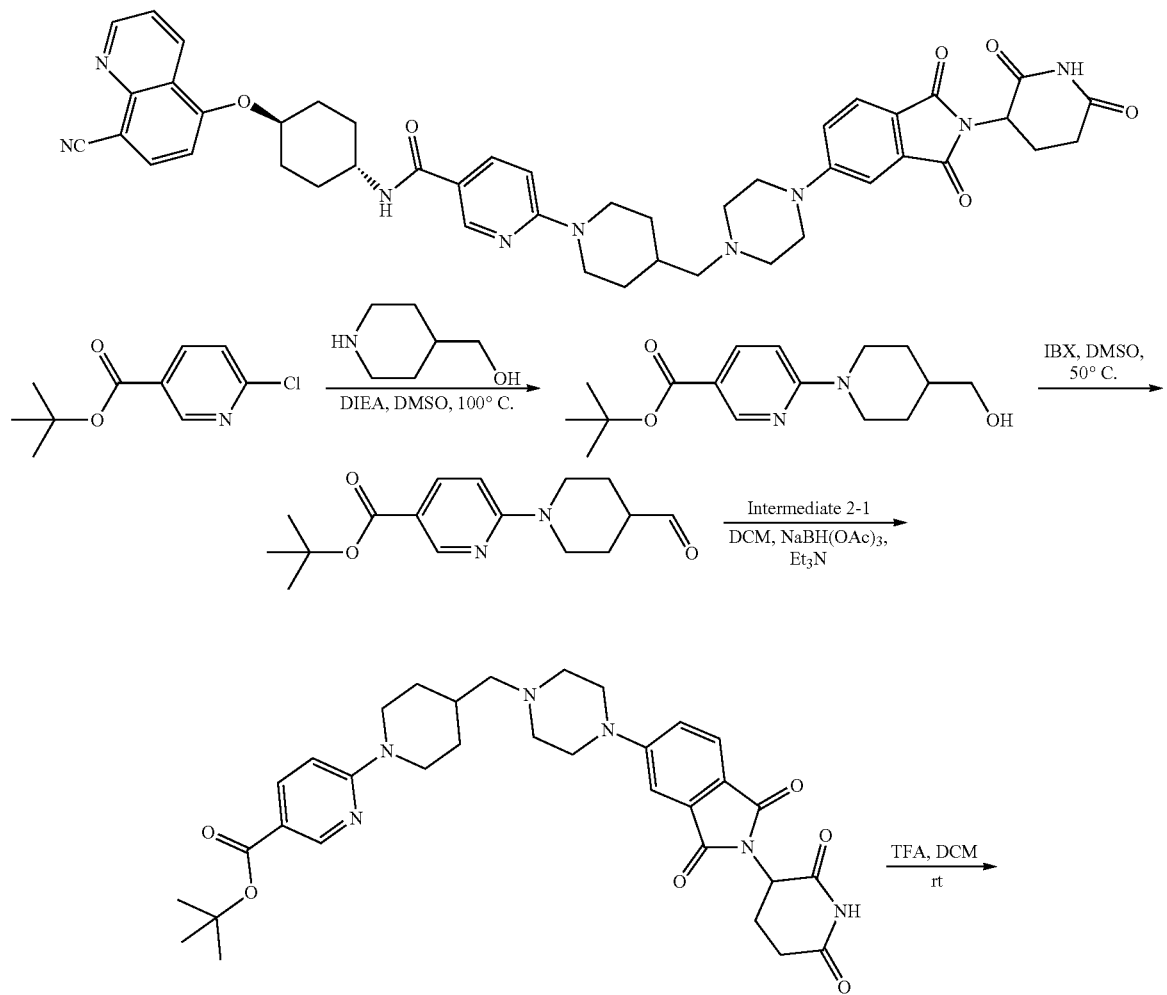

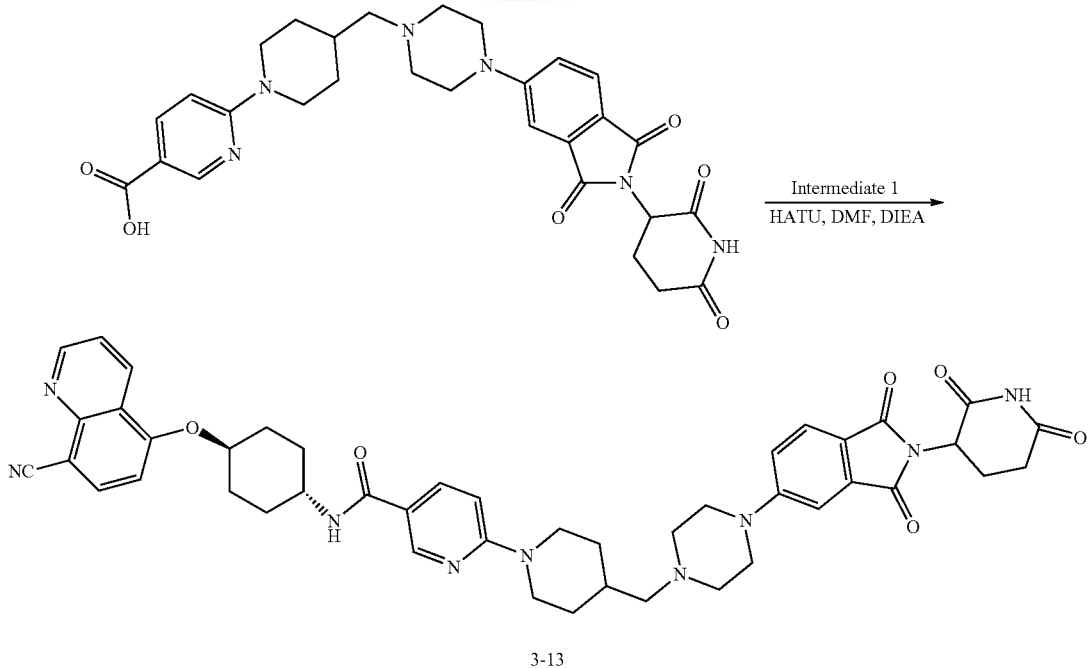

3-13

Step 1: Preparation of tert-butyl 6-(4-(hydroxymethyl)piperidin-1-yl)nicotinate A mixture of tert-butyl 6-chloronicotinate (500 mg, 2.35 mmol), piperidin-4-ylmethanol (297 mg, 2.58 mmol) and DIEA (606 mg, 4.70 mmol) in DMSO (10 mL) was stirred at 100° C. overnight. TLC showed the reaction completed. The mixture was partitioned between EA and H$_2$O. The organic phase was washed with brine, dried over magnesium sulfate and evaporated to dryness. The crude product was purified by silica gel chromatography (10-50% EtOAc in hexane as eluent) to afford the desired compound (400 mg, 58.3%). LC/MS: 293.2 [M+H]$^+$.

Step 2: Preparation of tert-butyl 6-(4-formylpiperidin-1-yl)nicotinate

A mixture of tert-butyl 6-(4-(hydroxymethyl)piperidin-1-yl)nicotinate (574 mg, 1.97 mmol) and IBX (658 mg, 2.35 mmol) in DMSO (10 mL) was stirred at 50° C. overnight. TLC showed the reaction completed. The mixture was partitioned between EA and H$_2$O. The organic phase was washed with brine, dried over magnesium sulfate and evaporated to dryness. The crude product was purified by silica gel chromatography with 10-50% EtOAc in hexane as eluent to afford the desired compound (400 mg, 70%). LC/MS: 291.0 [M+H]$^+$.

Step 3: Preparation of tert-butyl 6-(4-((4-(2-(2,6-dioxopiperidin-3-yl)-1,3-dioxoisoindolin-5-yl)piperazin-1-yl)methyl)piperidin-1-yl)nicotinate To a solution of tert-butyl 6-(4-formylpiperidin-1-yl)nicotinate (200 mg, 0.69 mmol), intermediate 2-1 (260 mg, 0.68 mmol), MgSO$_4$ (820 mg, 6.8 mmol) in dichloromethane (10 mL) was added Et$_3$N (140 mg, 1.36 mmol). The mixture was stirred at room temperature for 1 hour. Then the sodium triacetoxyborohydride (430 mg, 2.04 mmol) was added slowly to the mixture. The mixture was stirred at room temperature overnight. The residue was concentrated in vacuum. The crude product was purified by silica gel chromatography using 5-10% MeOH in DCM as eluent to afford the desired compound (250 mg, 59%). LC/MS: 617.3 [M+H]$^+$.

Step 4: Preparation of 6-(4-((4-(2-(2,6-dioxopiperidin-3-yl)-1,3-dioxoisoindolin-5-yl)piperazin-1-yl)methyl)piperidin-1-yl)nicotinic Acid To a solution of tert-butyl 6-(4-((4-(2-(2,6-dioxopiperidin-3-yl)-1,3-dioxoisoindolin-5-yl)piperazin-1-yl)methyl)piperidin-1-yl)nicotinate (230 mg, 0.37 mmol) in dichloromethane (10 mL) was added TFA (2 mL). The mixture was stirred at room temperature for overnight. The residue was concentrated in vacuum. The crude product was used in next step without further purification. LC/MS: 561.1 [M+H]$^+$.

Step 5: Preparation of trans-N-(4-((8-cyanoquinolin-5-yl)oxy)cyclohexyl)-6-(4-((4-(2-(2,6-dioxopiperidin-3-yl)-1,3-dioxoisoindolin-5-yl)piperazin-1-yl)methyl)piperidin-1-yl)nicotinamide (3-13)

A solution of 6-(4-((4-(2-(2,6-dioxopiperidin-3-yl)-1,3-dioxoisoindolin-5-yl)piperazin-1-yl)methyl)piperidin-1-yl) nicotinic acid (130 mg, crude), Intermediate 1 (84 mg, 0.28 mmol), HATU (105 mg, 0.27 mmol) and DIEA (200 mg, 1.55 mmol) in DMF (7 mL) was stirred at room temperature overnight. TLC showed the reaction completed. The mixture was partitioned between EA and H$_2$O. The organic phase was washed with brine, dried over magnesium sulfate and evaporated to dryness. The crude product was purified by preparative TLC (MeOH:DCM=1:15) to afford the desired compound (54 mg, 24%). LC/MS: 810.3 [M+H]$^+$; $^1$H NMR (400 MHz, DMSO) δ 11.10 (s, 1H), 9.08 (dd, J=4.2, 1.7 Hz, 1H), 8.68-8.59 (m, 2H), 8.31 (t, J=7.2 Hz, 1H), 8.06 (d, J=7.5 Hz, 1H), 7.96 (dd, J=9.0, 2.4 Hz, 1H), 7.70 (dd, J=8.5, 4.5 Hz, 2H), 7.37 (d, J=8.6 Hz, 2H), 7.27 (d, J=8.7 Hz, 1H), 6.84 (d, J=9.1 Hz, 1H), 5.08 (dd, J=12.8, 5.4 Hz, 1H), 4.75 (m, 1H), 4.41 (d, J=13.1 Hz, 2H), 3.88 (m, 1H), 3.45 (br s, 4H), 3.32 (br s, 1H), 2.96-2.83 (m, 4H), 2.70-2.45 (m, 4H), 2.35-2.15 (m, 4H), 2.08-1.91 (m, 3H), 1.89-1.77 (m, 3H), 1.69-1.55 (m, 4H), 1.30-1.10 (m, 2H).

Synthesis of trans-N-(4-((8-cyanoquinolin-5-yl)oxy)
cyclohexyl)-2-(4-((4-(2-(2,6-dioxopiperidin-3-yl)-1,
3-dioxoisoindolin-5-yl)piperazin-1-yl)methyl)piperi-
din-1-yl)pyrimidine-5-carboxamide (3-15)
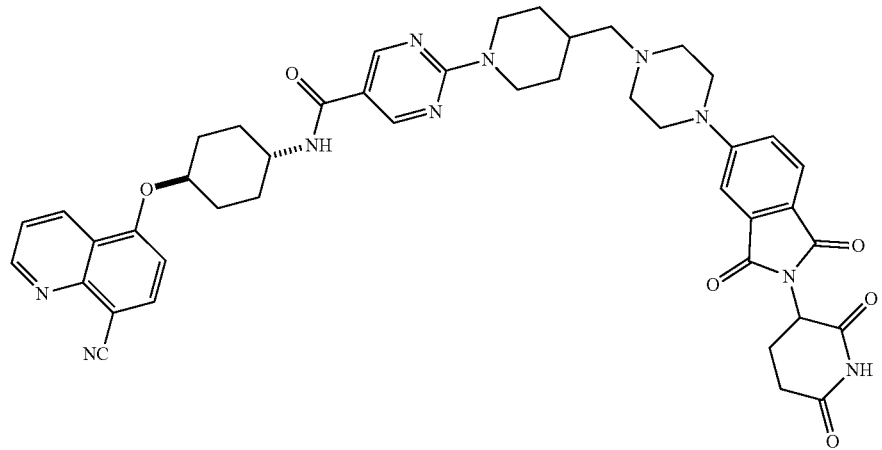
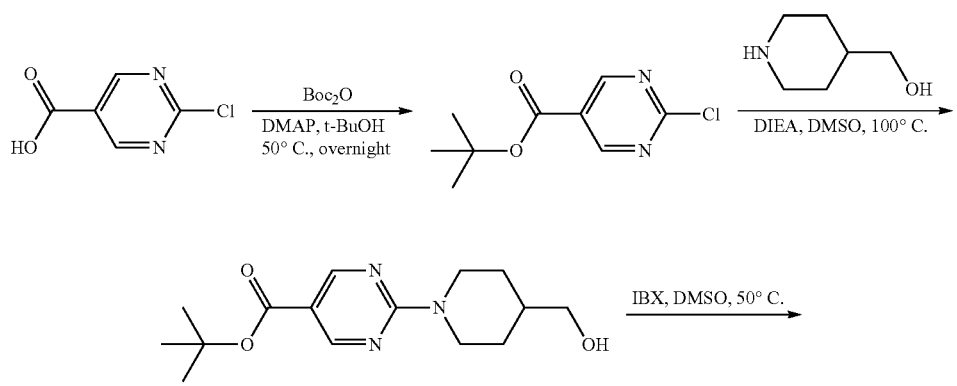
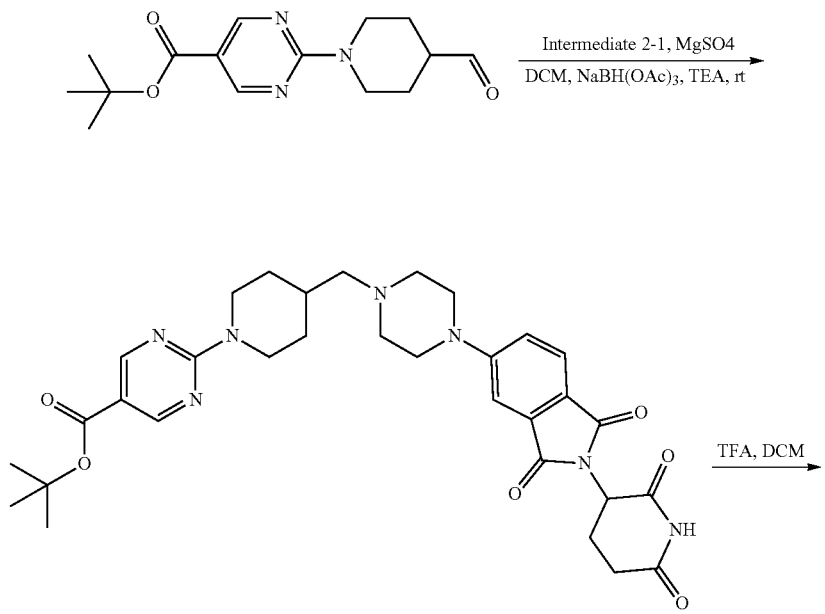

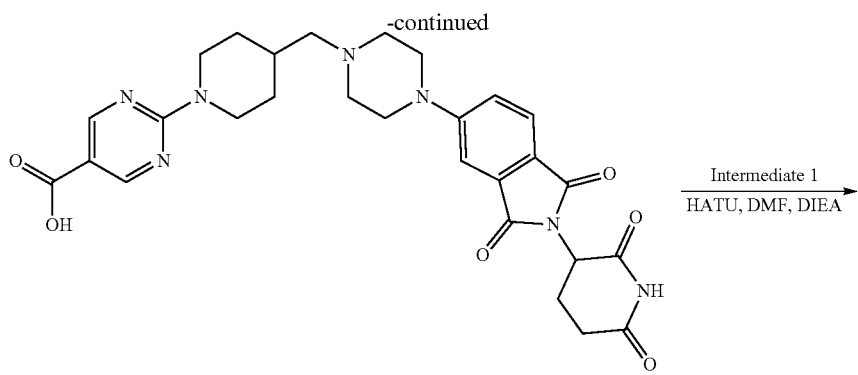

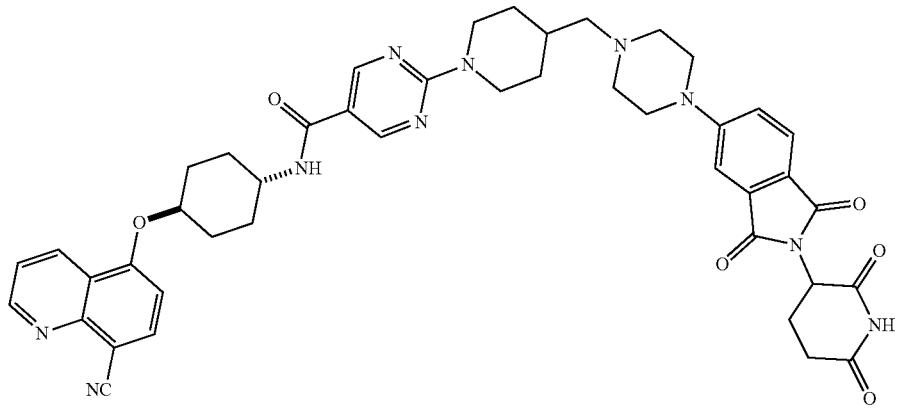

3-15

Step 1: Preparation of tert-butyl 2-chloropyrimidine-5-carboxylate

A mixture of 2-chloropyrimidine-5-carboxylic acid (2 g, 12.6 mmol), DMAP (154 mg, 1.26 mmol) and Boc$_2$O (5.5 g, 25.2 mmol) in t-BuOH (10 mL) was stirred at 50° C. overnight. TLC showed the reaction completed. The organic phase was evaporated to dryness. The crude product was purified by silica gel chromatography (10-70% EtOAc in hexane as eluent) to afford the desired compound (800 mg, 29%). LC/MS: 215.2 [M+H]$^+$.

Step 2 through Step 6 were performed according to the same procedure as described in the preparation of 3-13.

The desired compound 3-15 was obtained following preparative TLC (MeOH:DCM=1:20). LC/MS: 811.3 [M+H]$^+$;

$^1$H NMR (400 MHz, DMSO) δ 11.12 (s, 1H), 9.08 (dd, J=4.1, 1.3 Hz, 1H), 8.80 (s, 2H), 8.69-8.61 (m, 1H), 8.31 (d, J=8.3 Hz, 1H), 8.19 (d, J=7.5 Hz, 1H), 7.79 (d, J=8.5 Hz, 1H), 7.70 (dd, J=8.6, 4.3 Hz, 1H), 7.52 (s, 1H), 7.38 (t, J=7.4 Hz, 2H), 5.11 (dd, J=12.8, 5.4 Hz, 1H), 4.76 (br d, J=13.0 Hz, 2H), 4.23 (br d, J=12.1 Hz, 3H), 3.88 (m, 1H), 3.40-3.27 (m, 2H), 3.27-2.95 (m, 6H), 2.97-2.82 (m, 1H), 2.70-2.53 (m, 2H), 2.45-2.14 (m, 4H), 2.13-1.92 (m, 3H), 1.91-1.79 (m, 3H), 1.73-1.51 (m, 4H), 1.35-1.06 (m, 2H).

Synthesis of trans-N-(4-((8-cyanoquinolin-5-yl)oxy)cyclohexyl)-6-(4-((4-(2-(2,6-dioxopiperidin-3-yl)-1,3-dioxoisoindolin-5-yl)piperazin-1-yl)methyl)piperidin-1-yl)pyridazine-3-carboxamide (3-16)

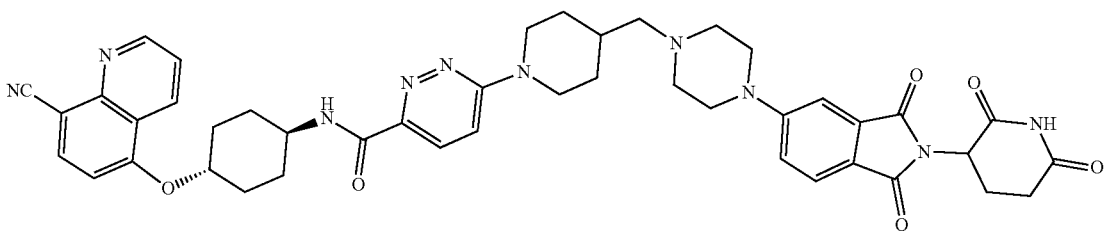 [SMILES: N#Cc1ccc(O[C@H]2CC[C@H](NC(=O)c3ccc(N4CCC(CN5CCN(c6ccc7c(c6)C(=O)N(C6CCC(=O)NC6=O)C7=O)CC5)CC4)nn3)CC2)c2cccnc12]

This compound was prepared using the same method as described for 3-13 except that tert-butyl 6-chloropyridazine-3-carboxylate was used. The final crude product was purified by preparative TLC to afford the desired compound (60 mg, 27%). LC/MS: 810.7 [M+H]⁺; ¹H NMR (300 MHz, DMSO) δ 11.04 (s, 1H), 9.03 (dd, J=4.2, 1.7 Hz, 1H), 8.65-8.55 (m, 2H), 8.25 (d, J=8.3 Hz, 1H), 7.78 (d, J=9.6 Hz, 1H), 7.66 (dd, J=8.4, 4.3 Hz, 2H), 7.36-7.28 (m, 3H), 7.29-7.19 (m, 1H), 5.10-4.99 (m, 1H), 4.80-4.62 (m, 1H), 4.56-4.39 (m, 2H), 3.99-3.83 (m, 1H), 3.43 (br s, 4H), 3.28 (br s, 1H), 3.08-2.96 (m, 2H), 2.88-2.79 (m, 1H), 2.75-2.67 (m, 1H), 2.62-2.45 (m, 4H), 2.27-2.18 (m, 4H), 1.97-1.79 (m, 6H), 1.73-1.60 (m, 4H), 1.20-1.08 (m, 2H).

Synthesis of N-(4-((8-cyanoquinolin-5-yl)oxy)cyclohexyl)-4-(4-((4-(2-(2,6-dioxopiperidin-3-yl)-1,3-dioxoisoindolin-5-yl)piperazin-1-yl)methyl)piperidin-1-yl)benzamide (3-18)

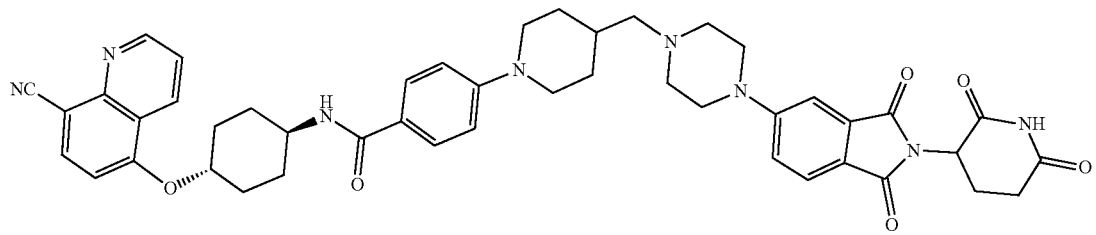 [SMILES: N#Cc1ccc(O[C@H]2CC[C@H](NC(=O)c3ccc(N4CCC(CN5CCN(c6ccc7c(c6)C(=O)N(C6CCC(=O)NC6=O)C7=O)CC5)CC4)cc3)CC2)c2cccnc12]

This compound was prepared using the same method as described for the preparation of 3-13 except that tert-butyl 4-fluorobenzoate was used. The final crude product was purified by preparative TLC with MeOH:DCM=1:10 to afford the desired compound (37 mg, 36%). LC/MS: 809.3 [M+H]⁺; ¹H NMR (400 MHz, DMSO) δ 11.10 (s, 1H), 9.08 (dd, J=4.2, 1.7 Hz, 1H), 8.65 (dd, J=8.5, 1.7 Hz, 1H), 8.30 (d, J=8.3 Hz, 1H), 8.01 (d, J=7.6 Hz, 1H), 7.79-7.66 (m, 3H), 7.37 (d, J=8.5 Hz, 2H), 7.27 (d, J=8.6 Hz, 1H), 6.95 (d, J=9.1 Hz, 2H), 5.08 (dd, J=13.0, 5.4 Hz, 1H), 4.74 (m, 1H), 3.86 (m, 3H), 3.46 (br s, 4H), 3.31 (br s, 1H), 2.84 (dt, J=24.2, 11.9 Hz, 2H), 2.77 (t, J=11.3 Hz, 2H), 2.65-2.50 (m, 4H), 2.36-2.17 (m, 4H), 2.08-1.89 (m, 3H), 1.82 (d, J=12.4 Hz, 3H), 1.74-1.52 (m, 4H), 1.28-1.10 (m, 2H).

Synthesis of N-(4-((8-cyanoquinolin-5-yl)oxy)cyclohexyl)-4-(4-((4-(2-(2,6-dioxopiperidin-3-yl)-1,3-dioxoisoindolin-5-yl)piperazin-1-yl)methyl)piperidin-1-yl)-3-fluorobenzamide (3-19)

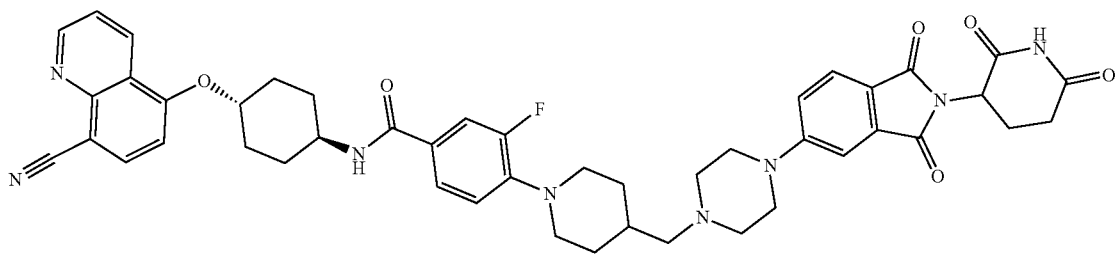

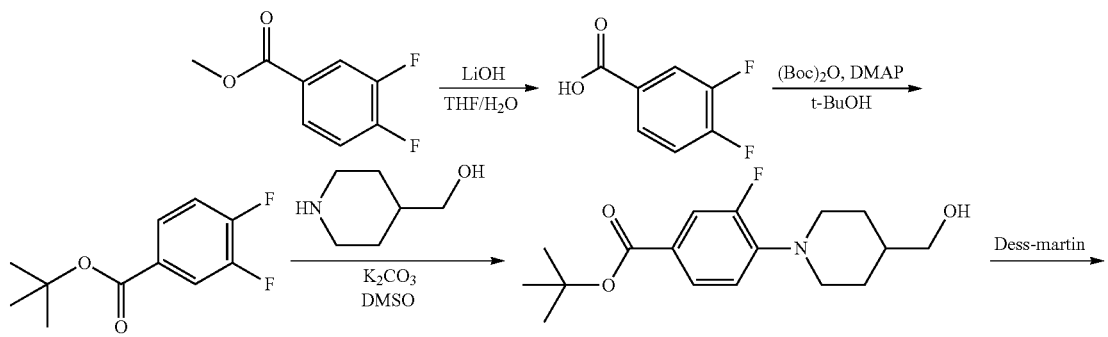

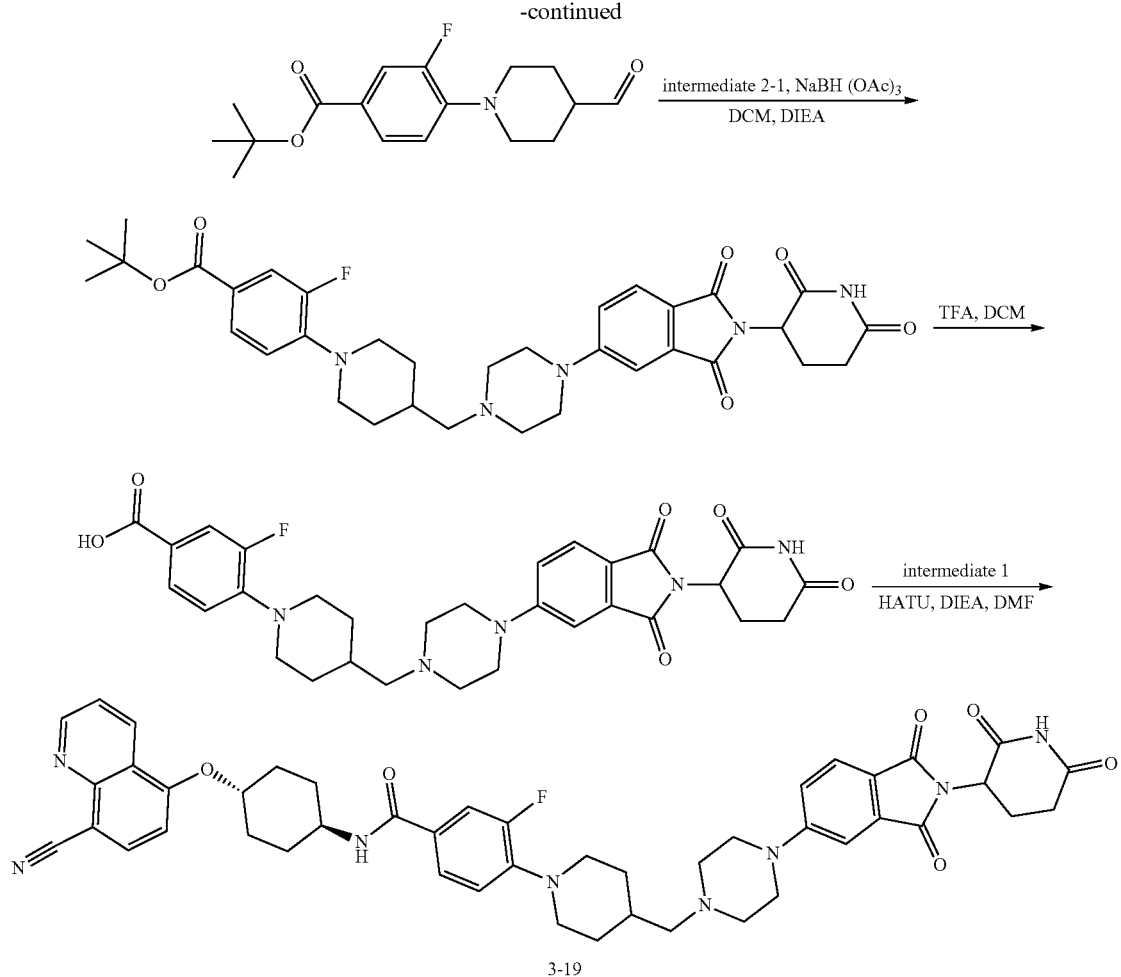

This compound was prepared using the similar method as described in the synthesis of 3-13. The final crude product was purified by prep-HPLC to give the title compound (60 mg, 42%). LC/MS: 826.7 [M+H]+; $^1$H NMR (400 MHz, DMSO) δ 11.10 (s, 1H), 9.08 (dd, J=4.2, 1.7 Hz, 1H), 8.65 (dd, J=8.5, 1.6 Hz, 1H), 8.30 (d, J=8.3 Hz, 1H), 8.20 (d, J=7.5 Hz, 1H), 7.68 (ddd, J=18.0, 11.1, 5.5 Hz, 4H), 7.37 (d, J=8.3 Hz, 2H), 7.28 (d, J=8.6 Hz, 1H), 7.08 (t, J=8.9 Hz, 1H), 5.09 (dd, J=12.8, 5.3 Hz, 1H), 4.75 (m, 1H), 3.88 (m, 1H), 3.60-3.40 (br s, 6H), 2.96-2.82 (m, 1H), 2.75 (t, J=11.3 Hz, 2H), 2.67-2.52 (m, 6H), 2.41-2.20 (m, 4H), 2.08-1.90 (m, 3H), 1.84 (d, J=12.8 Hz, 2H), 1.80-1.51 (m, 5H), 1.36-1.24 (m, 2H).

Synthesis of trans-N-(4-((8-cyanoquinolin-5-yl)oxy)cyclohexyl)-4-(4-((4-(2-((S)-2,6-dioxopiperidin-3-yl)-1-oxoisoindolin-5-yl)piperazin-1-yl)methyl)piperidin-1-yl)-3-fluorobenzamide (3-31)

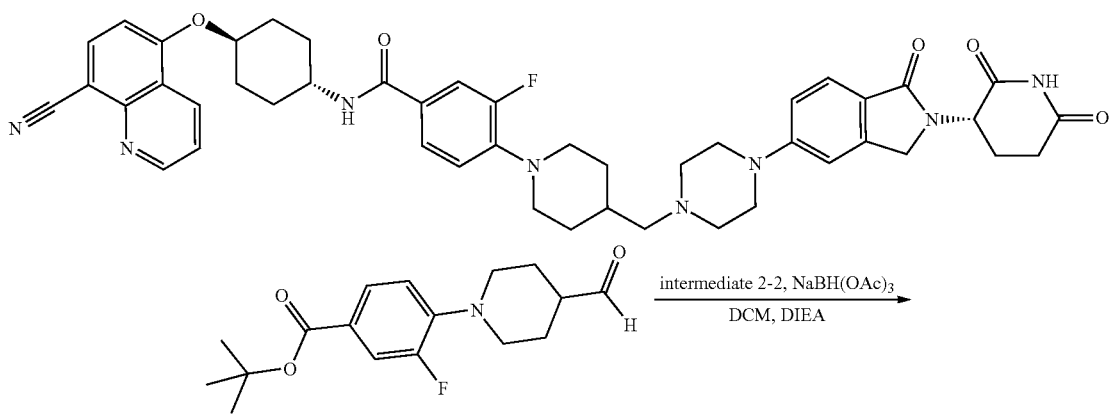

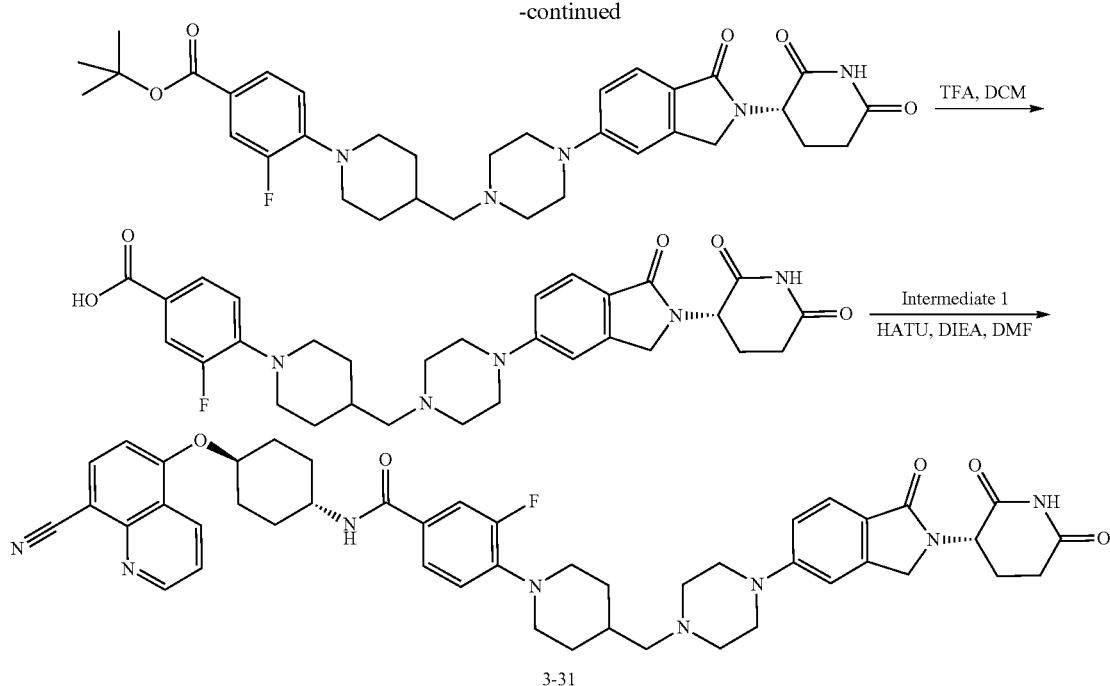

Step 1: Preparation of tert-butyl (S)-4-(4-((4-(2-(2,6-dioxopiperidin-3-yl)-1-oxoisoindolin-5-yl)piperazin-1-yl)methyl)piperidin-1-yl)-3-fluorobenzoate To a solution of tert-butyl 3-fluoro-4-(4-formylpiperidin-1-yl)benzoate (31 mg, 0.1 mmol) and intermediate 2-2 (48.6 mg, 0.1 mmol) in DCM (2 mL) stirred under nitrogen at room temperature was added magnesium sulphate (240 mg, 2 mmol) and triethylamine (20 mg, 0.2 mmol). The reaction mixture was stirred at room temperature for 1 hour. Then NaBH(OAc)$_3$ (53 mg, 0.25 mmol) was added in portions. The reaction was stirred for 1 hour. The solvent was removed in vacuum to give a crude product which was purified by silica gel column chromatography (eluted with 0-15% MeOH in DCM) to give the title compound (60 mg, 96%). LC/MS: 619.8 [M+H]$^+$.

Step 2: Preparation of (S)-4-(4-((4-(2-(2,6-dioxopiperidin-3-yl)-1-oxoisoindolin-5-yl)piperazin-1-yl)methyl)piperidin-1-yl)-3-fluorobenzoic Acid To the solution of (S)-4-(4-((4-(2-(2,6-dioxopiperidin-3-yl)-1-oxoisoindolin-5-yl)piperazin-1-yl)methyl)piperidin-1-yl)-3-fluorobenzoate (60 mg, 0.09 mmol) in DCM (2 mL) was added TFA (0.4 mL). The reaction was stirred for 16 hours. The solvent was removed in vacuum to give the product (55 mg, 100%). LC/MS: 563.7 [M+H]$^+$.

Step 3: Preparation of trans-N-(4-((8-cyanoquinolin-5-yl)oxy)cyclohexyl)-4-(4-((4-(2-((S)-2,6-dioxopiperidin-3-yl)-1-oxoisoindolin-5-yl)piperazin-1-yl)methyl)piperidin-1-yl)-3-fluorobenzamide (3-31)

This step of amide formation was performed using the same procedure as described in the last step (step 5) of the synthesis of 3-13. LC/MS: 812.5 [M+H]$^+$; $^1$H NMR (400 MHz, DMSO) δ 10.97 (s, 1H), 9.08 (dd, J=4.2, 1.7 Hz, 1H), 8.65 (dd, J=8.5, 1.6 Hz, 1H), 8.30 (d, J=8.3 Hz, 1H), 8.23 (br d, J=8.1 Hz, 1H), 7.69-7.65 (m, 3H), 7.51-7.62 (m, 1H), 7.36 (d, J=8.2 Hz, 1H), 7.04-7.23 (m, 3H), 5.06 (dd, J=13.2, 5.0 Hz, 1H), 4.75 (m, 1H), 4.35 (d, J=12.2 Hz, 1H), 4.23 (d, J=12.2 Hz, 1H), 3.90-3.80 (m, 1H), 3.49 (br d, J=8. Hz, 2H), 3.30-3.27 (br, 4H), 2.93-2.82 (m, 1H), 2.80-2.70 (m, 2H), 2.68-2.50 (m, 5H), 2.40-2.19 (m, 5H), 1.97 (m, 3H), 1.86-1.75 (m, 3H), 1.73-1.57 (m, 4H), 1.35-1.15 (m, 2H).

Synthesis of trans-N-(4-((8-cyanoquinolin-5-yl)oxy)cyclohexyl)-6-(4-((4-(2-((S)-2,6-dioxopiperidin-3-yl)-1-oxoisoindolin-5-yl)piperazin-1-yl)methyl)piperidin-1-yl)nicotinamide (3-29)

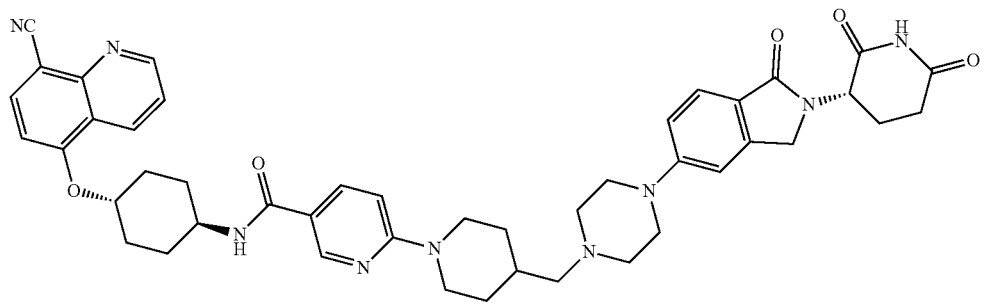 [SMILES: N#Cc1ccc(O[C@H]2CC[C@H](NC(=O)c3ccc(N4CCC(CN5CCN(c6ccc7c(c6)CN([C@H]6CCC(=O)NC6=O)C7=O)CC5)CC4)nc3)CC2)c2cccnc12]

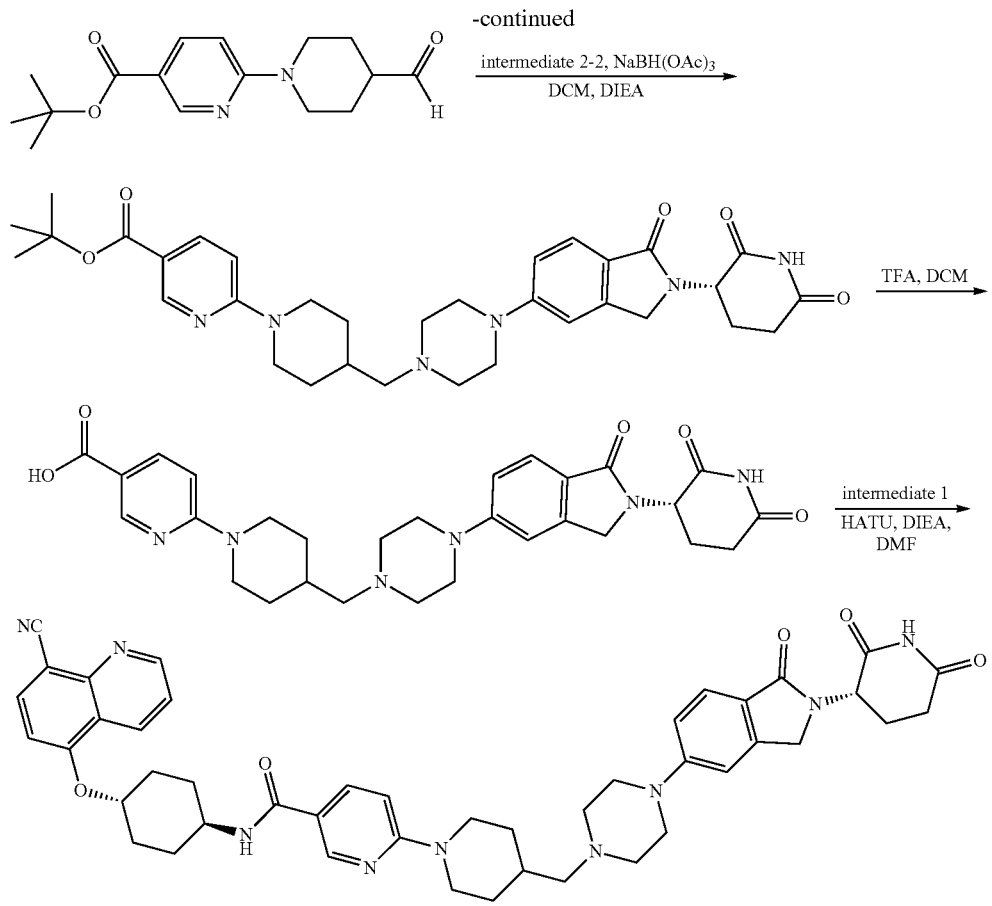

Compound 3-29 was prepared using the similar method as for the preparation of 3-31. The final crude product was purified by prep-TLC (DCM:MeOH=15:1) to afford the desired product as a yellow solid. (23.1 mg, 20.1%). LC/MS: 795.7 [M+H]$^+$; $^1$H NMR (400 MHz, DMSO) δ 10.96 (s, 1H), 9.07 (dd, J=4.2, 1.7 Hz, 1H), 8.68-8.58 (m, 2H), 8.29 (d, J=8.3 Hz, 1H), 8.08 (d, J=7.0 Hz, 1H), 7.96 (d, J=8.6 Hz, 1H), 7.69 (dd, J=8.5, 4.2 Hz, 1H), 7.54 (s, 1H), 7.36 (d, J=8.5 Hz, 1H), 7.09 (br s, 2H), 6.88-6.80 (m, 1H), 5.05 (dd, J=13.1, 4.8 Hz, 1H), 4.78-4.70 (m, 1H), 4.44-4.30 (m, 3H), 4.21 (d, J=12.3 Hz, 1H), 3.86 (m, 1H), 3.64-3.56 (m, 1H), 3.35-3.25 (m, 5H, overlap with DMSO-d6), 3.17-3.10 (m, 1H), 3.01-2.81 (m, 4H), 2.65-2.58 (m, 1H), 2.44-2.17 (m, 5H), 2.00-1.92 (m, 3H), 1.87-1.76 (m, 3H), 1.70-1.53 (m, 4H), 1.30-1.00 (m, 2H).

Synthesis of trans-N-(4-((8-cyanoquinolin-5-yl)oxy)cyclohexyl)-4-(4-(2-(4-(2-(2,6-dioxopiperidin-3-yl)-1,3-dioxoisoindolin-5-yl)piperazin-1-yl)ethyl)piperidin-1-yl)benzamide (3-22)

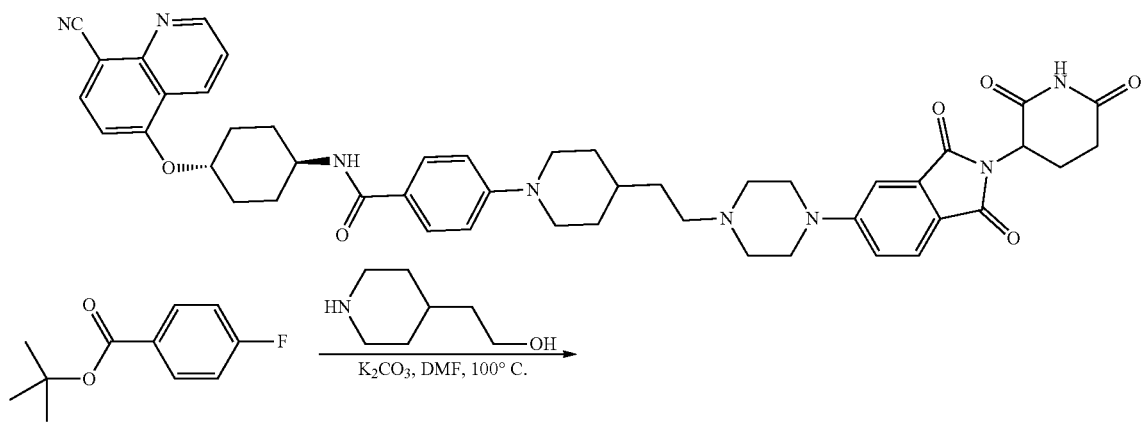

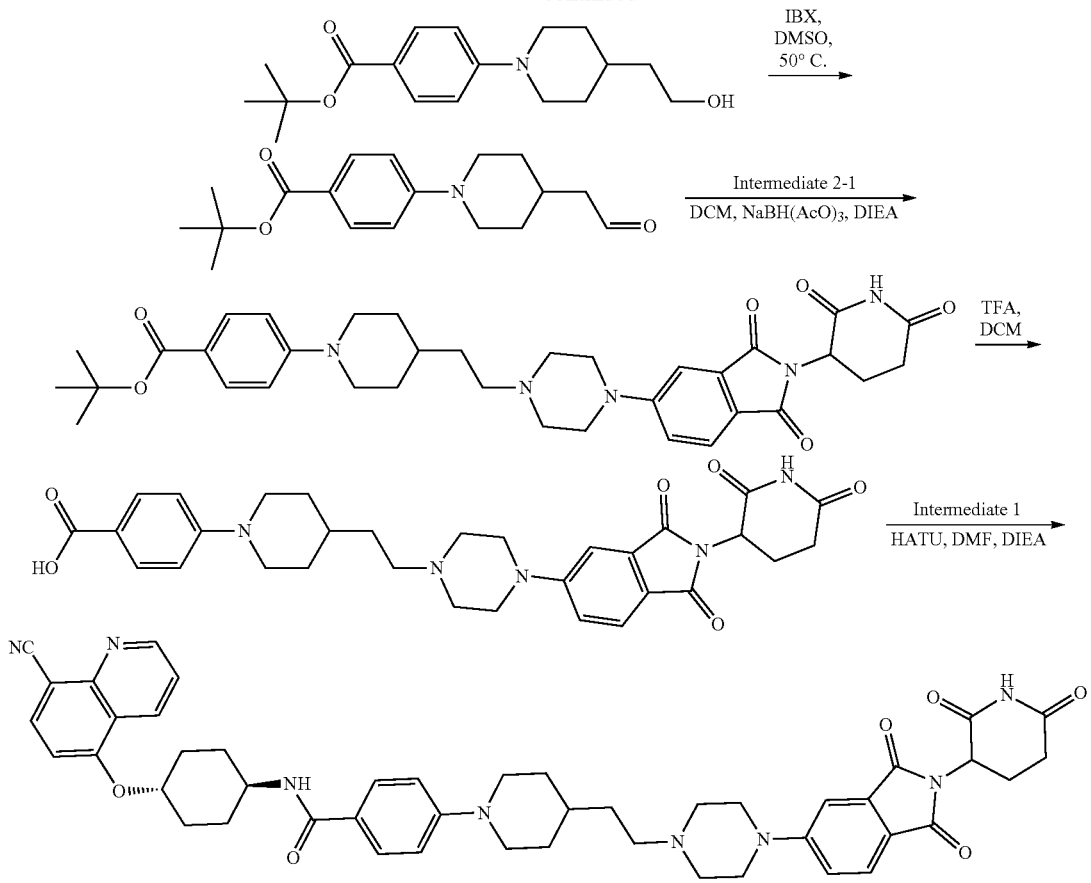

3-22

Step 1: Preparation of tert-butyl 4-(4-(2-hydroxyethyl)piperidin-1-yl)benzoate A solution of tert-butyl 4-fluorobenzoate (200 mg 1.02 mmol), 2-(piperidin-4-yl)ethanol (131.6 mg 1.02 mmol), potassium carbonate (422.6 mg 3.06 mmol) in DMF (5 mL) was stirred under nitrogen at 100° C. for 18 hours. The reaction mixture was concentrated under reduced pressure. The residue was purified by silica gel column chromatography (MeOH:dichloromethane=1:10) to afford the target compound (210 mg, 0.69 mmol, 67% yield) as white solid. LC/MS: 306 [M+H]$^+$.

Step 2: Preparation of tert-butyl 4-(4-(2-oxoethyl)piperidin-1-yl)benzoate

A mixture of tert-butyl 4-[4-(2-hydroxyethyl)piperidin-1-yl]benzoate (200 mg, 0.69 mmol) and IBX (218.42 mg 0.78 mmol) in DMSO (4 mL) was stirred at 50° C. under nitrogen for 18 hours. The reaction mixture was treated with 20 mL of water and extracted with EtOAc (3×5 mL). The combined organic phase was washed with water (5 mL), dried over MgSO$_4$ and concentrated in vacuo. The residue was purified by silica gel column chromatography (EA:dichloromethane=1:5) to afford the target compound (150 mg, 0.49 mmol, 72% yield) as a grey solid. LC/MS: 304.0 [M+H]$^+$.

Step 3: Preparation of tert-butyl 4-(4-(2-(4-(2-(2,6-dioxopiperidin-3-yl)-1,3-dioxoisoindolin-5-yl)piperazin-1-yl)ethyl)piperidin-1-yl)benzoate To a mixture of tert-butyl 4-[4-(2-oxoethyl)piperidin-1-yl]benzoate (150 mg, 0.49 mmol), DIPEA (63.9 mg, 0.49 mmol), Intermediate 2-1 (187.4 mg, 0.49 mmol) and MgSO$_4$ (300 mg) in dichloromethane (3 mL) was added NaHB(OAc)$_3$ (314.4 mg, 1.48 mmol). The mixture was stirred at 25° C. for 18 hours. The residue was diluted with water (50 mL) and extracted with dichloromethane (50 mL×3). The combined organic layers were dried with anhydrous sodium sulfate, filtered and concentrated in vacuum. The residue was purified by reverse phase preparative HPLC to give the desired compound as a yellow solid (240 mg, 0.38 mmol, 78% yield). LC/MS: 630.3 [M+H]$^+$.

Step 4: Preparation of 4-(4-(2-(4-(2-(2,6-dioxopiperidin-3-yl)-1,3-dioxoisoindolin-5-yl)piperazin-1-yl)ethyl)piperidin-1-yl)benzoic Acid A mixture of tert-butyl 4-(4-(2-(4-(2-(2,6-dioxopiperidin-3-yl)-1,3-dioxoisoindolin-5-yl)piperazin-1-yl)ethyl)piperidin-1-yl)benzoate (240 mg, 0.38 mmol) in DCM (5 mL) and TFA (0.5 mL) was stirred at 25° C. for 18 hours. The reaction mixture was concentrated under reduced pressure to afford the target compound (220 mg, 0.38 mmol, 100% yield) as yellow solid. LC/MS: 574.2 [M+H]$^+$.

Step 5: Preparation of trans-N-(4-((8-cyanoquino-lin-5-yl)oxy)cyclohexyl)-4-(4-(2-(4-(2-(2,6-dioxopi-peridin-3-yl)-1,3-dioxoisoindolin-5-yl)piperazin-1-yl)ethyl)piperidin-1-yl)benzamide (3-22)

To a mixture of 4-(4-(2-(4-(2-(2,6-dioxopiperidin-3-yl)-1,3-dioxoisoindolin-5-yl)piperazin-1-yl)ethyl)piperidin-1-yl)benzoic acid (100 mg, 0.17 mmol), Intermediate 1 (53.04 mg, 0.17 mmol), DIEA (90.21 mg, 0.70 mmol), in DMF (1 mL) was added HATU (86.3 mg, 0.23 mmol) portion-wise. The resulting mixture was stirred at 25° C. for 18 hours. The reaction mixture was concentrated under reduced pressure. The residue was purified by silica gel column chromatography (NH$_3$:MeOH:dichloromethane=1:10:100) to afford the target molecule (50 mg, 0.06 mmol, 35% yield) as a brown solid. LC/MS: 823.2 [M+H]$^+$; $^1$H NMR (400 MHz, DMSO) δ 11.10 (s, 1H), 9.08 (dd, J=4.2, 1.7 Hz, 1H), 8.65 (dd, J=8.5, 1.6 Hz, 1H), 8.30 (d, J=8.3 Hz, 1H), 8.00 (d, J=7.6 Hz, 1H), 7.82-7.63 (m, 4H), 7.36 (d, J=8.4 Hz, 2H), 7.27 (d, J=8.6 Hz, 1H), 6.94 (d, J=9.0 Hz, 2H), 5.08 (dd, J=12.9, 5.4 Hz, 1H), 4.80-4.68 (m, 1H), 3.96-3.74 (m, 3H), 3.70-3.53 (m, 1H), 3.53-3.37 (m, 3H), 3.21-3.08 (m, 1H), 2.97-2.80 (m, 1H), 2.80-2.64 (m, 2H), 2.64-2.54 (m, 2H), 2.48-2.30 (m, 5H), 2.30-2.19 (m, 2H), 2.11-1.89 (m, 3H), 1.85-1.39 (m, 9H), 1.35-1.15 (m, 2H).

Testing of Compounds for AR Degradation Activity

LNCAP, VCAP and 22Rv1 cells were plated in 24-well plates at 1.5×10E5 cells/well in the RPMI growth medium containing 10% FBS and 1% Penicillin Streptomycin, and then incubated at 37° C. overnight. The following day, the test compound was administered to the cells by using 1000× compound stock solution prepared in DMSO at various concentrations. After administration of the compound, the cells were then incubated at 37° C. for 24 hours. Upon completion, the cells were washed with PBS and protein was collected in Laemmli sample buffer (1×; VWR International). Proteins in cell lysate were separated by SDS-PAGE and transferred to Odyssey nitrocellulose membranes (Li-cor) with Iblot® dry blotting transfer system (ThermoFisher). Nonspecific binding was blocked by incubating membranes with Intercept Blocking Buffer (Licor) for 1 hour at room temperature with gentle shaking. The membranes were then incubated overnight at 4° C. with Primary antibodies rabbit anti-AR (1:1,000, Cell Signaling, 5153) and mouse anti-GAPDH (1:5,000, Santa Cruz Biotechnology, sc-47724) diluted in Intercept Blocking Buffer containing 0.1% Tween 20. After washing 3 times with TBS-T, the membranes were incubated with IRDye® 800CW goat anti-mouse IgG (1:20,000, Licor) or IRDye® 800CW goat anti-rabbit IgG (1:20,000, Licor) for 1 hour. After TBS-T washes, membranes were rinsed in TBS and scanned on Odyssey® CLx Imaging System (Licor). The bands were quantified using Image Studio™ Software (Licor).

Table 4 summarizes the androgen receptor (AR) degradative activity of exemplary compounds in LNCAP, VCAP and 22Rv1 cell lines 24 hours after administration. DC50: compound concentration needed for 50% target protein degradation.

TABLE 4

| AR degradative activity of compounds from cellular assays | | | |
|---|---|---|---|
| Compounds | LNCAP (DC50, nM) | VCAP (DC50, nM) | 22RV1 (DC50, nM) |
| 3-22 | A | A | N/A |
| 3-18 | A | A | N/A |
| 3-16 | A | A | N/A |
| 3-13 | A | A | N/A |
| 3-15 | A | A | N/A |
| 3-19 | A | A | N/A |
| 3-29 | A | A | A |
| 3-49 | B | N/A | N/A |
| 3-31 | A | A | A |
| 3-35 | A | N/A | N/A |
| 3-50 | A | N/A | N/A |
| 3-51 | A | N/A | N/A |
| 3-30 | A | A | N/A |
| 3-36 | A | A | A |
| 3-53 | A | N/A | N/A |
| 3-9 | A | N/A | N/A |
| 3-11 | A | N/A | N/A |
| 3-43 | A | N/A | N/A |
| 3-17 | A | N/A | N/A |
| 3-52 | A | N/A | N/A |
| 3-54 | A | N/A | N/A |
| 3-55 | A | N/A | N/A |

(A: DC50 < 10 nM; B: DC50 > 100 nM)

The many features and advantages of the present disclosure are apparent from the detailed specification, and thus it is intended by the appended claims to cover all such features and advantages of the present disclosure that fall within the true spirit and scope of the present disclosure. Further, since numerous modifications and variations will readily occur to those skilled in the art, it is not desired to limit the present disclosure to the exact construction and operation illustrated and described and accordingly, all suitable modifications and equivalents may be resorted to, falling within the scope of the present disclosure.

Moreover, those skilled in the art will appreciate that the conception upon which this disclosure is based may readily be used as a basis for designing other structures, methods, and systems for carrying out the several purposes of the present disclosure. Accordingly, the claims are not to be considered as limited by the foregoing description or examples.

What is claimed is:

1. A compound of Formula (1) or a pharmaceutically acceptable salt thereof:

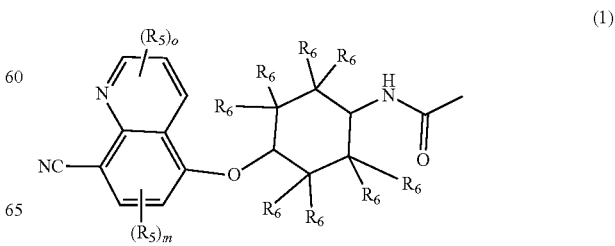

-continued

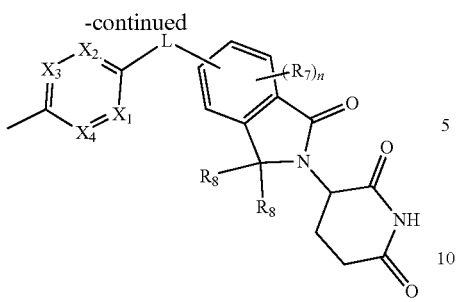

wherein:
X₁ is CR₁ or N;
X₂ is CR₂ or N;
X₃ is CR₃ or N;
X₄ is CR₄ or N;
each of $R_1$, $R_2$, $R_3$, and $R_4$ is independently selected from hydrogen, halogen, $C_1$-$C_3$alkoxy, and $C_1$-$C_3$haloalkyl, each of which is substituted with 0, 1, 2, or 3 $R_S$;
each $R_5$ is independently selected from halogen, hydroxyl, $C_1$-$C_3$alkyl, $C_1$-$C_3$alkoxy, $C_1$-$C_3$haloalkyl, —N($R_9$)$_2$, and —CN, each of which is substituted with 0, 1, 2, or 3 $R_S$;
each $R_6$ is independently selected from hydrogen, halogen, $C_1$-$C_3$alkyl, and $C_1$-$C_3$haloalkyl, each of which is substituted with 0, 1, 2, or 3 $R_S$, or two $R_6$ groups are taken together to form an oxo;
each $R_7$ is independently selected from halogen, hydroxyl, $C_1$-$C_3$alkyl, $C_1$-$C_3$alkoxy, $C_1$-$C_3$haloalkyl, —N($R_9$)$_2$, and —CN, each of which is substituted with 0, 1, 2, or 3 $R_S$;
each $R_8$ is independently selected from hydrogen, hydroxyl, $C_1$-$C_3$alkyl, and $C_1$-$C_3$haloalkyl, each of which is substituted with 0, 1, 2, or 3 $R_S$, or two $R_8$ groups are taken together to form an oxo;
each $R_9$ is independently selected from hydrogen, $C_1$-$C_3$alkyl, —C(=O)—($C_1$-$C_3$alkyl), —C(=O)—O—($C_1$-$C_3$alkyl), and —C(=O)—NH—($C_1$-$C_3$alkyl), each of which is substituted with 0, 1, 2, or 3 $R_S$, or two $R_9$ groups are taken together to form a 3- to 6-membered heterocycle or heteroaryl;
each $R_S$ is independently selected from halogen, hydroxyl, $C_1$-$C_3$alkyl, $C_1$-$C_3$alkoxy, $C_1$-$C_3$haloalkyl, —N($R_9$)$_2$, and —CN;
L is a linker of 1 to 16 carbon atoms in length, wherein one or more carbon atoms are optionally replaced by C(O), O, N($R_9$), S, $C_2$-alkenyl, $C_2$-alkynyl, cycloalkyl, aryl, heterocycle, or heteroaryl, wherein the $R_9$, $C_2$-alkenyl, cycloalkyl, aryl, heterocycle, and heteroaryl are each independently substituted with 0, 1, 2, or 3 $R_S$;
m is 0, 1, or 2;
n is 0, 1, 2, or 3; and
o is 0, 1, 2, or 3,
wherein each hydrogen atom is independently and optionally replaced by a deuterium atom.

2. The compound or pharmaceutically acceptable salt thereof according to claim 1, wherein X₂ is CR₂, X₃ is CR₃, and X₄ is CR₄.

3. The compound or pharmaceutically acceptable salt thereof according to claim 2, wherein R₂, R₃, and R₄ are each independently selected from H and F.

4. The compound or pharmaceutically acceptable salt thereof according to claim 1, wherein X₁ is CR₁, X₂ is CR₂, X₃ is CR₃, and X₄ is CR₄.

5. The compound or pharmaceutically acceptable salt thereof according to claim 4, wherein R₁, R₂, R₃, and R₄ are each independently selected from H and F.

6. The compound or pharmaceutically acceptable salt thereof according to claim 1, wherein the

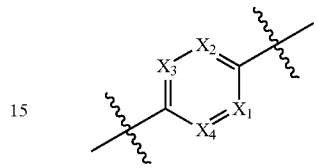

group is selected from

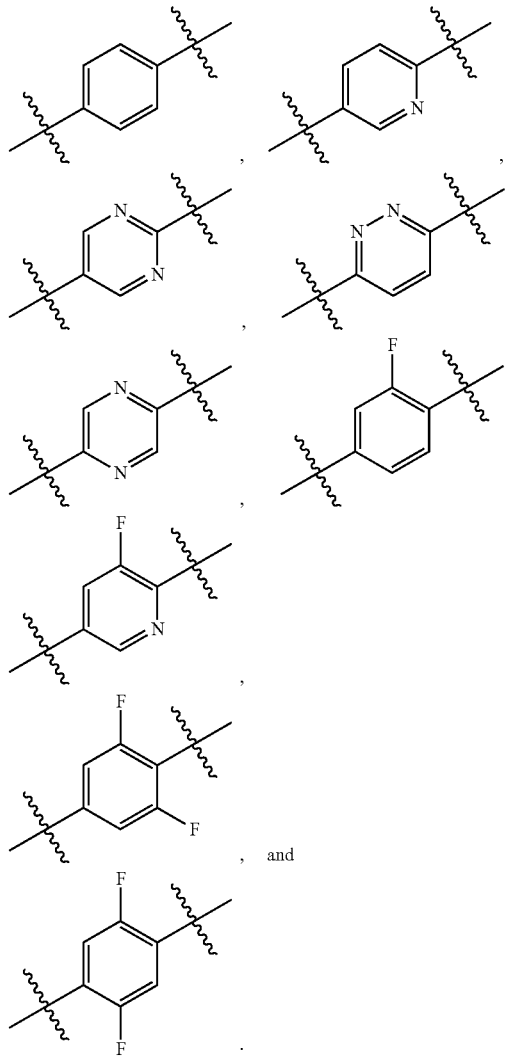

7. The compound or pharmaceutically acceptable salt thereof according to claim 1, wherein each $R_5$ is independently selected from halogen, $C_1$-$C_3$alkoxy, and $C_1$-$C_3$haloalkyl.

8. The compound or pharmaceutically acceptable salt thereof according to claim 7, wherein each $R_5$ is independently selected from —Cl, —OCH$_3$, and —CF$_3$.

9. The compound or pharmaceutically acceptable salt thereof according to claim 1, wherein m is 0 or 1.

10. The compound or pharmaceutically acceptable salt according to claim 1, wherein o is 0 or 1.

11. The compound or pharmaceutically acceptable salt thereof according to claim 1, wherein each $R_6$ is independently selected from H and $C_1$-$C_3$alkyl.

12. The compound or pharmaceutically acceptable salt thereof according to claim 1, wherein each $R_6$ is independently selected from H and —CH$_3$.

13. The compound or pharmaceutically acceptable salt thereof according to claim 1, wherein the two $R_6$ groups attached to the same carbon are identical.

14. The compound or pharmaceutically acceptable salt thereof according to claim 1, wherein the

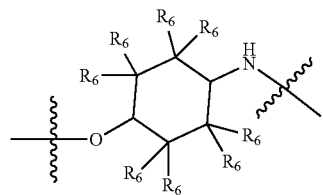

group is selected from

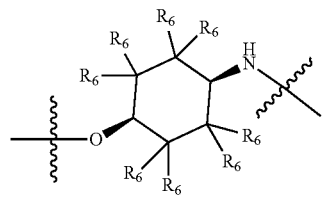

,

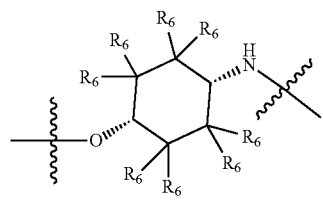

,

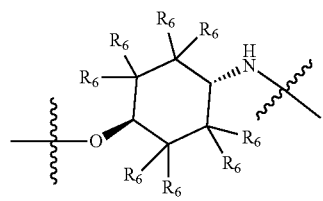

,

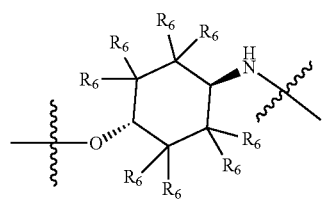

, and

.

15. The compound or pharmaceutically acceptable salt thereof according to claim 1, wherein the

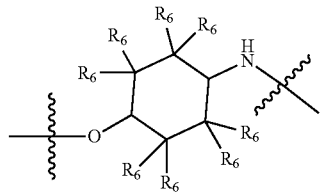

group is selected from

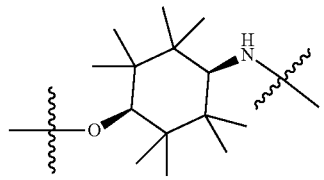

,

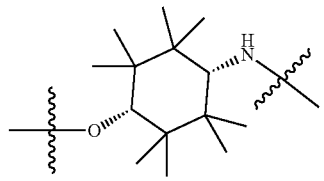

,

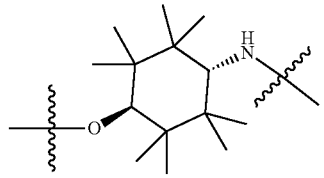

,

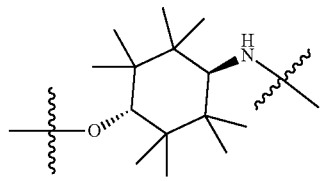

,

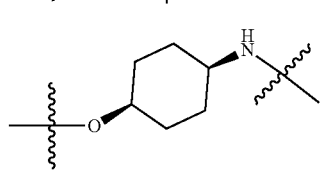

,

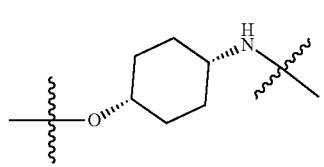

,

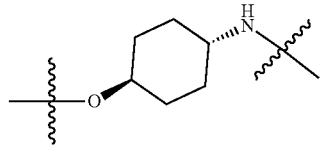

, and

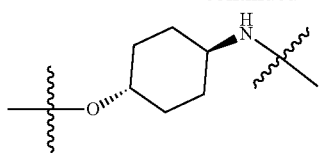

16. The compound or pharmaceutically acceptable salt thereof according to claim 1, wherein each $R_7$ is independently selected from halogen, hydroxyl, $C_1$-$C_3$alkyl, and $C_1$-$C_3$haloalkyl.

17. The compound or pharmaceutically acceptable salt thereof according to claim 16, wherein each $R_7$ is independently selected from halogen, hydroxyl, —$CH_3$, and —$CF_3$.

18. The compound or pharmaceutically acceptable salt thereof according to claim 1, wherein n is 0 or 1.

19. The compound or pharmaceutically acceptable salt thereof according to claim 1, wherein each $R_8$ is hydrogen or two $R_8$ groups are taken together to form an oxo.

20. The compound or pharmaceutically acceptable salt thereof according to claim 1, wherein each $R_9$ is independently selected from hydrogen, $C_1$-$C_3$alkyl, and —C(=O)—$C_1$-$C_3$alkyl.

21. The compound or pharmaceutically acceptable salt thereof according to claim 20, wherein each $R_9$ is independently selected from hydrogen, —$CH_3$, —$CH_2CH_3$, and —$CH(CH_3)_2$.

22. The compound or pharmaceutically acceptable salt thereof according to claim 1, wherein the

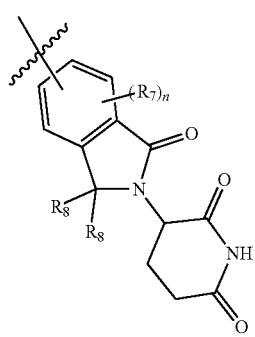

group is selected from

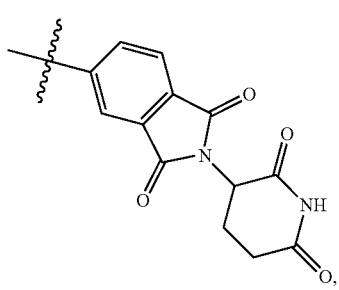

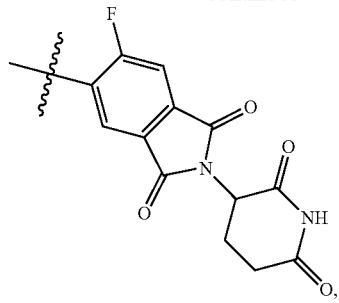

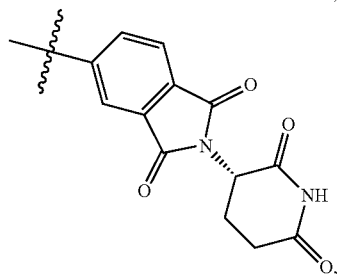

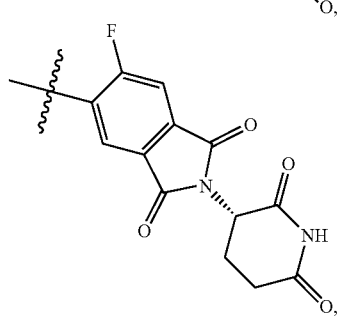

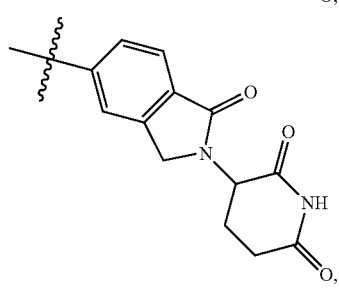

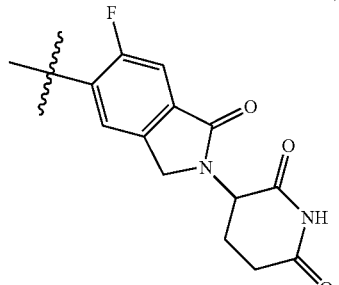

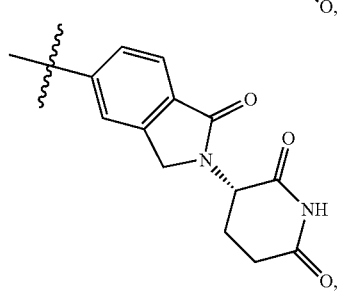

-continued

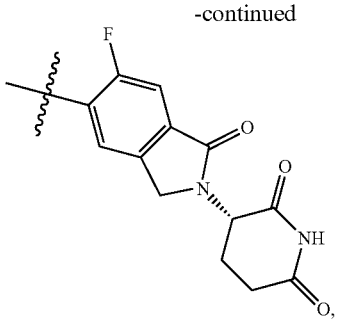

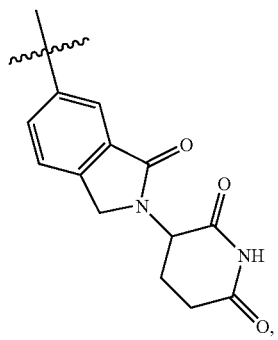

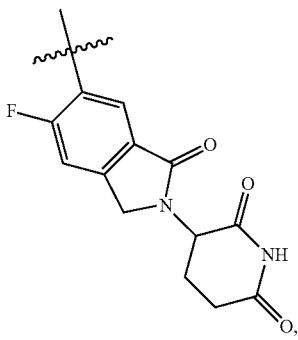

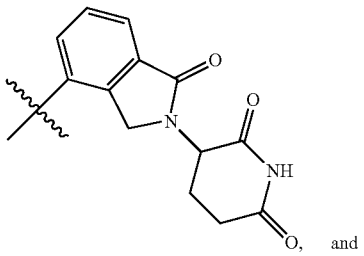

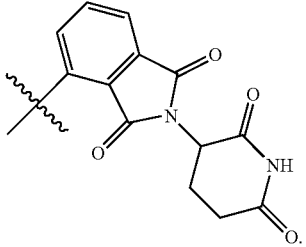 and

23. The compound or pharmaceutically acceptable salt thereof according to claim 1, wherein L is a linker of 1 to 6 carbon atoms in length, wherein one or more carbon atoms are optionally replaced by C(=O), O, N(R$_9$), S, C$_2$-alkenyl, C$_2$-alkynyl, cycloalkyl, aryl, heterocycle, or heteroaryl, wherein the R$_9$, C$_2$-alkenyl, cycloalkyl, aryl, heterocycle, and heteroaryl are each independently substituted with 0, 1, 2, or 3 R$_S$.

24. The compound or pharmaceutically acceptable salt thereof according to claim 1, wherein one or more carbon atoms of linker L are optionally replaced by O, N(R$_9$), cycloalkyl, or heterocycle, wherein the R$_9$, cycloalkyl, and heterocycle are each independently substituted with 0, 1, 2, or 3 R$_S$.

25. The compound or pharmaceutically acceptable salt thereof according to claim 1, wherein at least two carbon atoms of linker L are replaced by a heterocycle, each of which is substituted with 0, 1, 2, or 3 R$_S$.

26. The compound or pharmaceutically acceptable salt thereof according to claim 25, wherein the heterocycle is selected from piperidine and piperazine, each of which is substituted with 0, 1, 2, or 3 R$_S$.

27. The compound or pharmaceutically acceptable salt thereof according to 24, wherein the heterocycle is selected from

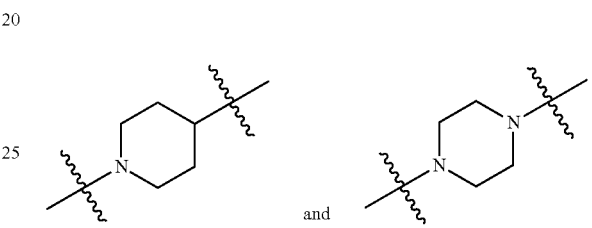

and

28. The compound or pharmaceutically acceptable salt thereof according to claim 1, wherein L is selected from:

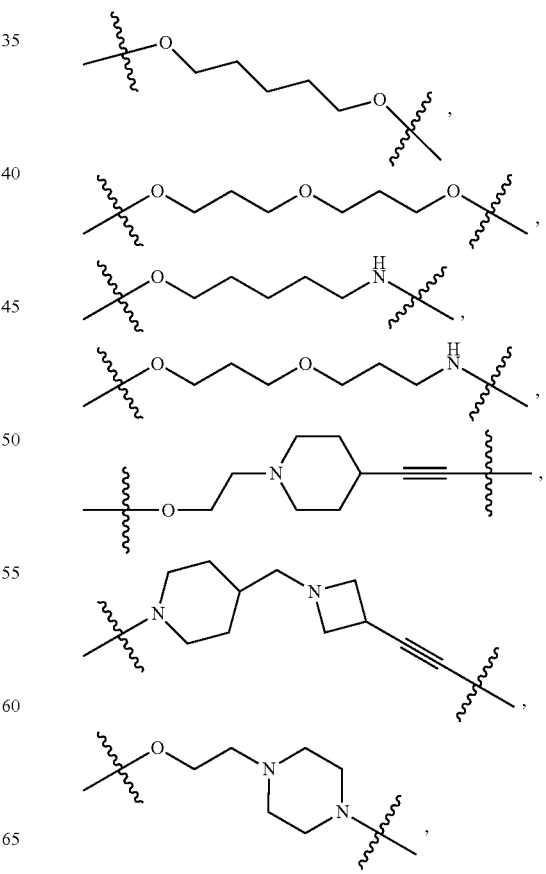

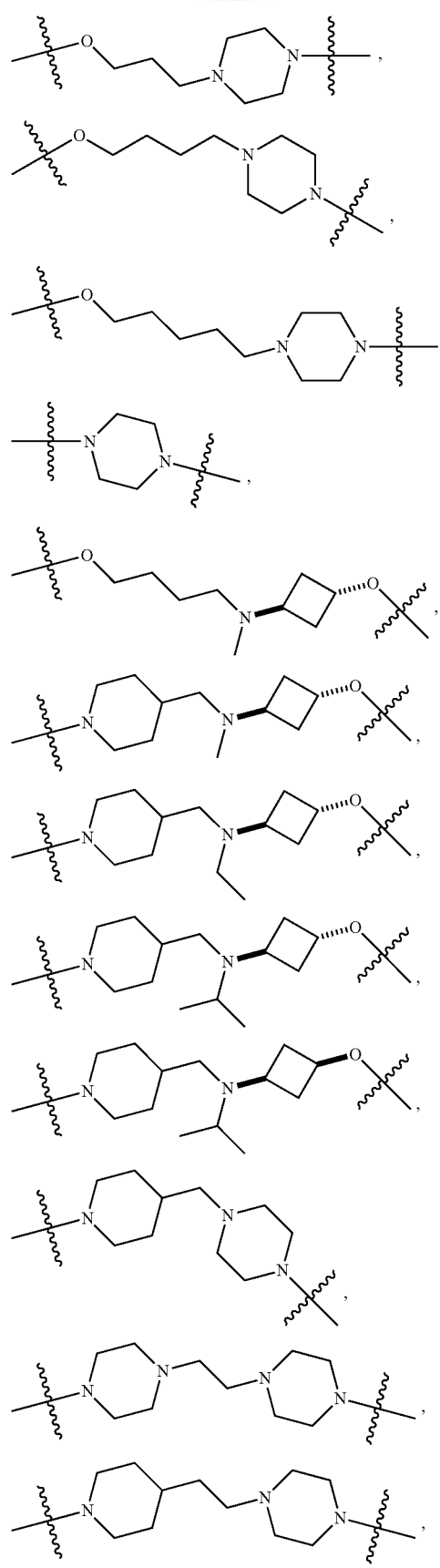
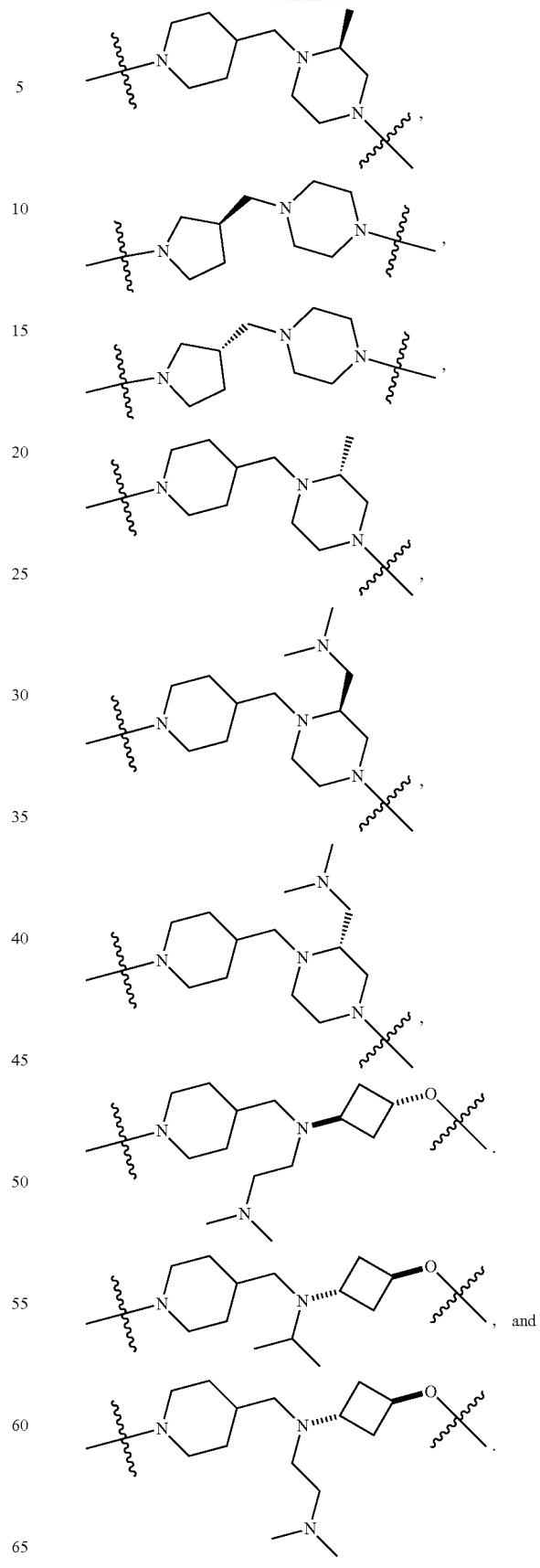

29. A compound selected from:

N-((1r,4r)-4-((8-cyanoquinolin-5-yl)oxy)cyclohexyl)-4-((5-((2-(2,6-dioxopiperidin-3-yl)-1,3-dioxoisoindolin-5-yl)oxy)pentyl)oxy)benzamide;

N-((1r,4r)-4-((8-cyanoquinolin-5-yl)oxy)cyclohexyl)-4-(3-(3-((2-(2,6-dioxopiperidin-3-yl)-1,3-dioxoisoindolin-5-yl)oxy)propoxy)propoxy)benzamide;

N-((1r,4r)-4-((8-cyanoquinolin-5-yl)oxy)cyclohexyl)-4-(2-(4-(2-(2,6-dioxopiperidin-3-yl)-1,3-dioxoisoindolin-5-yl)piperazin-1-yl)ethoxy)benzamide;

N-((1r,4r)-4-((8-cyanoquinolin-5-yl)oxy)cyclohexyl)-4-(3-(4-(2-(2,6-dioxopiperidin-3-yl)-1,3-dioxoisoindolin-5-yl)piperazin-1-yl)propoxy)benzamide;

N-((1r,4r)-4-((8-cyanoquinolin-5-yl)oxy)cyclohexyl)-4-(4-(4-(2-(2,6-dioxopiperidin-3-yl)-1,3-dioxoisoindolin-5-yl)piperazin-1-yl)butoxy)benzamide;

N-((1r,4r)-4-((8-cyanoquinolin-5-yl)oxy)cyclohexyl)-4-((5-(4-(2-(2,6-dioxopiperidin-3-yl)-1,3-dioxoisoindolin-5-yl)piperazin-1-yl)pentyl)oxy)benzamide;

N-((1 r,4r)-4-((8-cyanoquinolin-5-yl)oxy)cyclohexyl)-6-(4-(2-(2,6-dioxopiperidin-3-yl)-1,3-dioxoisoindolin-5-yl)piperazin-1-yl)nicotinamide;

N-((1 r,4r)-4-((8-cyanoquinolin-5-yl)oxy)cyclohexyl)-4-(4-(((1 r,3r)-3-((2-(2,6-dioxopiperidin-3-yl)-1,3-dioxoisoindolin-5-yl)oxy)cyclobutyl)(methyl)amino)butoxy)benzamide;

N-((1 r,4r)-4-((8-cyanoquinolin-5-yl)oxy)cyclohexyl)-6-(4-((((1 r,3r)-3-((2-(2,6-dioxopiperidin-3-yl)-1,3-dioxoisoindolin-5-yl)oxy)cyclobutyl)(methyl)amino)methyl)piperidin-1-yl)nicotinamide;

N-((1 r,4r)-4-((8-cyanoquinolin-5-yl)oxy)cyclohexyl)-6-(4-((((1 r,3r)-3-((2-(2,6-dioxopiperidin-3-yl)-1,3-dioxoisoindolin-5-yl)oxy)cyclobutyl)(ethyl)amino)methyl)piperidin-1-yl)nicotinamide;

N-((1 r,4r)-4-((8-cyanoquinolin-5-yl)oxy)cyclohexyl)-6-(4-((((1 r,3r)-3-((2-(2,6-dioxopiperidin-3-yl)-1,3-dioxoisoindolin-5-yl)oxy)cyclobutyl)(isopropyl)amino)methyl)piperidin-1-yl)nicotinamide;

N-((1 r,4r)-4-((8-cyanoquinolin-5-yl)oxy)cyclohexyl)-6-(4-((((1 s,3s)-3-((2-(2,6-dioxopiperidin-3-yl)-1,3-dioxoisoindolin-5-yl)oxy)cyclobutyl)(isopropyl)amino)methyl)piperidin-1-yl)nicotinamide;

N-((1 r,4r)-4-((8-cyanoquinolin-5-yl)oxy)cyclohexyl)-6-(4-((4-(2-(2,6-dioxopiperidin-3-yl)-1,3-dioxoisoindolin-5-yl)piperazin-1-yl)methyl)piperidin-1-yl)nicotinamide;

N-((1 s,4s)-4-((8-cyanoquinolin-5-yl)oxy)cyclohexyl)-6-(4-((4-(2-(2,6-dioxopiperidin-3-yl)-1,3-dioxoisoindolin-5-yl)piperazin-1-yl)methyl)piperidin-1-yl)nicotinamide;

N-((1 r,4r)-4-((8-cyanoquinolin-5-yl)oxy)cyclohexyl)-2-(4-((4-(2-(2,6-dioxopiperidin-3-yl)-1,3-dioxoisoindolin-5-yl)piperazin-1-yl)methyl)piperidin-1-yl)pyrimidine-5-carboxamide;

N-((1 r,4r)-4-((8-cyanoquinolin-5-yl)oxy)cyclohexyl)-6-(4-((4-(2-(2,6-dioxopiperidin-3-yl)-1,3-dioxoisoindolin-5-yl)piperazin-1-yl)methyl)piperidin-1-yl)pyridazine-3-carboxamide;

N-((1 r,4r)-4-((8-cyanoquinolin-5-yl)oxy)cyclohexyl)-5-(4-((4-(2-(2,6-dioxopiperidin-3-yl)-1,3-dioxoisoindolin-5-yl)piperazin-1-yl)methyl)piperidin-1-yl)pyrazine-2-carboxamide;

N-((1r,4r)-4-((8-cyanoquinolin-5-yl)oxy)cyclohexyl)-4-(4-((4-(2-(2,6-dioxopiperidin-3-yl)-1,3-dioxoisoindolin-5-yl)piperazin-1-yl)methyl)piperidin-1-yl)benzamide;

N-((1r,4r)-4-((8-cyanoquinolin-5-yl)oxy)cyclohexyl)-4-(4-((4-(2-(2,6-dioxopiperidin-3-yl)-1,3-dioxoisoindolin-5-yl)piperazin-1-yl)methyl)piperidin-1-yl)-3-fluorobenzamide;

N-((1r,4r)-4-((8-cyanoquinolin-5-yl)oxy)cyclohexyl)-4-(4-(2-(4-(2-(2,6-dioxopiperidin-3-yl)-1,3-dioxoisoindolin-5-yl)piperazin-1-yl)ethyl)piperidin-1-yl)-3-fluorobenzamide;

N-((1r,4r)-4-((8-cyanoquinolin-5-yl)oxy)cyclohexyl)-4-(4-(2-(4-(2-(2,6-dioxopiperidin-3-yl)-1,3-dioxoisoindolin-5-yl)piperazin-1-yl)ethyl)piperazin-1-yl)benzamide;

N-((1r,4r)-4-((8-cyanoquinolin-5-yl)oxy)cyclohexyl)-4-(4-(2-(4-(2-(2,6-dioxopiperidin-3-yl)-1,3-dioxoisoindolin-5-yl)piperazin-1-yl)ethyl)piperidin-1-yl)benzamide;

N-((1r,4r)-4-((8-cyanoquinolin-5-yl)oxy)cyclohexyl)-6-(4-(2-(4-(2-(2,6-dioxopiperidin-3-yl)-1,3-dioxoisoindolin-5-yl)piperazin-1-yl)ethyl)piperidin-1-yl)nicotinamide;

N-((1r,4r)-4-((8-cyanoquinolin-5-yl)oxy)cyclohexyl)-2-(4-(2-(4-(2-(2,6-dioxopiperidin-3-yl)-1,3-dioxoisoindolin-5-yl)piperazin-1-yl)ethyl)piperidin-1-yl)pyrimidine-5-carboxamide;

N-((1r,4r)-4-((8-cyanoquinolin-5-yl)oxy)cyclohexyl)-6-(4-(2-(4-(2-(2,6-dioxopiperidin-3-yl)-1,3-dioxoisoindolin-5-yl)piperazin-1-yl)ethyl)piperidin-1-yl)pyridazine-3-carboxamide;

N-((1r,4r)-4-((8-cyanoquinolin-5-yl)oxy)cyclohexyl)-5-(4-(2-(4-(2-(2,6-dioxopiperidin-3-yl)-1,3-dioxoisoindolin-5-yl)piperazin-1-yl)ethyl)piperidin-1-yl)pyrazine-2-carboxamide;

N-((1r,4r)-4-((8-cyanoquinolin-5-yl)oxy)cyclohexyl)-6-(4-((4-(2-(2,6-dioxopiperidin-3-yl)-1,3-dioxoisoindolin-5-yl)piperazin-1-yl)methyl)piperidin-1-yl)-5-fluoronicotinamide;

N-((1r,4r)-4-((8-cyanoquinolin-5-yl)oxy)cyclohexyl)-6-(4-(2-(4-(2-(2,6-dioxopiperidin-3-yl)-1,3-dioxoisoindolin-5-yl)piperazin-1-yl)ethyl)piperidin-1-yl)-5-fluoronicotinamide;

N-((1r,4r)-4-((8-cyanoquinolin-5-yl)oxy)cyclohexyl)-6-(4-((4-(2-((S)-2,6-dioxopiperidin-3-yl)-1-oxoisoindolin-5-yl)piperazin-1-yl)methyl)piperidin-1-yl)nicotinamide;

N-((1r,4r)-4-((8-cyanoquinolin-5-yl)oxy)cyclohexyl)-2-(4-((4-(2-((S)-2,6-dioxopiperidin-3-yl)-1-oxoisoindolin-5-yl)piperazin-1-yl)methyl)piperidin-1-yl)pyrimidine-5-carboxamide;

N-((1r,4r)-4-((8-cyanoquinolin-5-yl)oxy)cyclohexyl)-4-((4-(2-((S)-2,6-dioxopiperidin-3-yl)-1-oxoisoindolin-5-yl)piperazin-1-yl)methyl)piperidin-1-yl)-3-fluorobenzamide;

N-((1r,4r)-4-((8-cyanoquinolin-5-yl)oxy)cyclohexyl)-6-(4-((4-(2-((S)-2,6-dioxopiperidin-3-yl)-1-oxoisoindolin-5-yl)piperazin-1-yl)methyl)piperidin-1-yl)pyridazine-3-carboxamide;

N-((1r,4r)-4-((8-cyanoquinolin-5-yl)oxy)cyclohexyl)-6-(4-((4-(2-((S)-2,6-dioxopiperidin-3-yl)-6-fluoro-1-oxoisoindolin-5-yl)piperazin-1-yl)methyl)piperidin-1-yl)nicotinamide;

N-((1r,4r)-4-((8-cyanoquinolin-5-yl)oxy)cyclohexyl)-6-(4-((4-(2-((S)-2,6-dioxopiperidin-3-yl)-6-fluoro-1-oxoisoindolin-5-yl)piperazin-1-yl)methyl)piperidin-1-yl)pyridazine-3-carboxamide;

N-((1r,4r)-4-((8-cyanoquinolin-5-yl)oxy)cyclohexyl)-6-(4-((4-(2-(2,6-dioxopiperidin-3-yl)-6-fluoro-1,3-dioxoisoindolin-5-yl)piperazin-1-yl)methyl)piperidin-1-yl)nicotinamide;

N-((1r,4r)-4-((8-cyanoquinolin-5-yl)oxy)cyclohexyl)-6-(4-((4-(2-(2,6-dioxopiperidin-3-yl)-6-fluoro-1,3-dioxoisoindolin-5-yl)piperazin-1-yl)methyl)piperidin-1-yl)pyridazine-3-carboxamide;

N-((1r,4r)-4-((8-cyanoquinolin-5-yl)oxy)cyclohexyl)-6-(4-(((2S)-4-(2-(2,6-dioxopiperidin-3-yl)-1,3-dioxoisoindolin-5-yl)-2-methylpiperazin-1-yl)methyl)piperidin-1-yl)nicotinamide;

N-((1r,4r)-4-((8-cyanoquinolin-5-yl)oxy)cyclohexyl)-6-(4-(((2R)-4-(2-(2,6-dioxopiperidin-3-yl)-1,3-dioxoisoindolin-5-yl)-2-methylpiperazin-1-yl)methyl)piperidin-1-yl)nicotinamide;

N-((1r,4r)-4-((8-cyanoquinolin-5-yl)oxy)cyclohexyl)-4-(4-(((2S)-4-(2-(2,6-dioxopiperidin-3-yl)-1,3-dioxoisoindolin-5-yl)-2-methylpiperazin-1-yl)methyl)piperidin-1-yl)-3-fluorobenzamide;

N-((1 r,4r)-4-((8-cyanoquinolin-5-yl)oxy)cyclohexyl)-4-(4-(((2R)-4-(2-(2,6-dioxopiperidin-3-yl)-1,3-dioxoisoindolin-5-yl)-2-methylpiperazin-1-yl)methyl)piperidin-1-yl)-3-fluorobenzamide;

N-((1 r,4r)-4-((8-cyanoquinolin-5-yl)oxy)cyclohexyl)-4-(4-(((2S)-2-((dimethylamino)methyl)-4-(2-(2,6-dioxopiperidin-3-yl)-1,3-dioxoisoindolin-5-yl)piperazin-1-yl)methyl)piperidin-1-yl)-3-fluorobenzamide;

N-((1 r,4r)-4-((8-cyanoquinolin-5-yl)oxy)cyclohexyl)-4-(4-(((2R)-2-((dimethylamino)methyl)-4-(2-(2,6-dioxopiperidin-3-yl)-1,3-dioxoisoindolin-5-yl)piperazin-1-yl)methyl)piperidin-1-yl)-3-fluorobenzamide;

N-((1 r,4r)-4-((8-cyanoquinolin-5-yl)oxy)cyclohexyl)-6-(4-((((1 r,3r)-3-((2-(2,6-dioxopiperidin-3-yl)-1,3-dioxoisoindolin-5-yl)oxy)cyclobutyl)(isopropyl)amino)methyl)piperidin-1-yl)pyridazine-3-carboxamide;

N-((1 r,4r)-4-((8-cyanoquinolin-5-yl)oxy)cyclohexyl)-4-(4-(((2-(dimethylamino)ethyl)((1 r,3r)-3-((2-(2,6-dioxopiperidin-3-yl)-1,3-dioxoisoindolin-5-yl)oxy)cyclobutyl)amino)methyl)piperidin-1-yl)-3-fluorobenzamide;

N-((1 r,4r)-4-((8-cyanoquinolin-5-yl)oxy)cyclohexyl)-6-(4-(((2S)-2-((dimethylamino)methyl)-4-(2-(2,6-dioxopiperidin-3-yl)-1,3-dioxoisoindolin-5-yl)piperazin-1-yl)methyl)piperidin-1-yl)nicotinamide;

N-((1 r,4r)-4-((8-cyanoquinolin-5-yl)oxy)cyclohexyl)-6-(4-(((2R)-2-((dimethylamino)methyl)-4-(2-(2,6-dioxopiperidin-3-yl)-1,3-dioxoisoindolin-5-yl)piperazin-1-yl)methyl)piperidin-1-yl)nicotinamide;

N-((1 r,4r)-4-((8-cyanoquinolin-5-yl)oxy)cyclohexyl)-6-(4-((4-(2-((S)-2,6-dioxopiperidin-3-yl)-6-fluoro-1-oxoisoindolin-5-yl)piperazin-1-yl)methyl)piperidin-1-yl)-5-fluoronicotinamide;

N-((1 r,4r)-4-((8-cyanoquinolin-5-yl)oxy)cyclohexyl)-2-(4-((4-(2-((S)-2,6-dioxopiperidin-3-yl)-6-fluoro-1-oxoisoindolin-5-yl)piperazin-1-yl)methyl)piperidin-1-yl)pyrimidine-5-carboxamide;

N-((1 r,4r)-4-((8-cyanoquinolin-5-yl)oxy)cyclohexyl)-4-(4-((4-(2-(2,6-dioxopiperidin-3-yl)-6-fluoro-1,3-dioxoisoindolin-5-yl)piperazin-1-yl)methyl)piperidin-1-yl)benzamide;

N-((1 r,4r)-4-((8-cyanoquinolin-5-yl)oxy)cyclohexyl)-4-(4-((4-(2-(2,6-dioxopiperidin-3-yl)-6-fluoro-1,3-dioxoisoindolin-5-yl)piperazin-1-yl)methyl)piperidin-1-yl)-3-fluorobenzamide;

N-((1r,4r)-4-((8-cyanoquinolin-5-yl)oxy)cyclohexyl)-2-(4-((4-(2-(2,6-dioxopiperidin-3-yl)-6-fluoro-1,3-dioxoisoindolin-5-yl)piperazin-1-yl)methyl)piperidin-1-yl)pyrimidine-5-carboxamide;

N-((1r,4r)-4-((8-cyanoquinolin-5-yl)oxy)cyclohexyl)-5-(4-((4-(2-(2,6-dioxopiperidin-3-yl)-6-fluoro-1,3-dioxoisoindolin-5-yl)piperazin-1-yl)methyl)piperidin-1-yl)pyrazine-2-carboxamide;

N-((1r,4r)-4-((8-cyanoquinolin-5-yl)oxy)cyclohexyl)-6-(4-((4-(2-(2,6-dioxopiperidin-3-yl)-6-fluoro-1,3-dioxoisoindolin-5-yl)piperazin-1-yl)methyl)piperidin-1-yl)-5-fluoronicotinamide;

N-((1r,4S)-4-((8-cyanoquinolin-5-yl)oxy)cyclohexyl)-2-((3S)-3-((4-(2-(2,6-dioxopiperidin-3-yl)-1,3-dioxoisoindolin-5-yl)piperazin-1-yl)methyl)pyrrolidin-1-yl)pyrimidine-5-carboxamide;

N-((1r,4R)-4-((8-cyanoquinolin-5-yl)oxy)cyclohexyl)-2-((3R)-3-((4-(2-(2,6-dioxopiperidin-3-yl)-1,3-dioxoisoindolin-5-yl)piperazin-1-yl)methyl)pyrrolidin-1-yl)pyrimidine-5-carboxamide;

or a pharmaceutically acceptable salt thereof, wherein each hydrogen is independently and optionally replaced by a deuterium.

30. A pharmaceutical composition comprising at least one compound or pharmaceutically acceptable salt thereof according to claim 1 or claim 29 and a pharmaceutically acceptable carrier.

31. A method of treating cancer in a subject in need thereof, comprising administering to the subject an effective amount of a compound according to claim 1 or claim 29, wherein the cancer is selected from prostate cancer, head and neck cancer, skin cancer, sarcoma, renal cell carcinoma, adrenocortical carcinoma, bladder cancer, lung cancer, gastric carcinoma, esophageal carcinoma, pancreatic adenocarcinoma, colorectal cancer, connective tissue cancer, glioblastoma multiforme, cervical cancer, uterine cancer, ovarian cancer, and breast cancer.

32. The method according to claim 31, wherein the subject has been previously treated with an anti-cancer agent chosen from enzalutamide, apalutamide, bicalutamide, darolutamide, flutamide, abiraterone, or a combination thereof.

33. A method of inhibiting cell growth, comprising contacting a cell with a compound or pharmaceutically acceptable salt thereof according to claim 1 or claim 29.

34. The compound of Formula (1) according to claim 1, wherein the compound is a compound of Formula (1A)
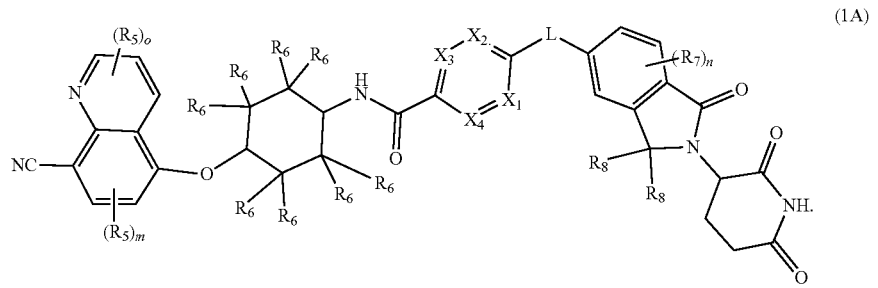
* * * * *